(12) United States Patent
Winter et al.

(10) Patent No.: US 9,249,505 B2
(45) Date of Patent: *Feb. 2, 2016

(54) BIS(TRIMETHYLSILYL) SIX-MEMBERED RING SYSTEMS AND RELATED COMPOUNDS AS REDUCING AGENTS FOR FORMING LAYERS ON A SUBSTRATE

(71) Applicant: Wayne State University, Detroit, MI (US)

(72) Inventors: Charles H. Winter, Bloomfield Hills, MI (US); Joseph Peter Klesko, Hamtramck, MI (US)

(73) Assignee: Wayne State University, Detroit, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/318,501

(22) Filed: Jun. 27, 2014

(65) Prior Publication Data

US 2015/0004314 A1   Jan. 1, 2015

Related U.S. Application Data

(63) Continuation-in-part of application No. 13/930,471, filed on Jun. 28, 2013.

(60) Provisional application No. 61/974,115, filed on Apr. 2, 2014, provisional application No. 61/902,264, filed on Nov. 10, 2013.

(51) Int. Cl.
*C23C 16/00* (2006.01)
*C23C 16/18* (2006.01)
*C01B 33/025* (2006.01)
(Continued)

(52) U.S. Cl.
CPC .............. *C23C 16/18* (2013.01); *C01B 33/025* (2013.01); *C01G 3/05* (2013.01); *C23C 16/45553* (2013.01); *C01P 2002/72* (2013.01); *C01P 2002/85* (2013.01); *C01P 2004/03* (2013.01); *C01P 2004/04* (2013.01); *Y10T 137/8593* (2015.04)

(58) Field of Classification Search
CPC ................... C23C 16/45525–16/45555; C23C 16/06–16/18
See application file for complete search history.

(56) References Cited

U.S. PATENT DOCUMENTS 3,562,308 A   2/1971  Costa et al.
5,721,014 A   2/1998  Fakler et al.
(Continued)

FOREIGN PATENT DOCUMENTS

KR  10-2010-0061183 A  6/2010
WO     2012027357 A2   3/2012
WO     2012/067439 A2  5/2012

OTHER PUBLICATIONS

Final Office Action Mailed Sep. 24, 2014 in U.S. Appl. No. 13/493,560, filed Jun. 11, 2012, 23 pgs.
(Continued)

*Primary Examiner* — Elizabeth Burkhart
(74) *Attorney, Agent, or Firm* — Brooks Kushman P.C.

(57) ABSTRACT

A first compound having an atom in an oxidized state is reacted with a bis(trimethylsilyl) six-membered ring system or related compound to form a second compound having the atom in a reduced state relative to the first compound. The atom in an oxidized state is selected from the group consisting of Groups 2-12 of the Periodic Table, the lanthanides, As, Sb, Bi, Te, Si, Ge, Sn, and Al.

30 Claims, 73 Drawing Sheets

(51) Int. Cl.
*C01G 3/05* (2006.01)
*C23C 16/455* (2006.01)

(56) References Cited

U.S. PATENT DOCUMENTS

| | | | |
|---|---|---|---|
| 6,020,511 | A | 2/2000 | Vaartstra et al. |
| 6,475,276 | B1 * | 11/2002 | Elers et al. ............... 117/84 |
| 6,786,936 | B2 | 9/2004 | Vaartstra |
| 7,632,351 | B2 | 12/2009 | Thompson |
| 2001/0009695 | A1 | 7/2001 | Saanila et al. |
| 2002/0013487 | A1 | 1/2002 | Norman et al. |
| 2002/0098346 | A1 | 7/2002 | Yitzchaik |
| 2005/0097991 | A1 | 5/2005 | Sanjurjo et al. |
| 2005/0186342 | A1 | 8/2005 | Sager et al. |
| 2006/0134331 | A1 | 6/2006 | Thompson |
| 2006/0157863 | A1 | 7/2006 | Marsh |
| 2009/0114874 | A1 | 5/2009 | Norman et al. |
| 2010/0104755 | A1 | 4/2010 | Dussarrat et al. |
| 2010/0181566 | A1 | 7/2010 | Lee |
| 2012/0058270 | A1 | 3/2012 | Winter et al. |
| 2012/0231579 | A1 | 9/2012 | Quick et al. |
| 2013/0115768 | A1 | 5/2013 | Pore et al. |
| 2013/0251903 | A1 | 9/2013 | Han |

OTHER PUBLICATIONS

International Search Report, dated Oct. 27, 2014 in PCT/US2014/044669 filed Jun. 27, 2014, 3 pgs.
Authors et al.: Disclosed Anonymously, IP.com Prior Art Database Technical Disclosure, IP.com No. IPCOM000173198D, Jul. 25, 2008.
Non-Final Office Action mailed Aug. 27, 2014 in U.S. Appl. No. 13/818,154, filed Feb. 21, 2013, 9 pgs.
Bart, S.C. et al., "Low-Valent α-Diimine Iron Complexes for Catalytic Olefin Hydrogenation," Organometallics 2005, v. 24, pp. 5518-5527.
d'Alnoncourt, R.N. et al., "The preparation of Cu/Al2O3 catalysts via CVD in a fluidized-bed reactor," Surface and Coatings Technology 201, pp. 9035-9904, 2007.
Dieck, H.T. et al., "Reaktionen von Bis(dizadien)eisen(O)," Komplexen. Chem. Ber., 120, pp. 1943-1950, Oct. 2002 (English Abstract).
Gardiner, M.G. et al., "Paramagnetic Bis(1,4-di-tert-butyl-1,4-diazabutadiene) Adducts of Lithium, Magnesium, and Zinc," Inorg. Chem. 1994, 33, pp. 2456-2461.
Ghosh, M. et al., "(α-Diimine)chromium Complexes: Molecular and Electronic Structures; a Combined Experimental and Density Functional Theoretical Study," Inorganic Chem., v. 47, n. 13, (2008), pp. 5963-5970.
Ghosh, M. et al., "A structural, spectroscopic and computational study of the molecular and electronic structure of a [bis(α-diiminato)manganese(II)] π radical complex," Dalton Trans., 2008, pp. 5149-5151.
Gong, Y. et al., "The intra-annular acylamide chelate-coordinated compound: The keto-tautomer of metal (II)-milrinone complex," J. of Molecular Structure 875 (2008), pp. 113-120.
Hassaan, "Mixed ligand complexes of bis(s-methyl-n-arylidene hydrazine carbodithioate) nickel (ii) chelates with some amino acids and nitrogenous heterocycles," J. of Islamic Academy [online] retrieved from http://www.medicaljournal-las.org/3_4Hassaan.pdf on Jul. 1, 2010, pp. 269-272.
International Search Report dated Jul. 1, 2010 from corresponding PCT/US2010/035080 filed May 17, 2010, 2 pgs.
International Search Report for PCT/US2011/048792, Completed by the Korean Patent Office on Feb. 23, 2012, 3 pp.
International Search Report dated Aug. 17, 2012 from corresponding PCT/US12/040892 filed Jun. 5, 2012, pgs.
Kaltsoyannis, N., "Covalency in metal complexes of 1,4-diazabutadiene (dab). A density functional investigation of the electronic structures of [M(dab)2] (M = Li, Ga or Co) and [Th(NH3)NH2)3(dab)]," J. Chem. Soc., Dalton Trans., 1996, pp. 1583-1589.
Kalutarage, L.C. et al., "Low-Temperature Atomic Layer Deposition of Copper Films Using Borane Dimethylamine as the Reducing Co-reagent," Chem. Mater. 2014, 26, pp. 3731-3738.
Kalutarage, L.C. et al., "Synthesis, Structure, and Solution Reduction Reactions of Volatile and Thermally Stable Mid to Late First Row Transition Metal Complexes Containing Hydrazonate Ligands," Inorg. Chem. 2013, v. 52, pp. 5385-5394.
Kalutarage, L.C. et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films," J. Am. Chem. Soc. 2013, 135, pp. 12588-12591.
Karunarathne, M.C. et al., "Exceptional thermal stability and high volatility in mid to late first row transition metal complexes containing carboyhydrazide ligands," Polyhedron 52 (2013), pp. 820-080.
Khusniyarov, M. M. et al., "Reversible Electron Transfer Coupled to Spin Crossover in an Iron Coordination Salt in the Solid State," Angew. Chem. Int. Ed. 2008, 47, pp. 1228-1231.
Khusniyarov, M.M. et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino) acenaphthene (BIAN)," Eur. J. Inorg. Chem. 2006, pp. 2985-2996.
Khusniyarov, M.M. et al., "Tuning the Oxidation Level, the Spin State, and the Degree of Electron Delocalization in Hom- and Heteroleptic Bis(α-diimine)iron Complexes," J. Am. Chem. Soc. 2009, v. 131, pp. 1208-1221.
Knisley, T.J. et al., "Low Temperature Growth of High Purity, Low Resistivity Copper Films by Atomic Layer Deposition," Chem. Mater. 2011, v. 23, pp. 4417-4419.
Knisley, T.J. et al., "Volatility and High Thermal Stability in Mid- to Late-First-Row Transition-Metal Dizazdienyl Complexes," Organometallics 2011, v. 30, pp. 5010-5017.
Kreisel, K.A. et al., "Synthesis, Characterization, and Electronic Structure of Diimine Complexes of Chromium," Inorganic Chem., v. 74, n. 12, (2008), pp. 5293-5303.
Kreisel, K.A. et al., "The Shortest Metal-Metal Bond Yet: Molecular and Electronic Structure of a Dinuclear Chromium Diazadiene Complex," J. Am. Chem. Soc. 2007, v. 129, pp. 14162-14163.
Lim, B.S. et al., "Atomic layer deposition of transition metals," Nature Materials, v. 2, Nov. 2003, pp. 749-754.
Mac-Leod-Carey, D.A. et al., "Bix[2-(2,4-dioxopentan-3-ylidene-kO)-1-(4-methoxy-phenyl)hydrazinato-kN1] copper(II)," Acta Cryst. 2007, E63, pp. m670-m672.
Marten, J. et al., "3-(Arylhydrazono)pentane-2,4-diones and their Complexes with Copper(II) and Nickel(II)—Synthesis and Crystal Structures," Z. Anorg. Allg. Chem. 2005, v. 631, pp. 869-877.
Muresan, N. et al., "Bis(α-diimine)iron Complexes: Electronic Structure Determination by Spectroscopy and Broken Symmetry Density Functional Theoretical Calculations," Inorganic Chem., v. 47, n. 11, (2008), pp. 4579-4590.
Muresan, N. et al., "Bis(α-diimine)nickel Complexes: Molecular and Electronic Structure of Three Members of the Electron-Transfer Series [Ni(L)2]z (z=0, 1+, 2+) (L=2-Phenyl-1,4-bis(isopropyl)-1,4-diazabutadiene). A Combined Experimental and Theoretical Study," Inorganic Chem., v. 46, n. 13, (2007) pp. 5327-5337.
Muresan, N. et al., "Neutral (bis(1,4-diaza-1,3-butadiene)nickel complexes and their corresponding monocations: molecular and electronic structures. A combined experimental and density functional theoretical study," Dalton Trans., 2007, pp. 4390-4398.
Nassimbeni, L. et al., "The Crystal and Molecular Structure of the Bis-(5-ethyl-5-isoamylbarbiturato)bis(imidazole) Complex of Nickel(II)," Acta Cryst. (1974), B30, p. 2593-2602.
Pangani et al., "Coordination compounds of lanthanides with acetylhydrazine," Inorganica Chimca Acta, v. 94, issues 1-3, Feb. 1984, Abstract p. 79.
Pettinari, C. et al, "Copper and silver derivatives of scorpionates and related ligands," Polyhedron 23 (2004), pp. 451-469.

(56) References Cited

OTHER PUBLICATIONS

Popoff, N. et al., "Shifting from Ziegler-Natta to Phillips-Type Catalyst? A Simple and Safe Access to Reduced Titanium Systems for Ethylene Polymerization," Macromol. Rapid Commun. 2011, 32, pp. 1921-1924.

Rijnberg et al., "A Homologous Series of Homoleptic Zinc Bis(1,4-di-tert-butyl-1,4-diaza-1,3-butadiene) Complexes: Kx(Zn(t-BuNCHCHN-t-Bu)2 and (Zn(t-BuNCHCHN-t-Bu)2))(Otf)x (x=1,2)," Inorg. Chem. 1998, v. 37, pp. 56-63.

Robinson, M.A. et al., "Complexes Derived from Strong Field Ligands. XVII. Electronic Spectra of Octahedral Nickel(II) Complexes with Ligands of the α-Diimine and Closely Related Classes," Inorganic Chem., v. 2, n. 6, (1963), pp. 1178-1181.

Saito, T. et al., "1,4-Bis(trimethylsilyl)-,4-diaza-2,5-cyclohexadienes as Strong Salt-Free Reductants for Generating Low-Valent Early Transition Metals with Electron-Donating Ligands," J. Am. Chem. Soc. 2014, 136, pp. 5161-5170.

Svoboda, M. et al., "Bis(diazadien)metal(O)-Komplexe, III [1]1 Nickel(O)-bis(chelate) mit aliphatischen N-Substituenten," Z. Naturforsch. 86b, (1981), pp. 814-822—English Abstract.

Thompson, R.K. "Amidate Complexes of the Group 4 Metals," Synthesis, Reactivity, and Hydroaminiation Catalysis Thesis, The University of British Columbia. http://hdl.handle.net/2429/1344. Available online Nov. 8, 2008, pp. 1-120.

Tsurugi, H. et al., "Carbon Radical Generation by D0 Tantalum Complexes with α-Diimine Ligands through Ligand-Centered Redox Processes," J. Am. Chem. Soc. 2011, 133, pp. 18673-18683.

Tsurugi, H. et al., "Salt-Free Reducing Reagent of Bis(trimethylsilyl)cyclohexadiene Mediates Multielectron Reduction of Chloride Complexes of W(VI) and W(IV)," J. Am. Chem. Soc. 2013, 135, pp. 5986-5989.

Vidjayacoumar et al., "Investigation of AlMe3, BEt3, and ZnEt2 as Co-Reagents for Low Temperature Copper Metal ALD/Pulsed-CVD," Chem. Mater. 2010, v. 22, pp. 4844-4853.

Yilmaz, F. et al., "Bis-(5,5'-diethylbarbiturato) Copper(II) and Cadmium(II Complexes with Ethylenediamine Synthesis Crystal Structures, Spectroscopic and Thermal Characterization of cis-[Cu(barb)2(en] and {[Cd(barb)2(μ-en)] -2H2O)n," Z. Anorg. Allg. Chem. 2005, v. 631, pp. 1536-1540.

Non-Final Office Action mailed Apr. 7, 2014 in U.S. Appl. No. 13/319,793 filed 100/10/2011, 7 pgs.

Non-Final Office Action mailed May 28, 2014 in U.S. Appl. No. 13/493,560 filed Jun. 11, 2012, 7 pgs.

Non-Final Office Action mailed Jan. 14, 2015 in U.S. Appl. No. 13/930,471, filed Jun. 28, 2013, 7 pgs.

Non-final Office Action mailed Mar. 23, 2015 in U.S. Appl. No. 13/818/154, filed Feb. 21, 2013, 10 pgs.

English Machine Translation of KR1020080120087 published Jun. 7, 2010, 31 pgs.

\* cited by examiner formic acid alkyl carboxylic acid oxalic acid dicarboxylic acids sulfonic acids

HX

Inorganic Acid phosphoric acid phosphorous acid $R^{20}$ = H, $C_1$-$C_8$alkyl, $C_6$-$C_{12}$aryl, $C_1$-$C_8$fluoroalkyl
X = $N_3^-$, $NO_3^-$, halide (e.g., Cl, F, Br)
o = an integer from 1 to 6.

BIS(TRIMETHYLSILYL) SIX-MEMBERED RING SYSTEMS AND RELATED COMPOUNDS AS REDUCING AGENTS FOR FORMING LAYERS ON A SUBSTRATE

CROSS-REFERENCE TO RELATED APPLICATIONS

This application is a continuation-in-part of U.S. application Ser. No. 13/930,471 filed Jun. 28, 2013, and claims the benefit of U.S. provisional application Ser. No. 61/902,264 filed Nov. 10, 2013, and U.S. provisional application Ser. No. 61/974,115 filed Apr. 2, 2014, the disclosures of which are hereby incorporated in their entirety by reference herein.

FIELD OF THE INVENTION

In at least one aspect, the present invention is related to the formation of metal films from "metalorganic" precursors and a reducing agent.

BACKGROUND OF THE INVENTION

The growth of thin films is a central step in the fabrication of many functional materials and devices. While film growth efforts have been traditionally directed toward films greater than 100 nm, recent trends in several areas are calling for the growth of films ranging in thickness from a few atomic layers to tens of nanometers.

In the microelectronics arena, copper has replaced aluminum as the interconnect material in integrated circuits due to its lower resistivity and higher resistance to electromigration. Ultrathin (2-8 nm) manganese-silicon-oxygen layers have been proposed as replacements for existing nitride-based copper diffusion barrier layers in future devices. Since copper does not nucleate well on $SiO_2$ and other surfaces, it is difficult to deposit copper metal onto the surface features of microelectronic substrates. Accordingly, there has been considerable interest in the formation of seed layers of metals such as chromium, cobalt, and others which adhere better to substrates, and upon which copper films can be subsequently grown.

Atomic layer deposition (ALD) is a thin film deposition technique that addresses many of the current technological demands. ALD affords inherently conformal coverage and sub-nanometer film thickness control due to its self-limited growth mechanism. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is unfortunately only a limited number of chemical precursors having the requisite thermal stability, reactivity, and vapor pressure for ALD.

Accordingly, there is a need for improved methods and reagents for depositing thin films by atomic layer deposition.

SUMMARY OF THE INVENTION

The present invention solves one or more problems of the prior art by providing, in at least one embodiment, a method of reducing a compound having an atom in an oxidized state. The method includes a step of reacting a first compound having an atom in an oxidized state with a reducing agent to form a second compound having the atom in a reduced state relative to the first compound. The atom in an oxidized state is selected from the group consisting of Groups 2-12 of the Periodic Table, the lanthanides, As, Sb, Bi, Te, Si, Ge, Sn, and Al. The reducing agent is selected from the group consisting of compounds described by formulae IA and IB:

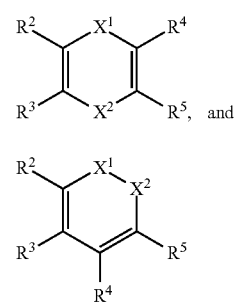

wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$; and
$R^1, R^{1'}, R^{1''}, R^2, R^3, R^4, R^5, R^6$, and $R^7$ are each independently H, $C_{1-10}$ alkyl, $C_{6-14}$ aryl, or $C_{4-14}$ heteroaryl.

In another embodiment, a method of reducing a compound having an atom in an oxidized state using gas phase reactants is provided. The method includes a step of providing a vapor of first compound. The atom in an oxidized state is selected from the group consisting of Groups 2-12 of the Periodic Table, the lanthanides, As, Sb, Bi, Te, Si, Ge, Sn, and Al. The method also includes a step of providing a vapor of a reducing agent. The reducing agent is selected from the group consisting of compounds described by formulae IA and IB:

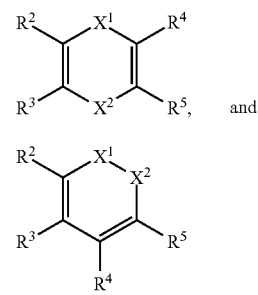

wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$; and
$R^1, R^{1'}, R^{1''}, R^2, R^3, R^4, R^5, R^6$, and $R^7$ are each independently H, $C_{1-10}$ alkyl, $C_{6-14}$ aryl, or $C_{4-14}$ heteroaryl. The vapor of the first compound and the vapor of the reducing agent are reacted to form to a second compound having the atom in a reduced state relative to the first compound.

In another embodiment, a method of forming a layer by an ALD process is provided. The method includes a step of contacting a substrate with a vapor of a first compound having an atom in an oxidized state to form a first modified surface. The atom in an oxidized state is selected from the group consisting of Groups 2-12 of the Periodic Table, the lanthanides, As, Sb, Bi, Te, Si, Ge, Sn, and Al. The first modified surface is optionally contacted with an acid for a second predetermined pulse time to form a second modified surface. The first modified surface or the second modified surface is contacted with a reducing agent for a third predetermined pulse time to form the layer on the substrate. The reducing agent is selected from the group consisting of:

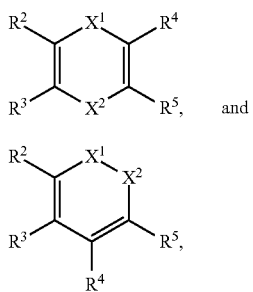

wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$; and
$R^1, R^{1'}, R^{1''}, R^2, R^3, R^4, R^5, R^6$, and $R^7$ are each independently H, $C_{1-10}$ alkyl, $C_{6-14}$ aryl, or $C_{4-14}$ heteroaryl.

In another embodiment, a method for forming a metal is provided. The method includes a step of contacting a metal-containing compound having at least one diazabutadiene ligand, the metal-containing compound having formula III or IV:

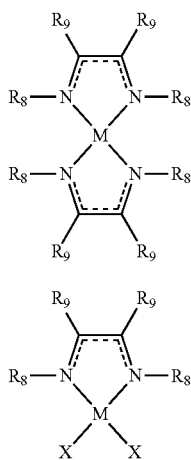

with an activating compound, the activating compound being an acid or a diketone at a sufficient temperature to form a metal film, wherein:
M is a transition metal selected from groups 3-10 of the periodic table, Ru, Pd, Pt, Rh, Ir, Mg, Al, Sn, or Sb;
$R_8$ is $C_1$-$C_{12}$ alkyl, amino (i.e., —$NH_2$), or $C_6$-$C_{18}$ aryl;
$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino; and
X is Cl, Br, or I.

In another embodiment, a method for depositing a thin metal film on a surface of a substrate is provided. The method includes a step of contacting the substrate with a vapor of a metal-containing compound having formula III or IV to form a modified surface on the substrate:

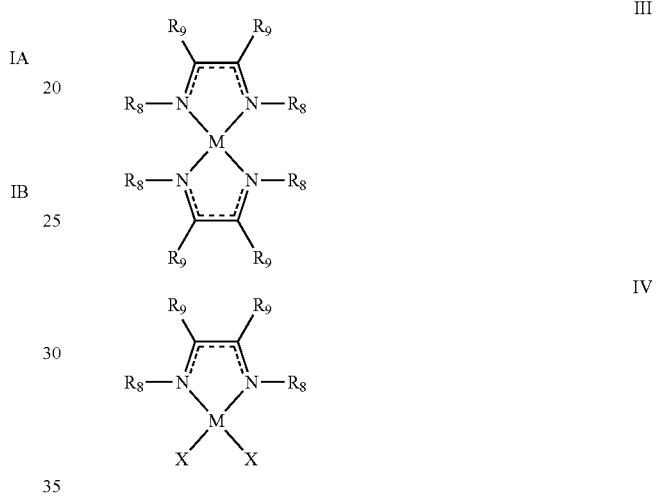

wherein:
M is a transition metal selected from groups 3-10 of the periodic table, Ru, Pd, Pt, Rh, Ir, Mg, Al, Sn, or Sb;
$R_8$ is $C_1$-$C_{12}$ alkyl, amino (i.e., —$NH_2$), or $C_6$-$C_{18}$ aryl;
$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino; and
X is Cl, Br, or I. The modified surface is then contacted with a vapor of an activating compound to form at least a portion of the thin film on the surface of the substrate. Characteristically, the activating compound is an acid or a diketone at a sufficient temperature to form a metal film.

In another embodiment, a method for depositing a thin metal film on a surface of a substrate is provided. The method includes a step of contacting the substrate with a vapor of a metal-containing compound having formula III or IV to form a first modified surface on the substrate:

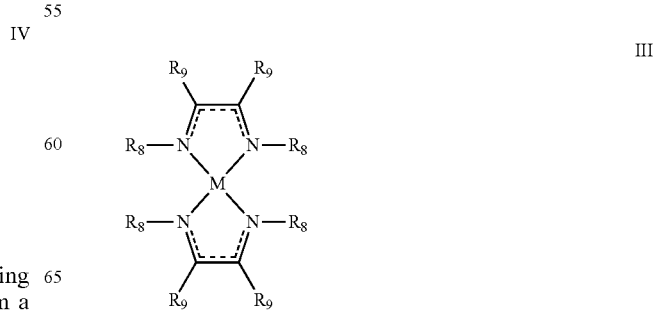

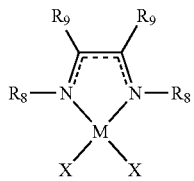

wherein:

M is a transition metal selected from groups 3-10 of the periodic table, Ru, Pd, Pt, Rh, Ir, Mg, Al, Sn, or Sb;

$R_8$ is $C_1$-$C_{12}$ alkyl, amino (i.e., —$NH_2$), or $C_6$-$C_{18}$ aryl;

$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino; and X is Cl, Br, or I. The first modified surface is then contacted with a vapor of an activating compound to form a second modified surface. Characteristically, the activating compound is an acid or a diketone. The second modified surface is then contacted with a reducing agent having formula IA or IB to form at least a portion of a metal film on the substrate.

BRIEF DESCRIPTION OF THE DRAWINGS

Exemplary embodiments of the present invention will become more fully understood from the detailed description and the accompanying drawings, wherein.

DESCRIPTION OF THE INVENTION

Figure 1:
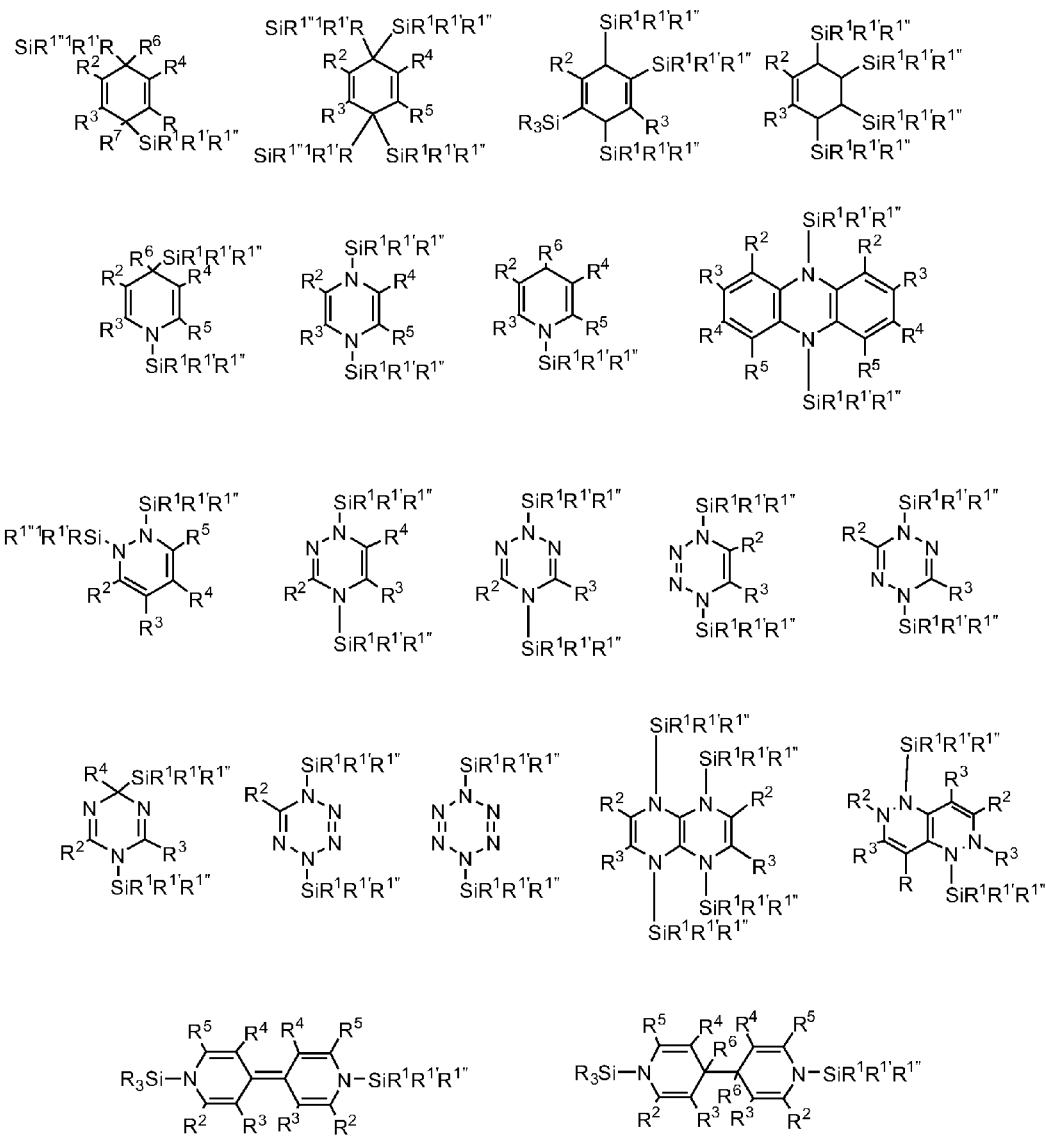
FIG. 1 provides additional examples of reducing agents encompassed by the present invention.

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; "R" groups include H, $C_{1-10}$ alkyl, $C_{2-10}$ alkenyl, $C_{6-14}$ aryl (e.g., phenyl, halo, or $C_{4-14}$ heteroaryl; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Abbreviations

"ALD" is atomic layer deposition.
"CVD is chemical vapor deposition.
"RT" means "room temperature."
"s" means "seconds."
"THF" means "tetrahydrofuran."
"DME" means "1,2-dimethoxyethane."
"CHD" means 1,4-bis(trimethylsilyl)-2-methyl-1,4-cyclohexadiene.
"DHP" means 1,4-bis(trimethylsilyl)-1,4-dihydropyrazine.
"dmap" means "4-Dimethylaminopyridine."
"dad" means diazadiene.
"dad$^{tBu2}$" means "1,4-di-tert-butyldiazadiene."
"XPS" means "X-ray photoelectron spectroscopy."
"SEM" means "scanning electron microscopy."
"XRD" means "X-ray diffraction."
"acac" is acetylacetonate.
"Cp" is cyclopentadienyl.
"dmap" is 1-dimethylamino-2-methyl-2-propoxy.
"en" is ethylene diamine.
"Et" is ethyl.
"EtCp" is ethylcyclopentadienyl.
"Et$_2$amd" is N,N'-diethylacetamidinate.
"Et$_2$fmd" is N,N'-diethylformamidinate.
"hfac" is 1,1,1,5,5,5-hexafluoro-acetylacetonate.
"iPr$_2$amd" is N,N'-diisopropylacetamidinate.
"iPr$_2$fmd" is N,N'-diisopropylformamidinate.
"iPrCp" is isopropylcyclopentadienyl.
"Me" is methyl.
"Me$_2$amd" is N,N'-dimethylacetamidinate.
"Me$_2$fmd" is N,N'-dimethylformamidinate.
"Mes" is 2,4,6-Me$_3$C$_6$H$_2$ or mesityl.
"MeCp" is methylcyclopentadienyl.
"Me$_5$Cp" is pentamethylcyclopentadienyl.
"Me$_2$fmd" is N,N'-dimethylformamidinate.
"Me$_2$bmd" is N—N'-dimethylbutyramidinate.
"Me$_2$pmd" is N,N'-dimethylpropionamidinate.
"mmp" is 1-methoxy-2-methyl-2-propoxy.
"OtPe" is tert-pentoxy.
"od" is octane-2 4-dionate.
"OiPr" is isopropoxy.
"OtBu" is tert-butoxy.
"OEt" is ethoxy.
"tBu$_2$amd" is N,N'-di-tert-butylacetamidinate.
"tBuEtamd" is N-tert-butyl-N-ethylacetamidinate.
"tBuEtpmd" is N-tert-butyl-N'-ethyl-propionamidinate.
"tBuEtbmd" is N-tert-butyl-N'-ethylbutyramidinate.
"thd" is 2,2,6,6-tetramethyl-heptane-3,5-dionate.
"TEM" is transmission electron microscopy.
"PXRD" is powder X-ray diffraction.
"EDS" is Energy-dispersive X-ray spectroscopy.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials.

In an embodiment, a method of reducing a compound having an atom in an oxidized state is provided. The method is particularly suited for forming metal-containing layers (e.g., metal layers) by ALD and by chemical vapor deposition (CVD). The method includes a step of reacting a first compound having an atom in an oxidized state with a reducing agent to form a second compound having the atom in a reduced state relative to the first compound. The atom in an oxidized state is selected from the group consisting of Groups 2-12 of the Periodic Table, the lanthanides, As, Sb, Bi, Te, Si, Ge, Sn, and Al. In a refinement, the atom in an oxidized state includes atoms from this group having a standard electrode potential greater than −2.4 V relative to a reference electrode potential (e.g., standard hydrogen electrode or a standard Ag/AgNO$_3$ electrode). In particular, such atoms are selected from the group consisting of Groups 3-12 of the Periodic Table, the lanthanides, As, Sb, Bi, Te, Si, Ge, Sn, and Al. In a variation, M is a transition metal. Examples of useful transition metals for M include, but are not limited to, Cu, Ni, Co, Cr, Mn, Fe, W, Mo, Ti, Zr, Hf, Rf, V, Nb, Ta, Re, Ru, Rh, Ir, Pd, Pt, and Au. Particularly useful examples for M include, but are not limited to, Cr(II), Mn(II), Fe(II), Co(II), and Ni(II). In a refinement, M is a transition metal selected from groups 3-7 of the periodic table. The compounds with an atom in an oxidized state include an atom in an oxidation state greater than 0 (e.g., 1, 2, 3, 4, 5, or 6). Typically, the compounds with an atom in an oxidized state are metal-containing compounds. Useful metal-containing compounds are organometallic compounds and metal halides with vapor pressures sufficient for ALD or CVD processes. In a refinement, the compounds containing an atom in an oxidized state have vapor pressures of at least 0.01 torr at 100° C. In a further refinement, the compounds containing an atom in an oxidized state have vapor pressures of at least 0.05 torr to about 700 torr at 100°

C. Characteristically, the reducing agent is selected from the group consisting of compounds described by formulae IA and IB:

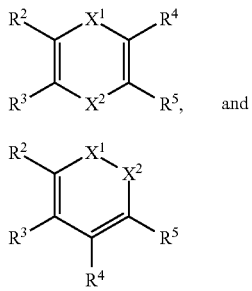

wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$;
$R^1, R^{1'}, R^{1''}, R^2, R^3, R^4, R^5, R^6$, and $R^7$ are each independently H, $C_{1-10}$ alkyl, $C_{6-14}$ aryl, or $C_{4-14}$ heteroaryl.

In a variation of compounds having formulae IA and IB, the reducing agent is selected from the group consisting of:

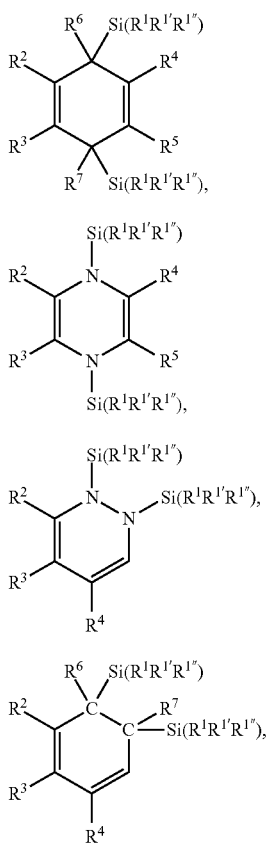

and combinations thereof. The compound described by formula IIB is found to be particularly useful in forming metal-containing films. Particularly useful examples of the reducing agent are 1,4-bis(trimethylsilyl)-2-methyl-1,4-cyclohexadiene and 1,4-bis(trimethylsilyl)-1,4-dihydropyrazine.

With reference to FIG. 1, additional examples of reducing agents are provided. In these examples, $R^1, R^{1'}, R^{1''}, R^2, R^3,$ $R^4, R^5, R^6,$ and $R^7$ are each independently H, $C_{1-10}$ alkyl, $C_{6-14}$ aryl, or $C_{4-14}$ heteroaryl. In a refinement of the compounds described by formulae IA, IB, IIA, IIB, IIC, IID and the compounds of FIG. 1, $R^1, R^{1'}, R^{1''}$ are each independently $C_{1-10}$ alkyl; $R^2, R^3, R^4, R^5$ are each independently H or $C_{1-10}$ alkyl; and $R^6$, and $R^7$ are H. In another refinement, $R^1, R^{1'}, R^{1''}$ are each independently hydrogen, methyl, ethyl, n-propyl, isopropyl, n-butyl, sec-butyl, isobutyl, t-butyl, or phenyl. In still another refinement, $R^2, R^3, R^4,$ and $R^5$ are each independently hydrogen, methyl, ethyl, n-propyl, isopropyl, n-butyl, sec-butyl, isobutyl, t-butyl, or phenyl. In yet another refinement, $R^6, R^7$ are each independently hydrogen, methyl, ethyl, n-propyl, isopropyl, n-butyl, sec-butyl, isobutyl, t-butyl, or phenyl. In a particularly useful example, $R^1, R^{1'}, R^{1''}$, are methyl; $R^6, R^7$ are hydrogen; and $R^2, R^3, R^4,$ and $R^5$ are hydrogen or methyl. In another useful example, $R^1, R^{1'}, R^{1''}$ are methyl; $R^6, R^7$ are hydrogen; $R^2, R^3, R^4,$ and $R^5$ are hydrogen or methyl.

As set forth above, the first compound includes an atom in an oxidized state selected from Groups 2-12 of the Periodic Table, the lanthanides, As, Sb, Bi, Te, Si, Ge, Sn, and Al. In particular, the atom in an oxidized state is in an oxidation state of +1, +2, +3, +4, +5, or +6. In a refinement, the atom in an oxidized state is a transition metal. Particularly useful examples of the atom in an oxidized state include, but are not limited to, Cu, Cr, Mn, Fe, Co, Ti, or Ni.

Although the present invention is not limited by the type of the first compound that includes an atom in an oxidized state, compounds of the following structures are particularly useful:

$$ML_n$$

$$ML_nY_m$$

wherein M is an atom selected from Groups 2 to 12 of the Periodic Table, As, Sb, Bi, Se, and Te; L is an anionic ligand; n is the number of anionic ligands; Y is a neutral ligand and m is the number of neutral ligands. Examples for Y include, but are not limited to, 2,2'-Bipyridine, $H_2O$, $CH_3CN$, $C_5H_5N$ (pyridine), CO, ethylenediamine, 1,10-phenanthroline, $PPh_3$, $NH_3$, and the like. Typically, n will be of sufficient number to neutralize any charge on M. In a refinement, n is from 1 to 6 and m is from 1 to 5. Examples for L include optionally-substituted cyclopentadienyl, optionally-substituted β-diketonates, optionally-substituted amidinates, optionally-substituted guanidinates, optionally-substituted β-aminoalkoxides, optionally-substituted allyls, and optionally-substituted tris(pyrazolyl)borates.

In a variation, the first compound having an atom in an oxidized state is diazadiene compound described by the following formula:

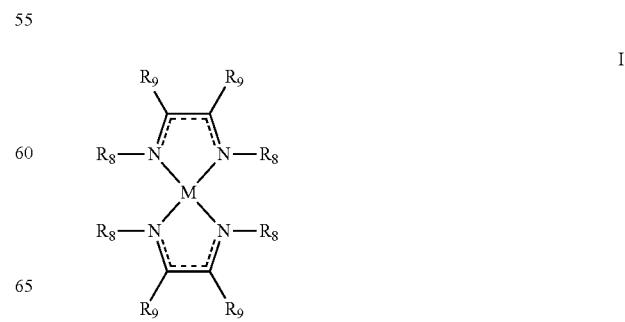

-continued

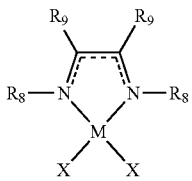

with an activating compound. The activating compound is an acid or a diketone at a sufficient temperature to form a metal film,
wherein:
M is a transition metal selected from Groups 3-10 of the Periodic Table, Ru, Pd, Pt, Rh, and Ir;
In a refinement, M are the atoms in an oxidized state as set forth above;
$R_8$ is $C_1$-$C_{12}$ alkyl, amino (i.e., —$NH_2$), or $C_6$-$C_{18}$ aryl;
$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino and
X is Cl, Br, or I. In a refinement, M is Mg, Al, Ti, V, Cr, Mn, Fe, Co, Ni, Cu, Zn, Sn, or Sb. In another refinement, when the metal-containing compound has formula II, M is Cr, Mn, Fe, Ni, Co, Zn, Al, or Mg. In still another refinement, M is Mg, Al, Sn, or Sb. In a useful variation, the $C_{2-5}$ diketone is a 1,3-diketone. It should be appreciated that the reaction of the present embodiment can be in the gas or liquid phases. In other variations, the reaction is an ALD reaction as set forth below.

In another variation, the first compound having an atom in an oxidized state is described by the following formula:

$$M((NR_{10})_2)_n$$

wherein:
M is a metal selected from Groups 2 to 12 of the Periodic Table, As, Sb, Bi, Se, and Te or the subgroups for the atom in an oxidized state set forth above;
$R_{10}$ is $C_{1-6}$ alkyl, $Si(R_{11})_3$;
$R_{11}$ is $C_{1-6}$ alkyl, and
n is 2, 3, 4, 5, or 6.

In another variation, the first compound having an atom in an oxidized state is described by the following formula:

$$M(OR_{10})_n$$

wherein:
M is a metal selected from Groups 2 to 12 of the Periodic Table, As, Sb, Bi, Se, and Te or the subgroups for the atom in an oxidized state set forth above;
$R_{10}$ is $C_{1-6}$ alkyl; and
n is 2, 3, 4, 5, or 6.

In another variation, the first compound having an atom in an oxidized state is β-diketone compounds described by the following formula:

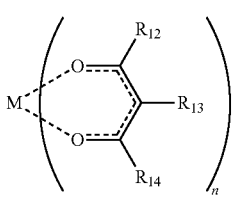

M is a metal selected from Groups 2 to 12 of the Periodic Table, As, Sb, Bi, Se, and Te or the subgroups for the atom in an oxidized state set forth above;

$R_{12}$, $R_{13}$, $R_{14}$ are independently H, $C_{1-10}$ alkyl, $C_{1-8}$ perfluoroalkyl, $CF_3$, $C_{1-10}$ polyether groups, and the like; and
n is 2, 3, 4, 5, or 6.

In another variation, the first compound having an atom in an oxidized state is amidinate compounds described by the following formula:

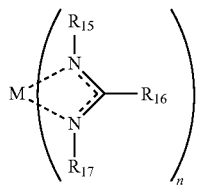

wherein:
M is a metal selected from Groups 2 to 12 of the Periodic Table, As, Sb, Bi, Se, and Te or the subgroups for the atom in an oxidized state set forth above;
$R_{15}$, $R_{16}$, $R_{17}$ are independently H, $C_{1-10}$ alkyl, $C_{1-8}$ perfluoroalkyl, $CF_3$, $C_{1-10}$ polyether groups, and the like; and
n is 2, 3, 4, 5, or 6.

Specific examples for the compounds including an atom in an oxidized state include, but are not limited to, $Ag_2(tBu_2$-$amd)_2$, $Al(CH_3)_3$, $Al(NMe_2)_3$, $Al_2(NMe_2)_6$, $Al_2(C_2H_5)_4(\mu$-$C_2H_5)_2$ $AlMe_2(OiPr)$, $Ba(thd)_2$, $Ca(tBu_2amd)_2$, $Ce(thd)_4$, $Co_2(CO)_6(C_2R_2)$, $Co(C_5H_5)_2$, $CpCo(CO)_2$, $CoCp(C_6Me_6)$, $Co(C_6Me_6)_2$, $CpCo(CO)_2$), $Co(acac)_2$, $Co(acac)_3$, $Co(iPr_2amd)$, $Co(thd)_3$, $Co(thd)$, $Co(tBuEtamd)_2$, $Co(tBuEtpmd)_2$, $CrCp_2$, $Cr(acac)_3$, $Cr(Et_2amd)_3$, $Cu_2(iPr_2amd)_2$, $Cu(hfac)_2$), $Cu(hfac)_2$, $Cu(thd)_2$, $Dy(thd)_3$, $Fe(iPr_2amd)_2$, $Er(tBu_2amd)_3$, $Fe(tBuEtamd)_2$, $Fe(thd)_3$, $Ga(Et_2amd)_3$, $Gd(iPr_2amd)_3$, $Gd(thd)_3$, $HfCl_4$, $Hf(OtBu)_4$, $Hf(mmp)_4$, $Hf(Me_2fmd)_4$, $Hf(Me_2$-$pmd)_4$, $Hf(Me_2bmd)_4$, $Ho(thd)_3$, $Ir(acac)_3$, $La(thd)_3$, $La[N(SiMe_3)_2]_3$, $La(iPr_2fmd)_3$, $La(tBu_2fmd)_3$, $Lu(Et_2fmd)_3$, $Lu(Et_2amd)_3$, $Mg(tBu_2amd)_2$, $Mg(iPr_2amd)_2$, $Mn(thd)_3$, $Mn(EtCP)_2$, $Mo(Mes)(CO)_3$, $Nb(OEt)_5$, $Ni(dmamp)_2$, $Ni(tBu_2amd)$, $Pb(OtBu)_2$, $Pr(iPr_2amd)_3$, $Si(OEt)_4$, $Si(OtBu)_3OH$, $Si(OtPe)_3OH$, $Ta(OEt)_5$, $Ti(iPr_2amd)_3$, $Ti(OMe)_4$, $Ti(OEt)_4$, $Ti(OiPr)_4$, $Nd(thd)_3$, $Ni(acac)_2$, $Ni(thd)_2$, $Pb(thd)$, $Er(thd)_3$, $Eu(thd)_3$, $Fe(acac)_3$, $Ru(thd)_3$, $Ru(od)_3$, $Ru(tBu_2amd)_2(CO)_2$, $Sc(thd)_3$, $Sc(Et_2amd)_3$, $Sr(tBu_2amd)_2$, $Sm(thd)_3$, $Sr(thd)_2$, $Sr(methd)_2$, $Tm(thd)_3$, $Y(thd)_3$ $Mg(thd)_2$, $Hf(NMe_2)_4$, $Hf(NEtMe)_4$, $Hf(NEt_2)_4$, $Pr[N(SiMe_3)_2]_3$, $Sb(NMe_2)_3$, $Ru(EtCp)_2$, $TiCl_4$, $NiCp_2$, $Sr(Me_5 Cp)_2$, $Ta(NMe_2)_5$, $Ta(NEt_2)_5$, $Ta(NtBu)(NEt_2)_3$, $Ti(NMe_2)_4$, $Ti(NEtMe)_4$, $V(Et_2amd)_3$, $V(iPr_2amd)_3$, $WF_6$, $W(NtBu)_2(NMe_2)_2$, $Y(iPr2amd)_3$, $Zn[N(SiMe_3)_2]_2$, $Zn(CH_2CH_3)_2$, $Zn(iPr_2amd)_3$, $Zn(iPr_2amd)_2$, $Zr(Me_2amd)_4$, $Zr(Me_2fmd)_4$, $Zr(Me_2bmd)_4$, $Zr(Me_2pmd)_4$, $Zr(NMe_2)_4$, $Zr(NEtMe)_4$, $Zr(NEt_2)_4$, $ZrCp_2Me_2$, $Al(OR)_3$, $SiH_2(NR_2)_2$, $SiH(NR_2)_3$, $Si_2Cl_6$, $Si_3Cl_8$, $Ti(NMe_2)_4$, $Ti(NMeEt)_4$, $Ti(NEt_2)_4$, $CpTi(NMe_2)_3$, $(2$-$tBuallyl)Co(CO)_3$, where R is $C_{1-6}$ alkyl. Additional examples include, but are not limited to Cp and substituted versions of Ni, Co, Fe, Mn, Cr, Cu alkoxides with beta-amino groups, $TiBr_4$, $TiI_4$, $TiF_4$, halides and pseudohalides of Nb(V), Ta(V), Mo(IV), Mo(V), Mo(VI), W(IV), W(V), W(VI), Al(III), Si(IV), Ge(IV), Ge(II), Sn(II), Sn(IV), Sb(III), Sb(V), $Al(NMe_2)_3$, volatile Si(IV) compounds, volatile Si(IV) hydrides, volatile Ge(IV) compounds, volatile Ge(IV) hydrides, and halides of Se and Te.

In another refinement of the present embodiment, a method for forming a metal is provided. In this context, the metal is characterized as having metal atoms in the zero oxidation state. The present refinement can be carried out either in solution or in the vapor phase (e.g. ALD, CVD, etc) at temperatures from about 50 to 400° C. In another refinement, the metal deposition is carried out at temperatures from about 75 to 200° C.

In a further refinement, a method of forming a metal film by an ALD process is provided. The method comprises a deposition cycle which includes contacting the substrate with vapor of a first compound having an atom in an oxidized state as set forth above such that at least a portion of the vapor of the first compound adsorbs or reacts with a substrate surface to form a modified surface. The deposition cycle further includes contacting the modified surface with a vapor of the reducing agents set forth above to react and form at least a portion of the metal film. Typically, the first compound having an atom in an oxidized state is contacted with the reducing agent at a temperature from about 50 to 400° C. The present reaction is used in an ALD process as set forth below.

Figure 2A:
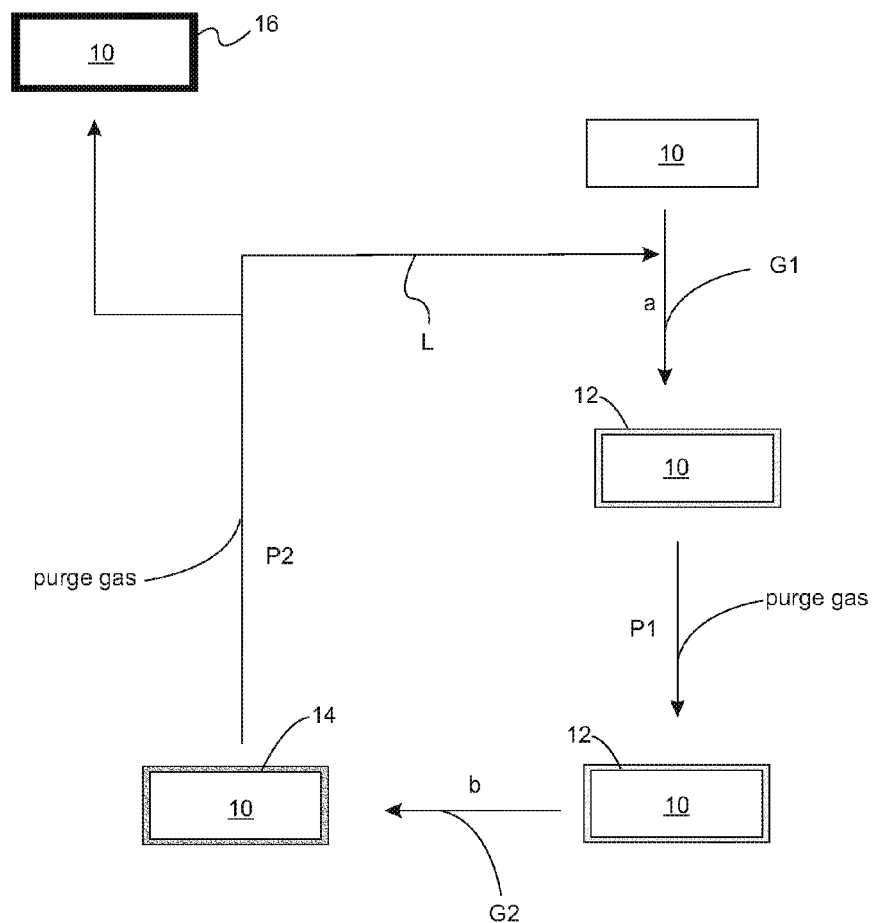
FIG. 2A is a schematic flowchart illustrating an ALD deposition process using the bis(trimethylsilyl) six-membered ring systems of an embodiment of the invention.

With reference to FIG. 2A, a method for forming a layer by an ALD process is schematically illustrated. In step a), substrate 10 is contacted with a vapor G1 of a first compound having an atom in an oxidized state to form a first modified surface 12. The atom in an oxidized state is selected from the group consisting Groups 2-12 of the Periodic Table, the lanthanides, As, Sb, Bi, Te, Si, Ge, Sn, and Al. In particular, the first compound is as set forth above. In step b) the first modified surface 12 is contacted with a reducing agent G2 for a predetermined pulse time to form layer 14 on the substrate 10. The details of the reducing agent are as set forth above. Purging steps P1 and P2 are performed after steps a) and b), respectively. Loop L indicates that steps a), P1), b), and P2) are repeated a plurality of times in order to build up a final layer 16 of predetermined thickness monolayer by monolayer. Additional details of this ALD process are set forth below.

Figure 2B:
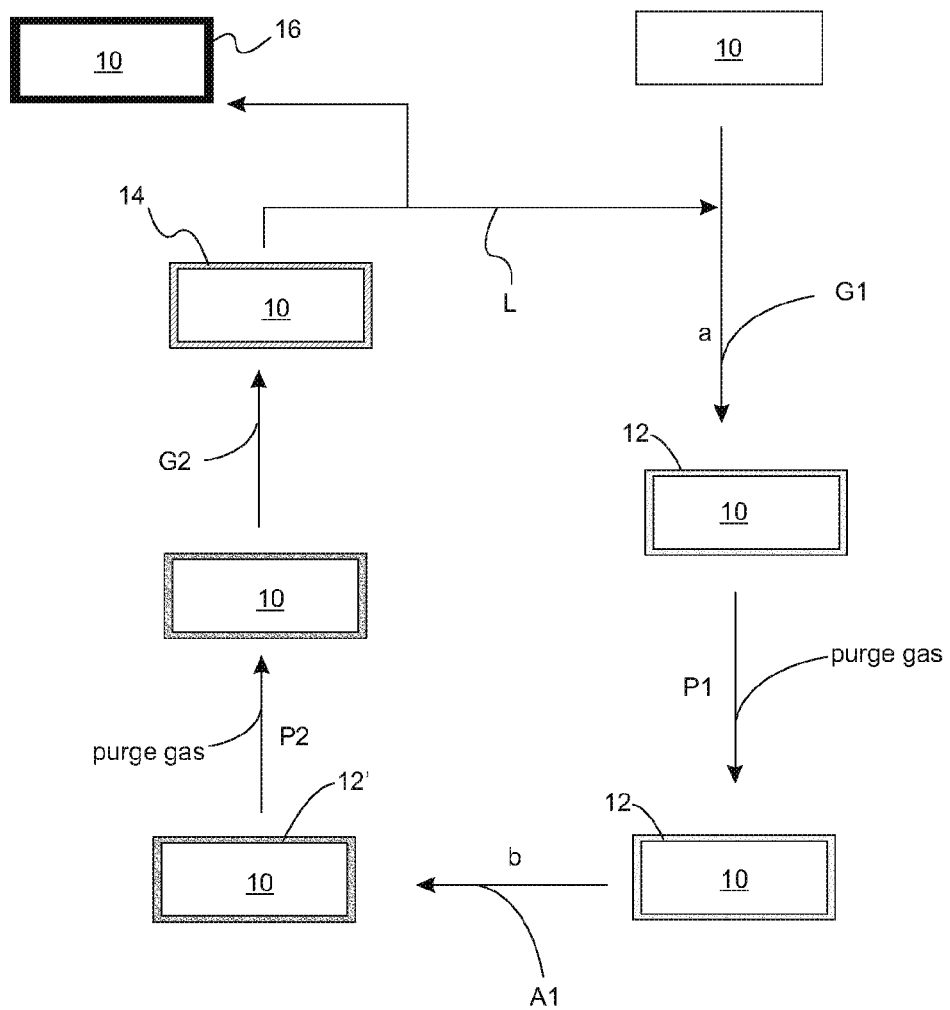
FIG. 2B is a schematic flowchart illustrating an ALD deposition process using the bis(trimethylsilyl) six-membered ring systems of an embodiment of the invention.

With reference to FIG. 2B, a method for forming a layer by an ALD process is schematically illustrated. In step a), substrate 10 is contacted with a vapor G1 of a first compound having an atom in an oxidized state to form a first modified surface 12. The atom in an oxidized state is selected from the group consisting of Groups 2-12 of the Periodic Table, the lanthanides, As, Sb, Bi, Te, Si, Ge, Sn, and Al In particular, the first compound is as set forth above. In step b), the first modified surface 12 is contacted with an acid Al for a second predetermined pulse time to form a second modified surface 12'. In step c), the second modified surface 12' is contacted with a reducing agent G2 for a third predetermined pulse time to form layer 14 on the substrate. Purging steps P1, P2, and P3 are performed after steps a), b), and c), respectively. Loop L indicates that steps a), P1), b), P2), c), and P3 are repeated a plurality of times in order to build up a final layer 16 of predetermined thickness monolayer by monolayer. The details of the reducing agent are as set forth above. Additional details of this ALD process are set forth below.

Figure 2C:
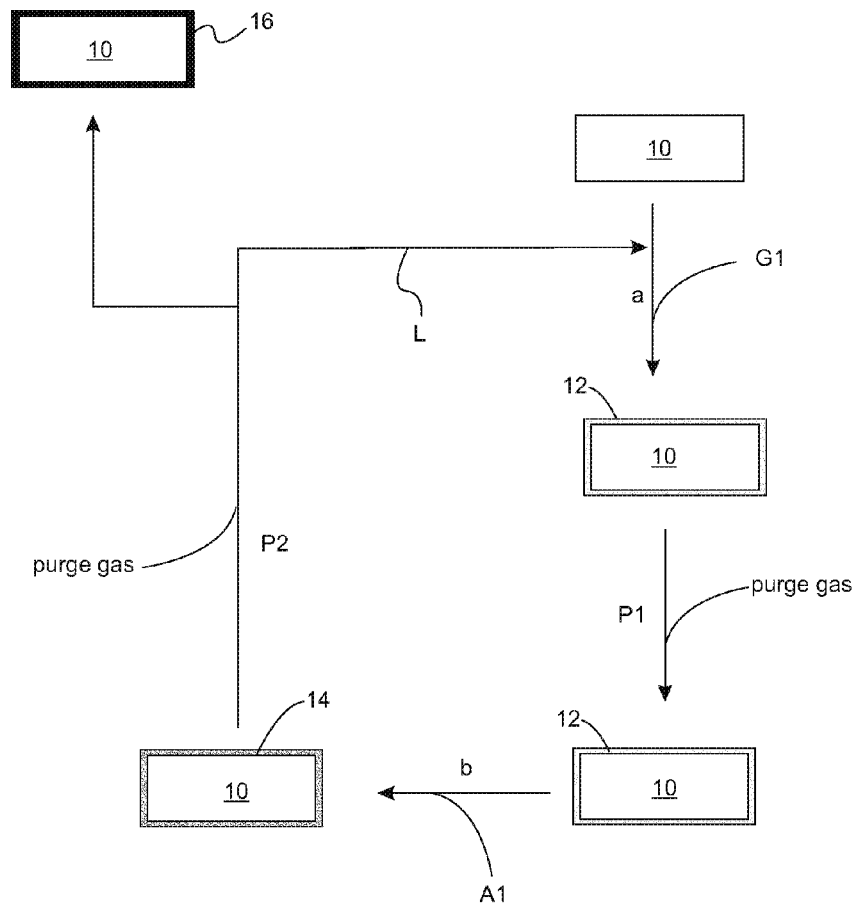
FIG. 2C is a schematic flowchart illustrating an ALD deposition process using the bis(trimethylsilyl) six-membered ring systems of an embodiment of the invention.
Figure 2D:
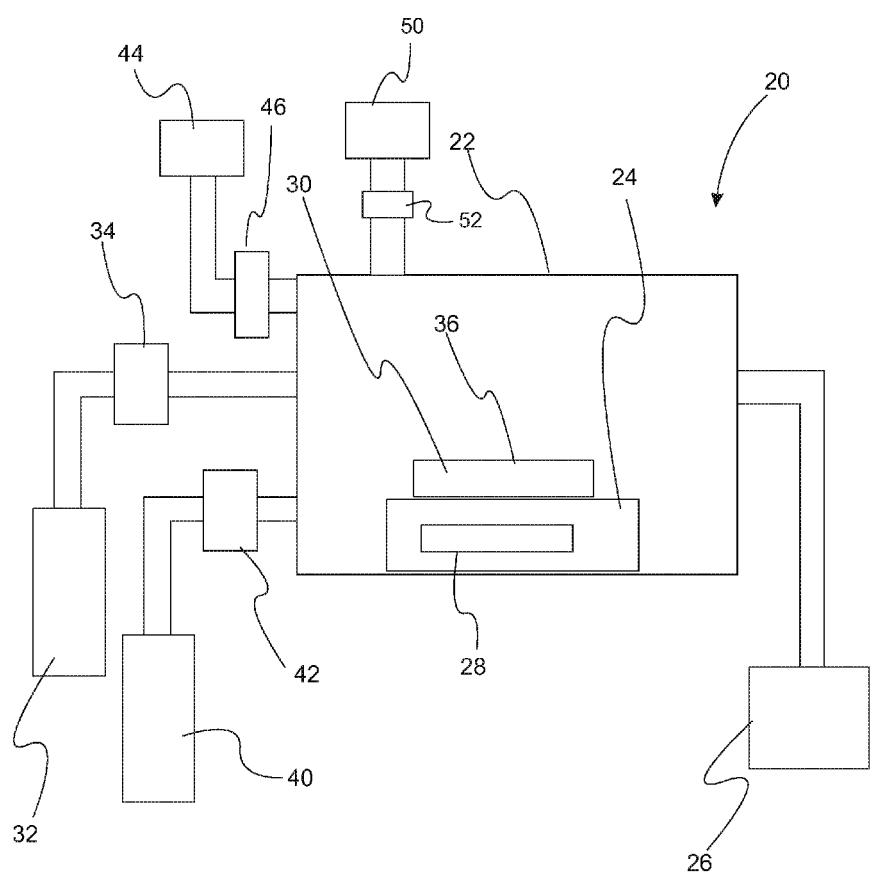
FIG. 2D is a schematic illustration of an ALD deposition system used in an embodiment of the present invention.

With reference to FIG. 2D, deposition system 20 includes reaction chamber 22, substrate holder 24, and vacuum pump 26. Typically, the substrate is heated via heater 28. The method has a deposition cycle comprising contacting substrate 30 with a vapor of the first compound having an atom in an oxidized state as set forth above. In particular, the vapor is introduced from precursor source 32 into reaction chamber 22 for a predetermined pulse time. The pulse time is controlled via control valve 34. At least a portion of the vapor of the first compound modifies (e.g, adsorbs or reacts with) substrate surface 36 to form a modified surface. The method further comprises contacting the modified surface with a vapor of the reducing agent as set forth above from source 40 for a predetermined pulse time controlled by valve 42.

In a variation of the present embodiment, the method further comprises removing at least a portion of the vapor of the first compound that is lingering in the gas phase (i.e., has not adsorbed or reacted with the substrate) from the vicinity of the substrate before introducing the vapor of the reducing agent and removing at least a portion of the vapor of the reducing agent from the vicinity of the substrate. The metal-containing compound and the reducing agent are removed in purging steps by introducing a purge gas from purge source 44 into reaction chamber 22 for a predetermined purge time. The purge time is controlled by control valve 46.

In another variation, the method further includes at least one additional deposition cycle comprising sequentially contacting the substrate with the vapor of the first compound and then the vapor of the reducing agent. In some refinements, the substrate is contacted for a plurality of additional deposition cycles. For example, the substrate may be contacted with from 1 to several thousand deposition cycles depending on the thickness of the film desired. In particular, the substrate is contacted with the vapor of the first compound having an atom in an oxidized state and then the vapor of the reducing agent for 1 to 5000 deposition cycles. In another refinement, the substrate is contacted with the vapor of the first compound having an atom in an oxidized state and then the vapor of the reducing agent for 10 to 2000 deposition cycles. In still another refinement, the substrate is contacted with the vapor of the first compound having an atom in an oxidized state and then the vapor of the reducing agent for 20 to 1000 deposition cycles.

Figure 2E:
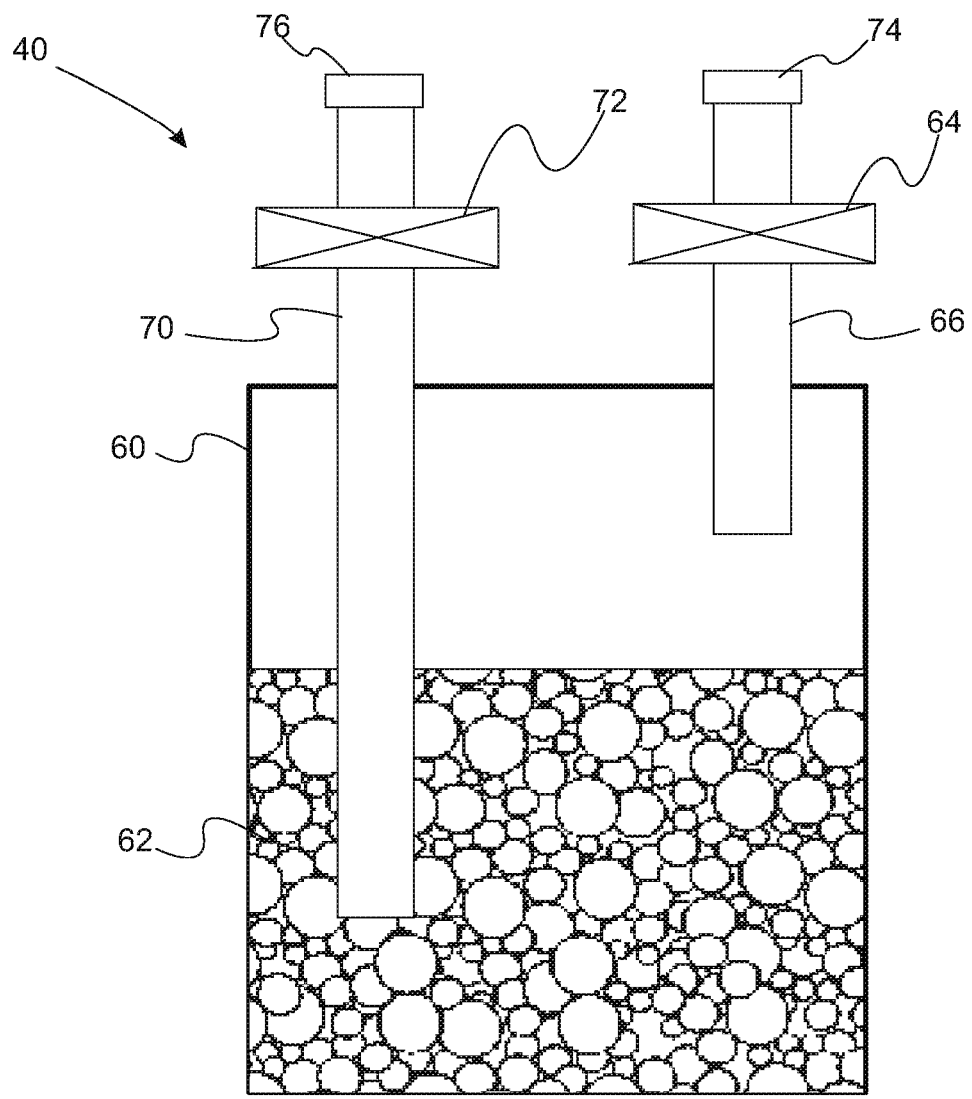
FIG. 2E is a schematic cross-section of a vapor source containing the reducing agents.

The system of FIG. 2D uses a source 40 for providing the vapor of a reducing agent. FIG. 2E provides a schematic cross-section of such a vapor source. Reducing agent source 40 includes vessel 60 and reducing agent 62 which is contained within and held by the vessel. Reducing agent 62 is one or more of the reducing agents set forth above. In particular, reducing agent 62 is described by IA, IB, IIA, IIB, IIC, and IID. In a refinement, at least a portion of the reducing agent is in the liquid phase. Valve 64 is attached to vessel 60. Valve 64 prevents escape of the reducing agent when the valve is closed and allows escape (i.e., passage into the ALD reaction chamber 22 through output conduit 66) of the reducing agent when the valve is opened. In a refinement, source 40 is a bubbler having an input conduit 70 for flowing a gas into vessel 60 and out of output conduit 66 thereby transferring the reducing agent. Valve 72 allows input conduit 70 to be opened and closed. In a refinement, in a refinement reducing agent source 40 includes fitting 74 positioned outside of and in fluid communication with valve 64. Optional, fitting 76 is position outside of and in fluid communication with valve 72. Fittings 74 and 76 allow attachment of the reducing agent source to ALD or CVD equipment.

In another embodiment, a system and method of forming a metal-containing film is provided. With reference to FIG. 2D, the vapor of the first compound having an atom in an oxidized state is introduced from precursor source 32 into reaction chamber 22 for a first predetermined pulse time. The first predetermined pulse time should be sufficiently long that available binding sites on the substrate surface (coated with metal layers or uncoated) are saturated (i.e., metal-containing compound attached). Typically, the first predetermined pulse time is from 1 second to 20 seconds. The first predetermined pulse time is controlled via control valve 34. At least a portion of the vapor of the metal-containing compound modifies (e.g., adsorbs or reacts with) substrate surface 36 to form a first modified surface. Reaction chamber 22 is then purged with an inert gas from purge source 44 for a first purge time. The first purge time is sufficient to remove the metal-containing compound from reaction chamber 22 and is typically from 0.5 seconds to 2 minutes.

Figure 3:
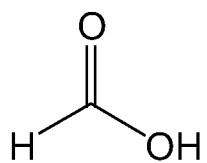
FIG. 3 provides examples of acids that can be reacted with the compounds of formula I.
Figure 3:
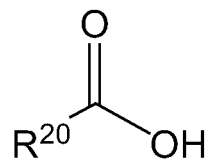
Figure 3:
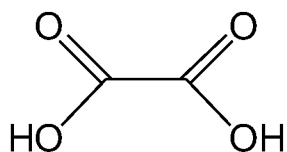
Figure 3:
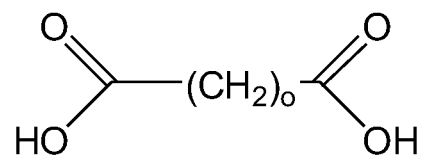
Figure 3:
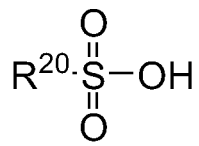
Figure 3:
Figure 3:

In the next reaction step of the deposition cycle, an acid such as formic acid is then introduced from acid source 50 into reaction chamber 22 for a second predetermined pulse time. Examples of other suitable acids are provided in FIG. 3. In FIG. 3, $R^{20}$ is H (i.e., hydride), $C_{1-8}$ alkyl, $C_{6-12}$ aryl, or $C_{1-8}$ fluoroalkyl, X is $N_3^-$, $NO_3^-$, halide (e.g., Cl, F, Br), and o is an integer from 1 to 6. In a refinement, $R^{20}$ is hydride, $C_{1-4}$ alkyl, $C_{6-10}$ aryl, or $C_{1-4}$ fluoroalkyl, X is $N_3^-$, $NO_3^-$, halide (e.g., Cl, F, Br), and n is an integer from 1 to 6. Examples of useful alkyl groups include, but are not limited to, methyl, ethyl, n-propyl, isopropyl, n-butyl, t-butyl, iso-butyl, sec-butyl, and the like. Examples of useful aryl groups include, but are not limited to, phenyl, tolyl, naphthyl, and the like. The second predetermined pulse time is controlled via valve 52 and should be sufficiently long that available binding sites on the first modified substrate surface are saturated and a second modified surface is formed. Typically, the second predetermined pulse time is from 0.1 second to 20 seconds. Reaction chamber 22 is then purged with an inert gas for a second purge time (typically, 0.5 seconds to 2 minutes as set forth above).

In the final reaction step of the deposition cycle, a reducing agent as set forth above is then introduced from reducing agent source 40 into reaction chamber 22 for a third predetermined time controlled by valve 42. The third predetermined pulse time should be sufficiently long that available binding sites on the second modified substrate surface are saturated, with a metal layer being formed thereon. Typically, the third predetermined pulse time is from 0.1 second to 20 seconds. Reaction chamber 22 is then purged with an inert gas for a third purge time (typically, 0.5 second to 2 minutes as set forth above).

During film formation by the method of the present embodiment, the substrate will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

In another embodiment, a method for forming a metal is provided. The method of this embodiment is an advancement of the method of U.S. patent application Ser. Nos. 13/818,154 and 13/930,471, the entire disclosures of which are hereby incorporated by reference. The method includes a step of contacting a metal-containing compound having at least one diazabutadiene ligand, the metal-containing compound having formula III or IV:

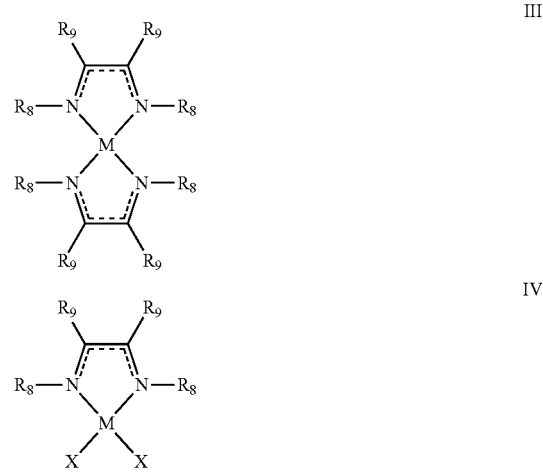

with an activating compound. The activating compound is an acid or a diketone at a sufficient temperature to form a metal film, wherein:

M is a transition metal selected from Groups 3-10 of the Periodic Table, Ru, Pd, Pt, Rh, and Ir;

$R_8$ is $C_1$-$C_{12}$ alkyl, amino (i.e., —$NH_2$), or $C_6$-$C_{18}$ aryl;

$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino and X is Cl, Br, or I. In a refinement, M is Mg, Al, Ti, V, Cr, Mn, Fe, Co, Ni, Cu, Zn, Sn, or Sb. In another refinement, when the metal-containing compound has formula II, M is Cr, Mn, Fe, Ni, Co, Zn, Al, or Mg. In still another refinement, M is Mg, Al, Sn, or Sb. In a useful variation, the $C_{2-5}$ diketone is a 1,3-diketone. It should be appreciated that the reaction of the present embodiment can be in the gas or liquid phases. In other variations, the reaction is an ALD reaction as set forth below.

In another variation of the present embodiment, M is a metal, and in particular, a transition metal in a 0, 1+, 2+, 3+, or 4+ oxidation state. Examples of useful transition metals for M include, but are not limited to, Cu, Ni, Co, Cr, Mn, Fe, W, Mo, Ti, Zr, Hf, Rf, V, Nb, Ta, Re, Ru, Rh, Ir, Pd, Pt, and Au. Particularly useful examples for M include, but are not limited to, Cr(II), Mn(II), Fe(II), Co(II), and Ni(II).

As set forth above, $R_8$ is a $C_1$-$C_{12}$ alkyl or $C_6$-$C_{18}$ aryl. In a variation, $R_8$ is $C_1$-$C_4$ alkyl. Specific examples for $R_8$ include, but are not limited to, methyl, ethyl, propyl, n-butyl, sec-butyl, isobutyl, t-butyl, and the like. In a particularly useful refinement, $R_1$ is t-butyl. In another variation, $R_8$ is $C_6$-$C_{10}$ aryl. In this refinement, specific examples for $R_1$ include, but are not limited to, phenyl, biphenyl, napthyl, and the like. In a further refinement, it should be appreciated that the definitions for $R_1$ include substituted variations of such groups. Examples of substituents include, but are not limited to, halogen, hydroxyl, —$NO_2$, and in the case of aryl, $C_1$-$C_4$ alkyl. These substituents are particularly relevant when $R_1$ is aryl.

As set forth above, $R_9$ is $C_1$-$C_{12}$ alkyl or $C_6$-$C_{18}$ aryl. In a variation, $R_9$ is $C_1$-$C_4$ alkyl. In this refinement, specific examples for $R_8$ include, but are not limited to, methyl, ethyl, propyl, n-butyl, sec-butyl, isobutyl, t-butyl, and the like. It should also be appreciated that when $R_9$ is $C_1$-$C_{12}$ alkylamino or $C_2$-$C_{22}$ dialkylamino, the alkyl component is the same as set forth for when $R_8$ is a $C_1$-$C_{12}$ alkyl. Therefore, additional specific examples for $R_9$ include, but are not limited to, methylamino, ethylamino, propylamino, diethylamino, dimethylamino, dipropylamino, and the like. In another refinement, $R_9$ is $C_6$-$C_{10}$ aryl. In this refinement, specific examples for $R_1$ include, but are not limited to, phenyl, biphenyl, napthyl, and the like. In a further refinement, it should be appreciated that the definitions for $R_9$ include substituted variations of such groups. Examples of substituents include, but are not limited to, halogen, hydroxyl, —$NO_2$, and in the case of aryl, $C_1$-$C_4$ alkyl. These substituents are particularly relevant when $R_1$ is aryl.

As set forth above, the methods of the invention use an activating compound, such as an acid. Particularly useful activating compounds are $C_{1-5}$ organic acids (e.g., $C_{1-5}$ carboxylic acids) such as formic acid and $C_{1-8}$ diketones. Examples of other suitable acids are provided in FIG. 3. In FIG. 3, $R^{20}$ is H (i.e., hydride), $C_{1-8}$ alkyl, $C_{6-12}$ aryl, or $C_{1-8}$ fluoroalkyl, X is $N_3^-$, $NO_3^-$, halide (e.g., Cl, F, Br), and n is an integer from 1 to 6. In a refinement, $R^{20}$ is hydride, $C_{1-4}$ alkyl, $C_{6-10}$ aryl, or $C_{1-4}$ fluoroalkyl, X is $N_3^-$, $NO_3^-$, halide (e.g., Cl, F, Br), and n is an integer from 1 to 6. Examples of useful alkyl groups include, but are not limited to, methyl, ethyl, n-propyl, isopropyl, n-butyl, t-butyl, iso-butyl, sec-butyl, and the like. Examples of useful aryl groups include, but are not limited to, phenyl, tolyl, naphthyl, and the like.

In another variation, when M is Ni, Co, Fe, Mn, Mg, Zn or Cr, the diazabutadiene ligand is a radical anion having the following formula:

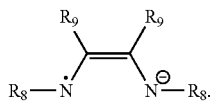

In still another variation, when M is Ti, the diazabutadiene ligand is a dianion having the following formula:

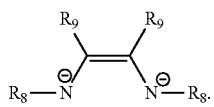

In yet another variation, when M is Al, the metal-containing compound includes a diazabutadiene ligand that is a radical ion having the following formula:

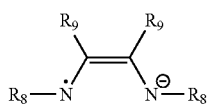

and a diazabutadiene ligand that is a dianion having the following formula:

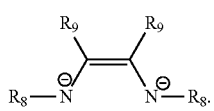

With reference to FIG. 2C, a method of forming a thin metal film is schematically illustrated. In step a), substrate 10 is contacted with a vapor of a metal-containing compound G1 having formula III or IV to form a modified surface 12 on the substrate 10. The modified surface is then contacted with the activating compound A1 to form at least a portion of the metal film on the substrate. The present variation is particularly useful when M is Co, Ni, Cr, Fe, and Mn.

With reference to FIG. 2B, another variation for forming a metal film is schematically illustrated. In step a), substrate 10 is contacted with a vapor of a metal-containing compound G1 having formula III or IV to form a first modified surface 12 on the substrate 10. In step b), the first modified surface 12 is then contacted with a vapor of the activating compound A1 to form a second modified surface 12'. In step c), the second modified surface 12' is then contacted with the vapor of a reducing agent G2 to form at least a portion of a metal film on the substrate. Examples of suitable reducing agents include, but are not limited to, hydrazine, hydrazine hydrate, alkyl hydrazines, 1,1-dialkylhydrazines, 1,2-dialkylhydrazines, $H_2$, $H_2$ plasma, ammonia, ammonia plasma, silanes, disilanes, trisilanes, germanes, diborane, formalin, amine borane, dialkyl zinc, alkyl aluminum, alkyl gallium, alkyl indium complexes, and other plasma-based gases, and combinations thereof. Additional examples of reducing agents include the bis(trimethylsilyl) six-membered ring systems and related compounds as set forth above.

With reference to FIG. 2D, deposition system 20 includes reaction chamber 22, substrate holder 24, and vacuum pump 26. Typically, the substrate is heated via heater 28. The method has a deposition cycle comprising contacting substrate 30 with a vapor of the compound having formula III or IV or the variations of these compounds as set forth above. In particular, the vapor is introduced from precursor source 32 into reaction chamber 22 for a predetermined pulse time. The pulse time is controlled via control valve 34. At least a portion of the vapor of the compound having formula III or IV modifies (e.g, adsorbs or reacts with) substrate surface 36 to form a modified surface. The method further comprises contacting the modified surface with a vapor of the activating compound (e.g., $C_{1-5}$ organic acids such as formic acid and $C_{1-8}$ diketone) as set forth above from source 50 for a predetermined pulse time to form a metal layer or metal-containing layer.

In a variation of the present embodiment, the method further comprises removing at least a portion of the vapor of the compound having formula III or IV that is lingering in the gas phase (i.e., has not adsorbed or reacted with the substrate) from the vicinity of the substrate before introducing the vapor of the activating compound and removing at least a portion of the vapor of the activating compound from the vicinity of the substrate. The metal-containing compound and the activating compound are removed in purging steps by introducing a purge gas from purge source 44 into reaction chamber 22 for a predetermined purge time. The purge time is controlled by control valve 46.

In another variation, the method further includes at least one additional deposition cycle comprising sequentially contacting the substrate with the vapor of the compound having formula III or IV and then the vapor of the reducing agent. In some refinements, the substrate is contacted for a plurality of additional deposition cycles. For example, the substrate may be contacted with from 1 to several thousand deposition cycles depending on the thickness of the film desired. In particular, the substrate is contacted with the vapor of the compound having formula III or IV and then the vapor of the activating compound for 1 to 5000 deposition cycles. In another refinement, the substrate is contacted with the vapor of the compound having formula III or IV and then the vapor of the activating compound for 10 to 2000 deposition cycles. In still another refinement, the substrate is contacted with the vapor of the compound having formula III or IV and then the vapor of the activating compound for 20 to 1000 deposition cycles.

In another embodiment, a method of forming a metal-containing film is provided. With reference to FIG. 2D, the vapor of the compound having formula III or IV is introduced from precursor source 32 into reaction chamber 22 for a first predetermined pulse time. The first predetermined pulse time should be sufficiently long that available binding sites on the substrate surface (coated with metal layers or uncoated) are saturated (i.e., metal-containing compound attached). Typically, the first predetermined pulse time is from 1 second to 20 seconds. The first predetermined pulse time is controlled via control valve 34. At least a portion of the vapor of the metal-containing compound modifies (e.g, adsorbs or reacts with) substrate surface 36 to form a first modified surface. Reaction chamber 22 is then purged with an inert gas from purge gas source 44 for a first purge time. The first purge time is sufficient to remove the metal-containing compound from reaction chamber 22 and is typically from 0.5 seconds to 2 minutes.

In the next reaction step of the deposition cycle, the activating compound (e.g., $C_{1-5}$ organic acids such as formic acid and $C_{1-8}$ diketone) as set forth above is then introduced from source 50 into reaction chamber 22 for a second predetermined pulse time. The second predetermined pulse time is controlled via valve 52 and should be sufficiently long that available binding sites on the first modified substrate surface are saturated and a second modified surface is formed. Typically, the second predetermined pulse time is from 0.1 second to 20 seconds. The second predetermined pulse time is controlled via control valve 32. Reaction chamber 12 is then purged with an inert gas for a second purge time (typically, 0.5 seconds to 2 minutes as set forth above).

In the final reaction step of the deposition cycle, a reducing agent having formula IA or IB or the derivatives thereof as set forth above is then introduced from reducing agent source 40 into reaction chamber 22 for a third predetermined time controlled by valve 42. The third predetermined pulse time should be sufficiently long that available binding sites on the second modified substrate surface are saturated, with a metal layer being formed thereon. Typically, the third predetermined pulse time is from 0.1 second to 20 seconds. Reaction chamber 22 is then purged with an inert gas for a third purge time (typically, 0.5 seconds to 2 minutes as set forth above).

In a variation of the present embodiment, the method further includes at least one additional deposition cycle comprising sequentially contacting the substrate with the vapor of the compound having formula III or IV and then the vapor of the reducing agent. In some refinements, the substrate is contacted for a plurality of additional deposition cycles. For example, the substrate may be contacted with from 1 to several thousand deposition cycles depending on the thickness of the film desired. In particular, the substrate is contacted with the vapor of the compound having formula III or IV and then the vapor of the activating compound for 1 to 5000 deposition cycles. In another refinement, the substrate is contacted with the vapor of the compound having formula III or IV and then the vapor of the activating compound for 10 to 2000 deposition cycles. In still another refinement, the substrate is contacted with the vapor of the compound having formula III or IV and then the vapor of the activating compound for 20 to 1000 deposition cycles.

During film formation by the methods set forth above, the substrate will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

The following examples illustrate the various embodiments of the present invention. Those skilled in the art will recognize many variations that are within the spirit of the present invention and scope of the claims.

Experimental Section

All experiments employed the use of anhydrous reagents and solvents, obtained from Sigma Aldrich. Syntheses of CHD and DHP were carried out using Schlenk line techniques, following previously referenced literature procedures contained in U.S. patent application Ser. No. 13/930,471 filed Jun. 28, 2013. Solution reactions and sample preparations for deposition experiments were conducted in an argon dry box. A Picosun R-75BE ALD reactor was used for thin film depositions. The reactor was operated under a constant stream of nitrogen (99.9995%) at a pressure of 10-12 mbar. Film thicknesses were determined using cross-sectional field emission scanning electron microscopy (FESEM) on a JEOL-6510LV electron microscope. Powder and thin film XRD experiments were performed on a Rigaku R200B 12 kW rotating anode diffractometer, using Cu $K_\alpha$ radiation (1.54056 Å) at 40 kV and 150 mA. XPS analysis was performed on a Perkin-Elmer 5500 XPS system using monochromatized Al $K_\alpha$ radiation. AugerScan v3.2 was used as the analysis software. Deposited thin films were exposed to air for several days prior to XPS analysis.

1,4-bis(trimethylsilyl)-2-methyl-1,4-cyclohexadiene

Scheme 1 illustrates the synthesis of 1,4-bis(trimethylsilyl)-2-methyl-1,4-cyclohexadiene according to a literature procedure (Laguerre, M.; Dunogues, J.; Calas, R.; Duffaut, N. *J. Organomet. Chem.* 1976, 112, 49-59).

The air-sensitive product was a clear liquid, and was pure by $^1$H NMR.

Scheme 1

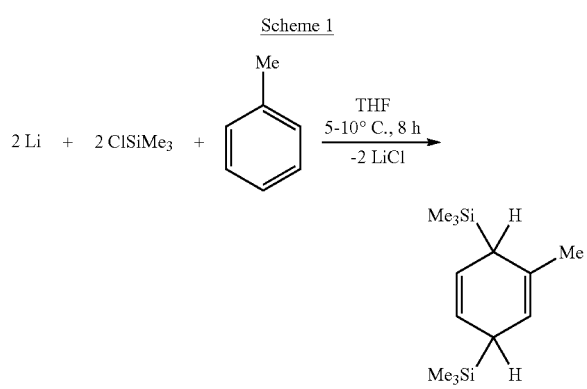

Figure 4:
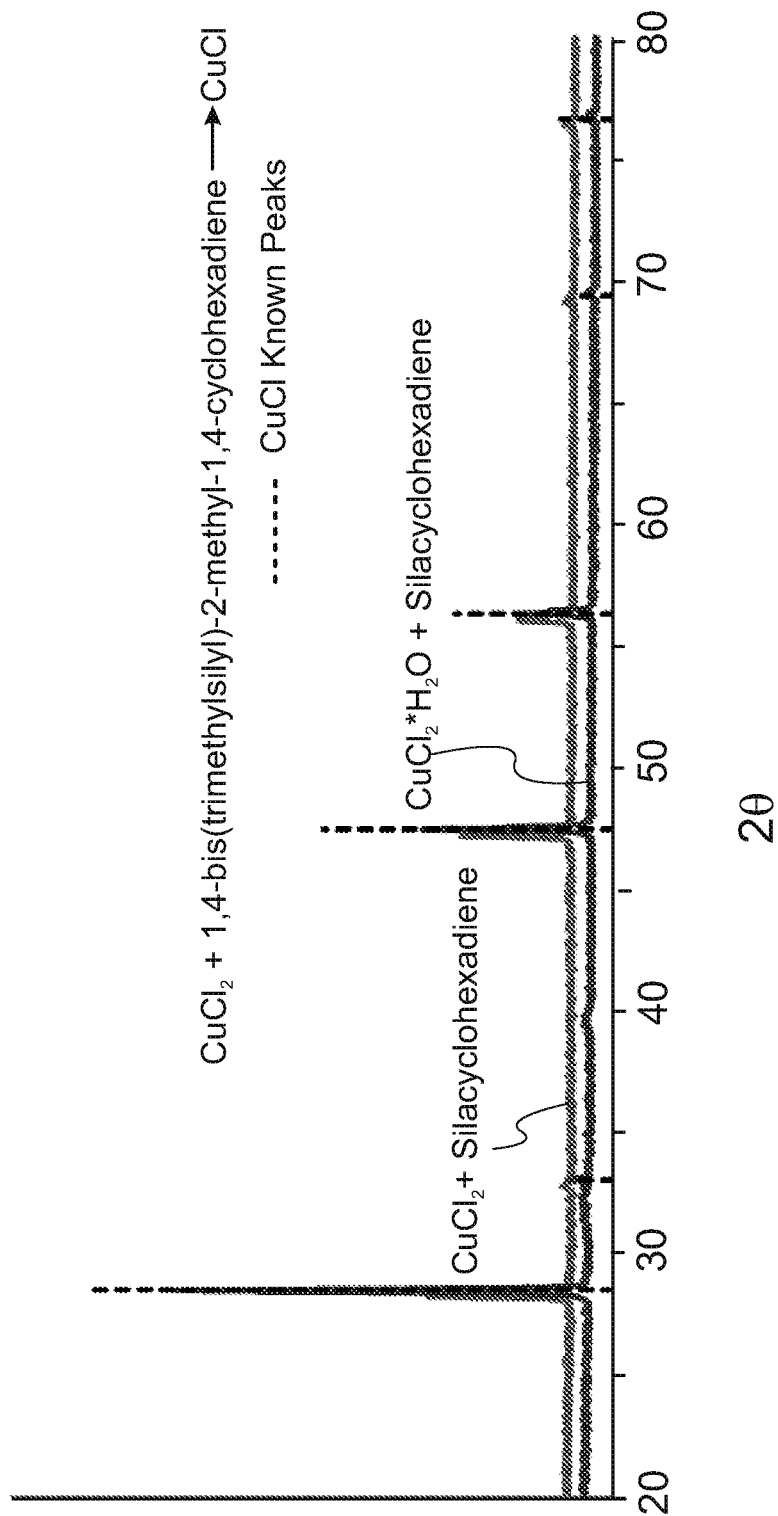
FIG. 4 provides X-ray diffraction spectra showing CuCl formed by the solution reductions of $CuCl_2$ and $CuCl_2.H_2O$ by 1,4-bis(trimethylsilyl)-2-methyl-1,4-cyclohexadiene.
Figure 5:
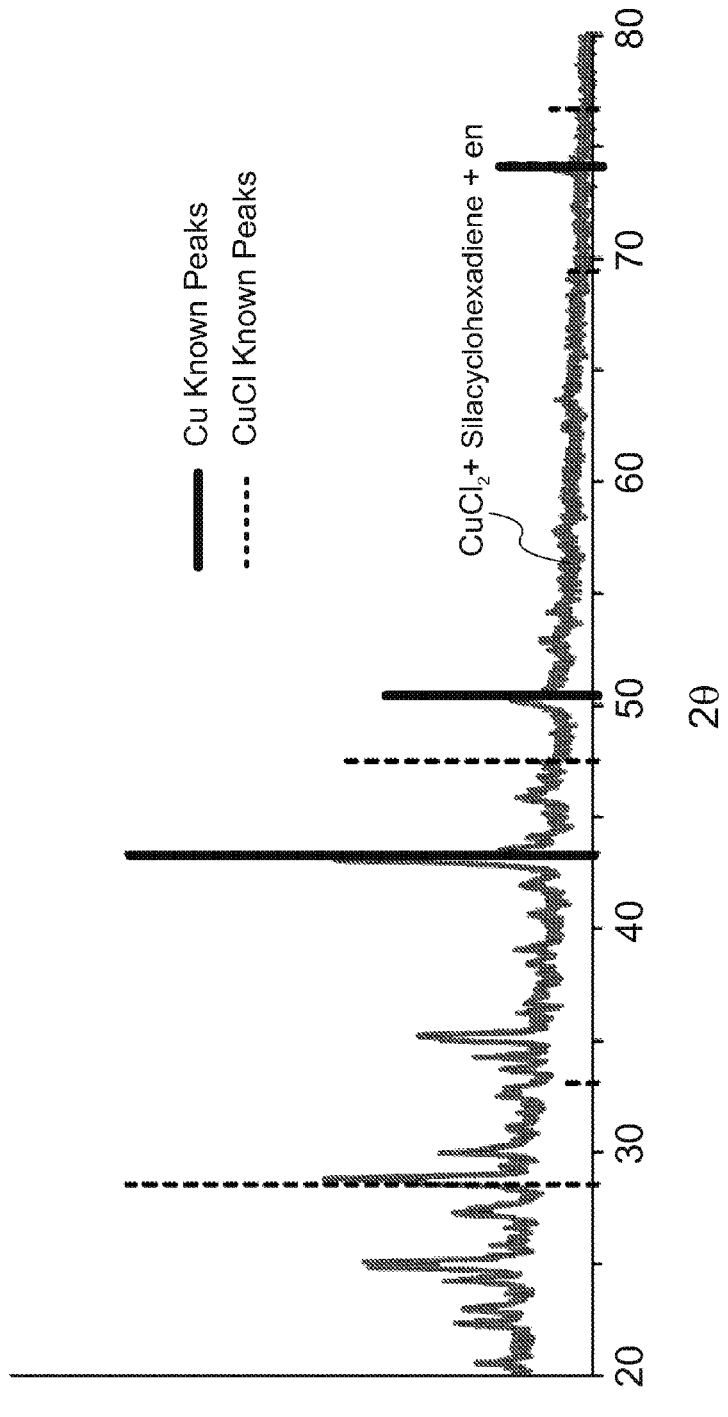
FIG. 5 provides an X-ray diffraction spectrum showing copper metal formed by the solution reduction of $CuCl_2$ to CuCl by 1,4-bis(trimethylsilyl)-2-methyl-1,4-cyclohexadiene, and the subsequent disproportionation to copper metal by ethylenediamine.

Solution reductions were attempted with a variety of metal salts, using five molar equivalents of 1,4-bis(trimethylsilyl)-2-methyl-1,4-cyclohexadiene (Table 1). Analysis by XRD confirmed that $CuCl_2$ and $CuCl_2 \cdot H_2O$ were each reduced to CuCl, (FIG. 4). However, CHD was unable to reduce any of the salts to elemental metal. A $CuCl_2 \cdot DME$ adduct was reduced to a CuCl species by CDH. Subsequent addition of ethylenediamine resulted in a disproportionation reaction and precipitation of copper metal (FIG. 5).

TABLE 1

Solution reduction reactions of various metal salts with 1,4-bis(trimethylsilyl)-2-methyl-1,4-cyclohexadiene.

| ML$_2$ | Sol | Vol | Reaction Temp | Reaction Time (min) | Reflux Temp | Time → (min) | Reaction solution → Precipitate |
|---|---|---|---|---|---|---|---|
| CuCl$_2$•H$_2$O | THF | 15 ml | RT | 60 | — | — | milky white → CuCl (insoluble) |
| CuCl$_2$•H$_2$O | THF | 50 ml | 0° C. | 5 | 65° C. | 65 | milky white → CuCl (insoluble) |
| CuCl$_2$•DME | DME | 45 ml | RT | 20 | 95° C. | 75 | milky white → add en → Cu metal |
| CuBr$_2$ | THF | 30 ml | RT | 60 | — | — | milky white → CuBr (probably) |
| Cu(dmap)$_2$ | THF | 15 ml | RT | 80 | 65° C. | 60 | dark orange → none |
| Cu(hfac)$_2$ | THF | 50 ml | RT | 35 | 65° C. | 60 | light green → none |
| Cu(tmhd)$_2$ | THF | 50 ml | RT | 60 | 65° C. | 60 | light blue → none |
| Cu(HCOO)$_2$ | THF | 50 ml | 0° C. | 5 | 65° C. | 60 | aqua green → none |
| CoCl$_2$ | THF | 50 ml | RT | 60 | 65° C. | 60 | light blue → none |
| ZnCl$_2$ | THF | 50 ml | RT | 105 | 65° C. | 60 | clear → none |

Copper metal film growth was attempted by ALD using bis(dimethylaminopropanoxide)copper [Cu(dmap)$_2$] and 1,4-bis(trimethylsilyl)-2-methyl-1,4-cyclohexadiene as reagents. Various substrates were tested for film growth, including Si(100), SiH, thermal SiO$_2$, Cu, Pt, Pd, TiN, and Ru/SiO$_2$. Each cycle consisted of a 3.0 s pulse of Cu(dmap)$_2$, a 10.0 s purge, a 1.0 s pulse of 1,4-bis(trimethylsilyl)-2-methyl-1,4-cyclohexadiene, and a final 10.0 s purge. The 1,4-bis(trimethylsilyl)-2-methyl-1,4-cyclohexadiene bubbler was maintained at 70° C. and the reaction chamber was held at 150° C. After 1,000 cycles, a copper film was clearly observable on the ruthenium substrate. A growth rate of 0.08 Å/cycle was determined after measurement of the film by SEM. Copper metal was not observed on any other substrates.

Scheme 2 provides a reaction scheme for a two-step ALD process using Cu(dmap)$_2$ and 1,4-bis(trimethylsilyl)-2-methyl-1,4-cyclohexadiene:

Scheme 2

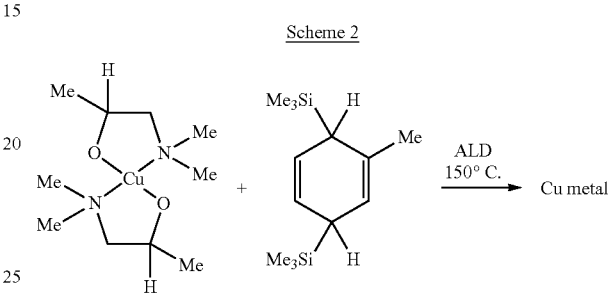

Figure 6:
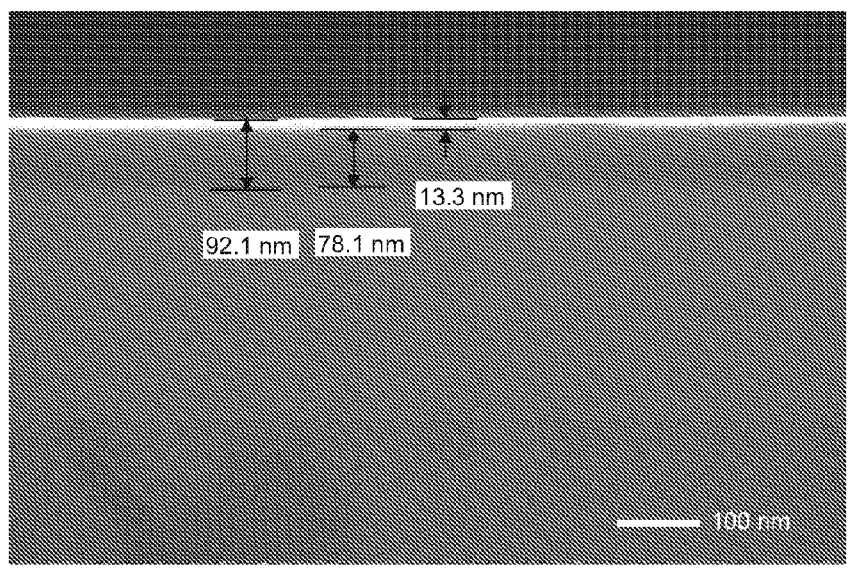
FIG. 6 provides a scanning electron micrograph of a copper film (~8 nm) on a ruthenium-coated (5 nm) $SiO_2$ wafer.

FIG. 6 provides a scanning electron micrograph of a copper film (~8 nm) on a ruthenium-coated (5 nm) SiO$_2$ wafer.

Computational Screening

Modifications to the ring substituents were explored computationally as a possible means of increasing reactivity. Using Gaussian 09, numerous bis(silyl)hexadiene structures were optimized with the 6-311+G(d,p) basis set at the B3LYP level in the gas phase. The total electronic energy of the silylated structure was subtracted from that of the aromatic structure. The energy difference of each molecular variant was expressed relative to the toluene analogue (CHD), which was normalized to zero. This model considers only the relative change in the electronic energy of the reducing agent upon aromatization, irrespective of the ligand system being used. Reaction kinetics and changes in system entropy were not taken into account. To reduce the computational effort, the trimethylsilyl groups were approximated by SiH$_3$ groups. Scheme 3 provides a partial reaction showing the desilylation of the non-conjugated cyclohexadiene backbone resulting in the formation of an aromatic product:

Scheme 3

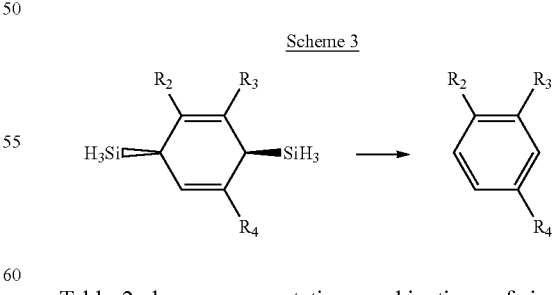

Table 2 shows representative combinations of ring substituents, along with the relative electronic energy differences. The structure with three methoxy groups shows the greatest improvement, with −3.636 kcal per mole upon aromatization relative to CHD. These data do not indicate significant improvements to the initial CHD structure, and thus, were not explored experimentally.

TABLE 2

Representative values of the relative electronic energy difference upon aromatization with respect to CHD.

| $R_2$ | $R_3$ | $R_4$ | $\Delta E_{rel}$ [kcal/mol] |
|---|---|---|---|
| H | H | H | −0.031 |
| $CH_3$ | H | H | — |
| $CH_3$ | $CH_3$ | H | −3.038 |
| $CH_3$ | H | $CH_3$ | −0.036 |
| H | $CH_3$ | $CH_3$ | 0.089 |
| $CH_3$ | $CH_3$ | $CH_3$ | −3.147 |
| $NO_2$ | H | H | 1.346 |
| $NO_2$ | $NO_2$ | H | 0.585 |
| $NO_2$ | H | $NO_2$ | 4.162 |
| H | $NO_2$ | $NO_2$ | 4.982 |
| $NO_2$ | $NO_2$ | $NO_2$ | 3.618 |
| $OCH_3$ | H | H | 2.560 |
| $OCH_3$ | $OCH_3$ | H | −2.610 |
| $OCH_3$ | H | $OCH_3$ | 2.070 |
| H | $OCH_3$ | $OCH_3$ | 0.389 |
| $OCH_3$ | $OCH_3$ | $OCH_3$ | −3.636 |
| $Si(CH_3)_3$ | H | H | −1.824 |
| $CH_3$ | $NO_2$ | H | 0.390 |
| $CH_3$ | H | $NO_2$ | 0.520 |
| H | $CH_3$ | $NO_2$ | 1.124 |
| $CH_3$ | $CH_3$ | $NO_2$ | −2.737 |
| $CH_3$ | $NO_2$ | $CH_3$ | 0.256 |
| $NO_2$ | $CH_3$ | $CH_3$ | −1.648 |
| $NO_2$ | $NO_2$ | $CH_3$ | 0.190 |
| $NO_2$ | $CH_3$ | $NO_2$ | 2.487 |
| $CH_3$ | $NO_2$ | $NO_2$ | 3.118 |

Figure 7:
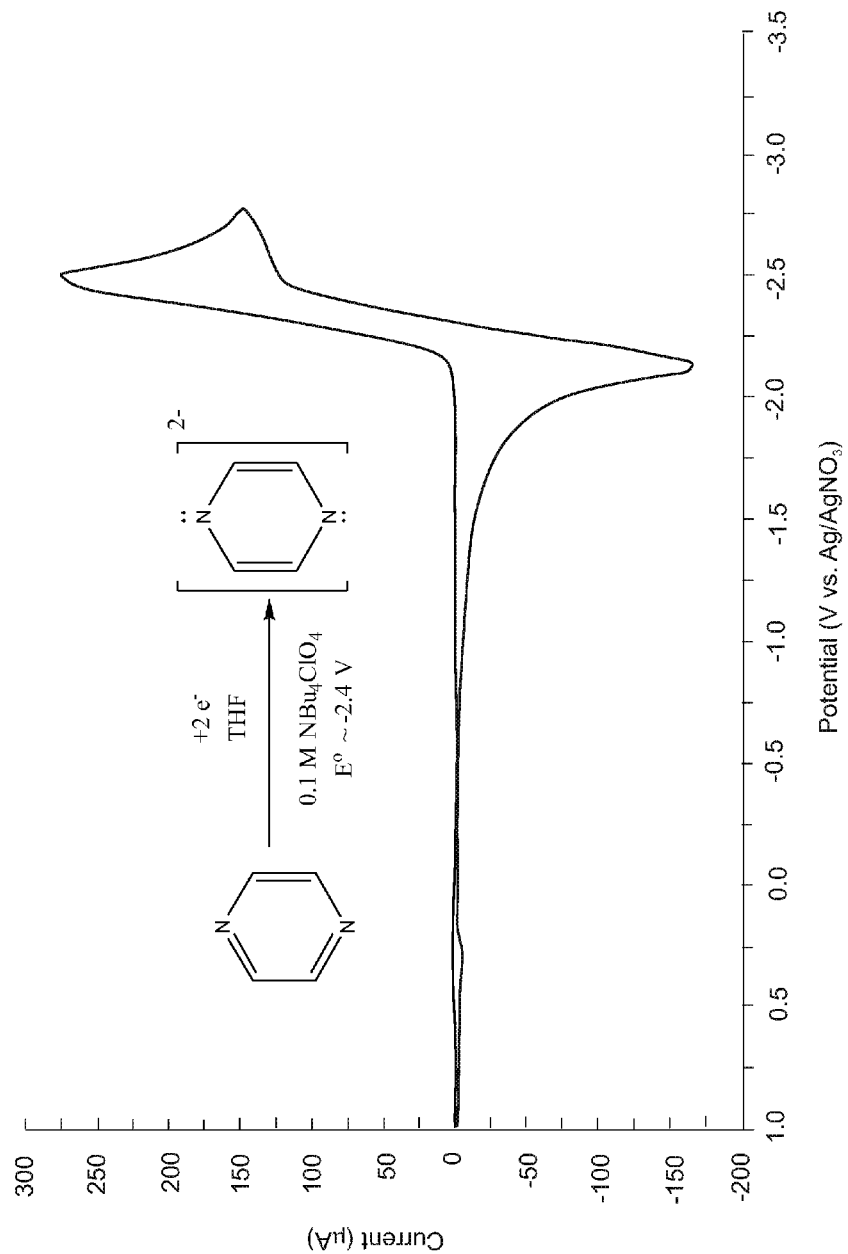
FIG. 7 provides a cyclic voltammogram of pyrazine referenced to $Ag/AgNO_3$.

Subsequently, attention focused on modifying the ring system itself. It is postulated that an 8 π electron anti-aromatic structure would have a greater driving force toward aromatization than would any 4 π electron non-conjugated system. The 1,4-bis(trimethylsilyl)-1,4-dihydropyrazine (DHP) molecule was previously crystallized as a planar structure (Hausen, H. D.; Mundt, O.; Kaim, W. *J. Organomet. Chem.* 1985, 296, 321-337) possessing anti-aromatic character and a very low first vertical ionization energy of 6.16 (eV) (Kaim, W. *J. Am. Chem. Soc.* 1983, 105, 707-713). The trimethylsilyl moieties should be highly reactive towards the ligands (e.g. halogens), affording a trimethylsilated ligand byproduct. The resulting pyrazine dianion may simultaneously coordinate to the metal cation. Subsequent formation of an aromatic pyrazine byproduct may facilitate the reduction to elemental metal. Pyrazine has a cathodic potential of −2.4 V as measured relative to Ag/AgNO₃ (FIG. 7). Thus, this approach may enable the thermal reduction of numerous metal precursors that are otherwise unreactive towards conventional coreagents at temperatures suitable for ALD.

1,4-bis(trimethylsilyl)-1,4-dihydropyrazine 1,4-bis(trimethylsilyl)-1,4-dihydropyrazine was prepared on a 40 g scale following a literature procedure (Sulzbach, R. A.; Iqbal, A. F. M. *Angew. Chem. Int. Ed. Engl.* 1971, 10, 127). The air-sensitive, yellow solid was purified by sublimation at 80° C./0.05 Torr. Preparative sublimation of the product yielded 97.1% recovery with no residue. The thermal decomposition temperature was determined to be greater than 265° C.

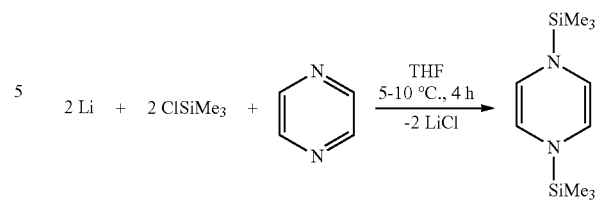

Figure 8:
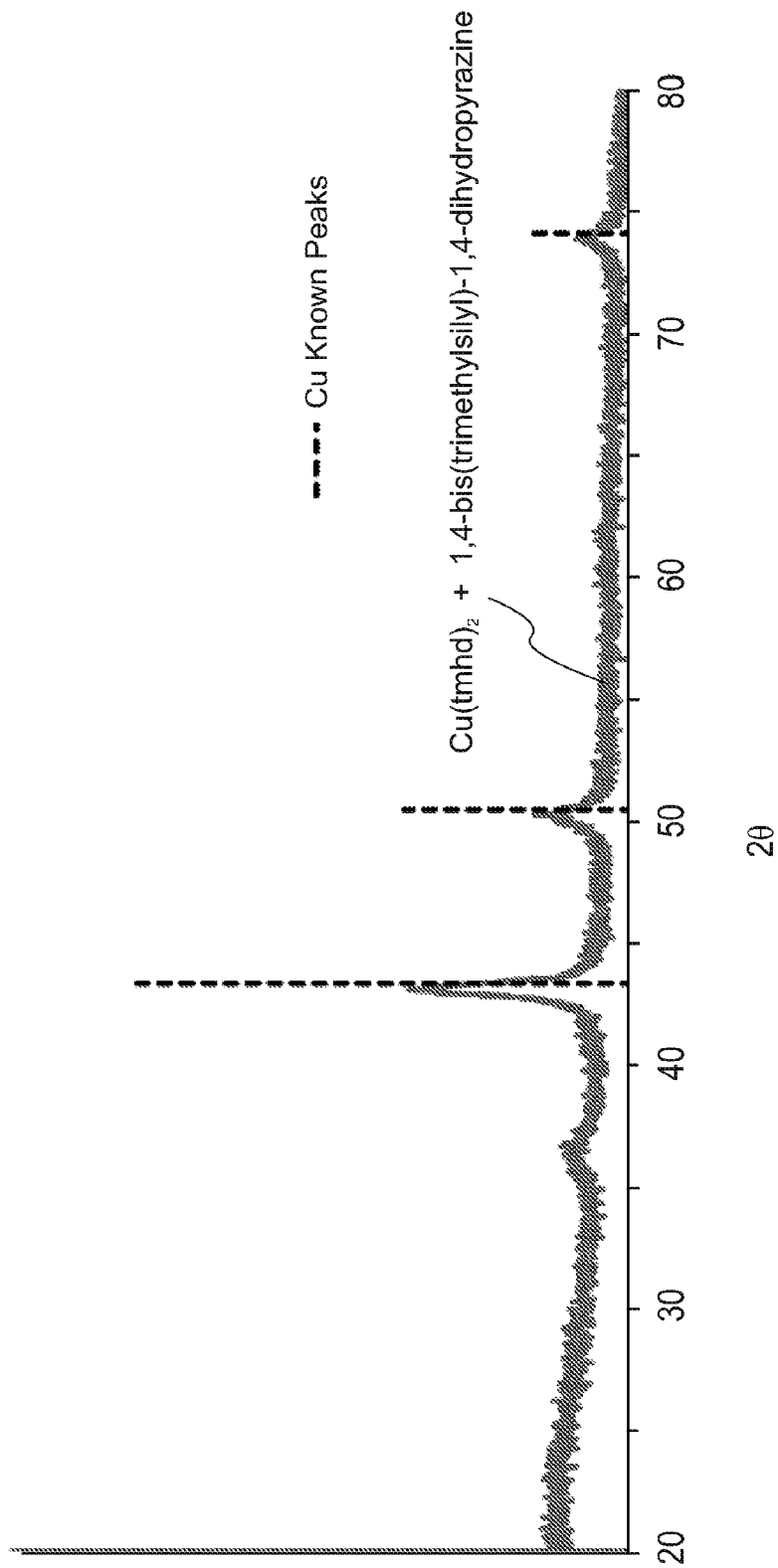
FIG. 8 provides an X-ray diffraction spectrum showing copper metal formed by the solution reduction of $Cu(tmhd)_2$ by 1,4-bis(trimethylsilyl)-1,4-dihydropyrazine.
Figure 9:
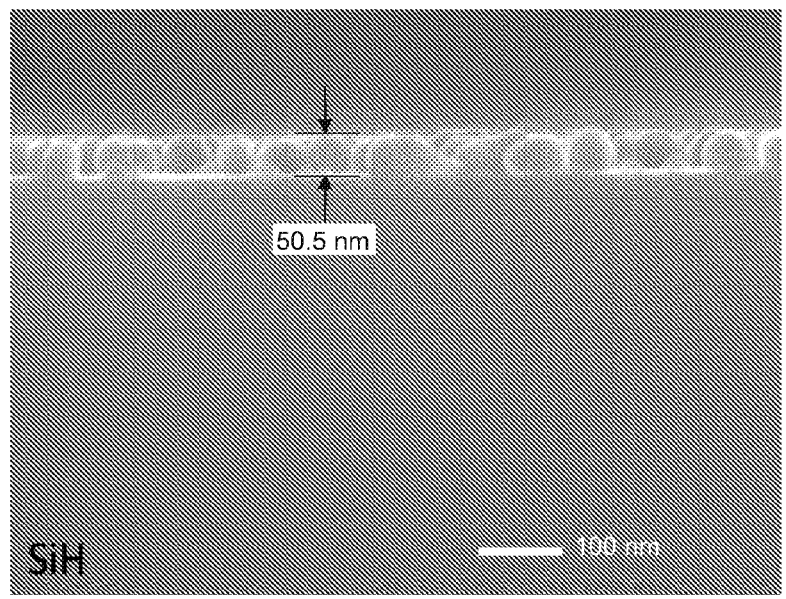
FIG. 9 provides a cross-sectional SEM micrograph of a copper film on a SiH substrate formed from $Cu(dmap)_2$.
Figure 10:
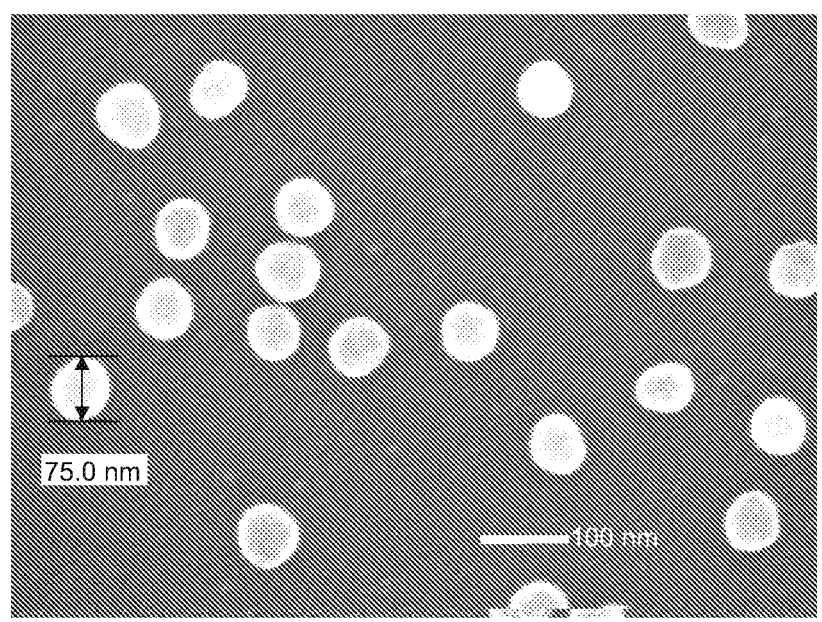
FIG. 10 provides a top-down SEM micrograph of a copper film on $Co/SiO_2$ formed from $Cu(dmap)_2$.
Figure 11:
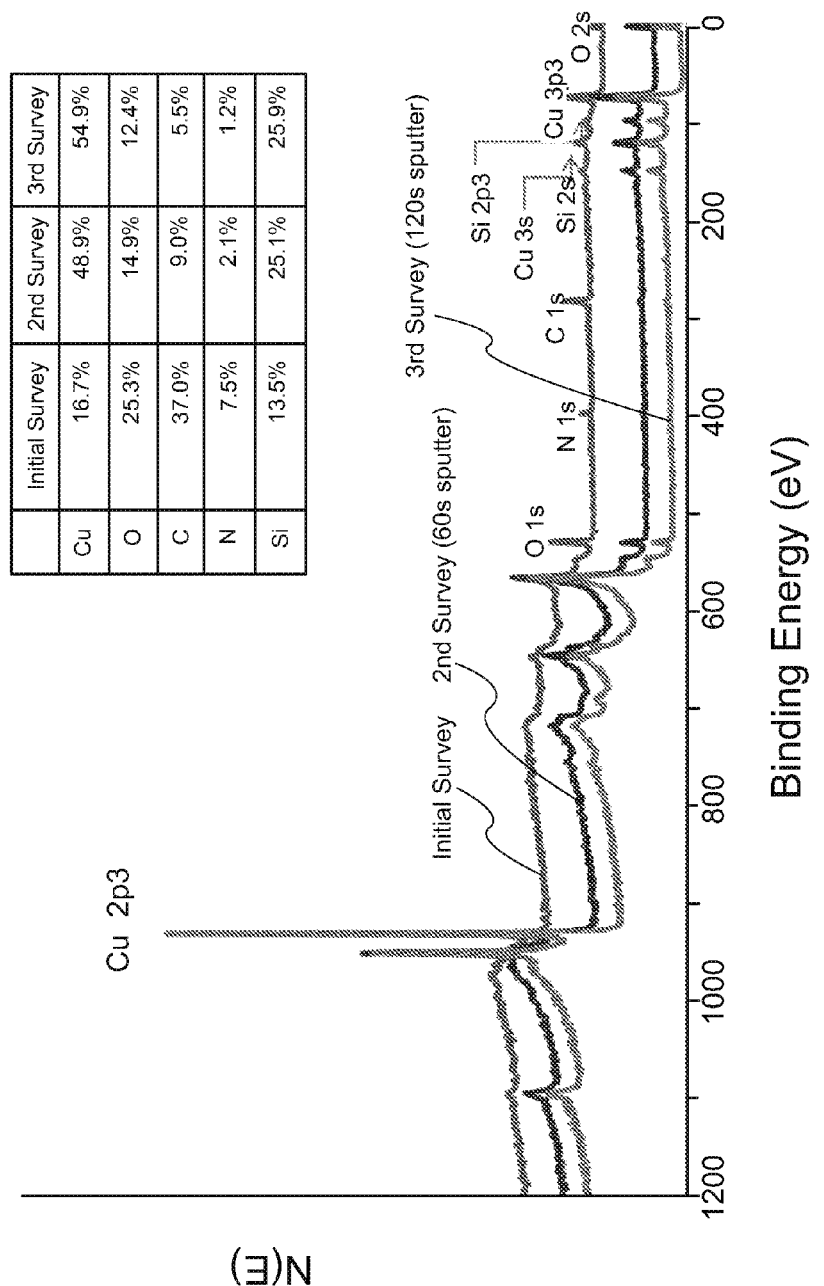
FIG. 11 provides XPS survey scans of a 51 nm copper film deposited on SiH at 150° C. formed from $Cu(dmap)_2$.
Figure 12:
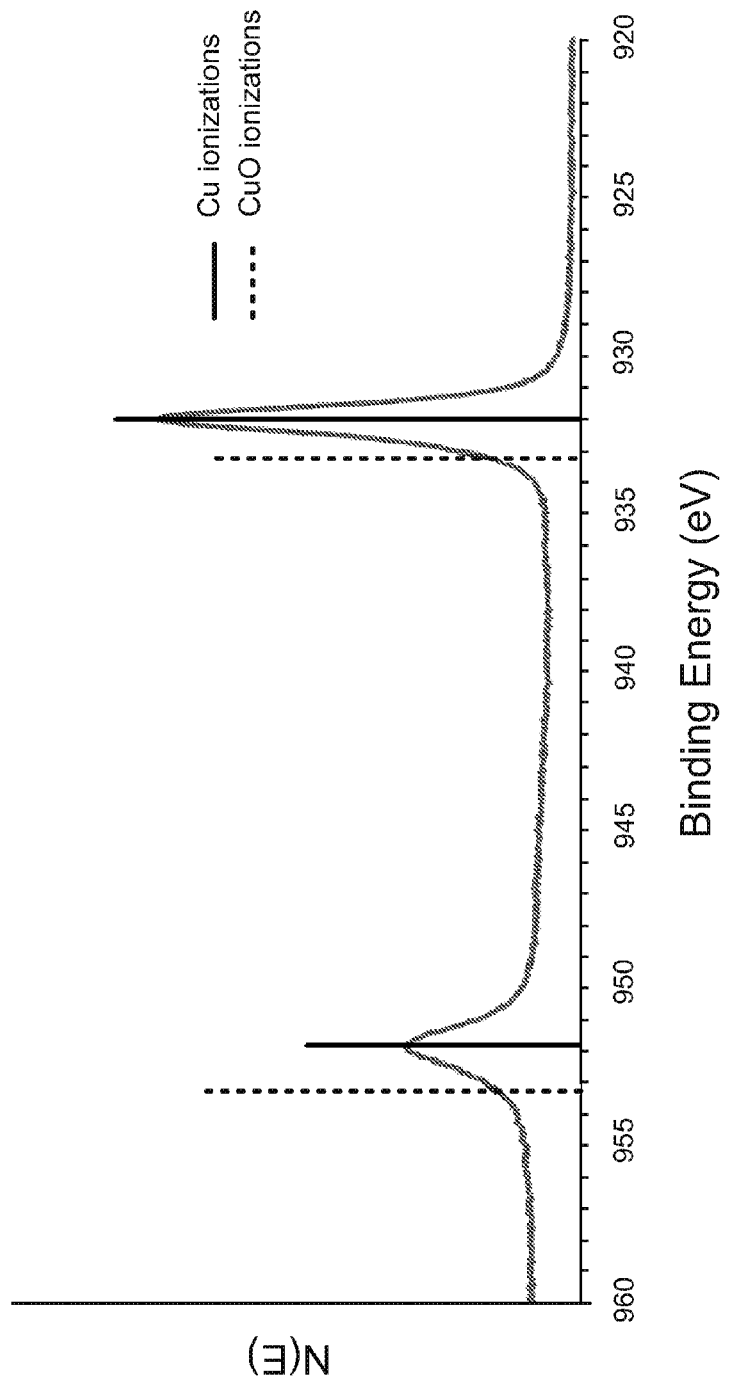
FIG. 12 provides an XPS high-resolution multiplex of the Cu 2p3 region of a film formed from $Cu(dmap)_2$.
Figure 13:
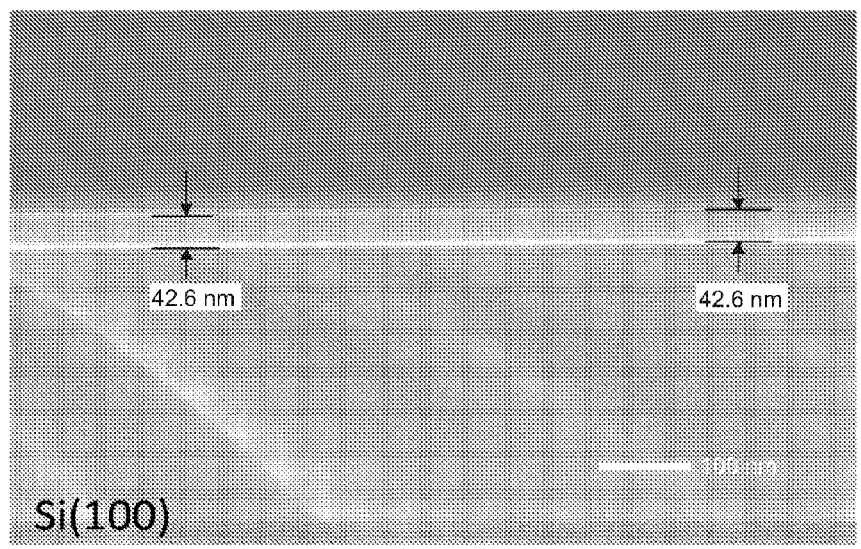
FIG. 13 provides a cross-sectional SEM micrograph of a nickel film on a Si(100) substrate formed from $Ni(dmap)_2$.
Figure 14:
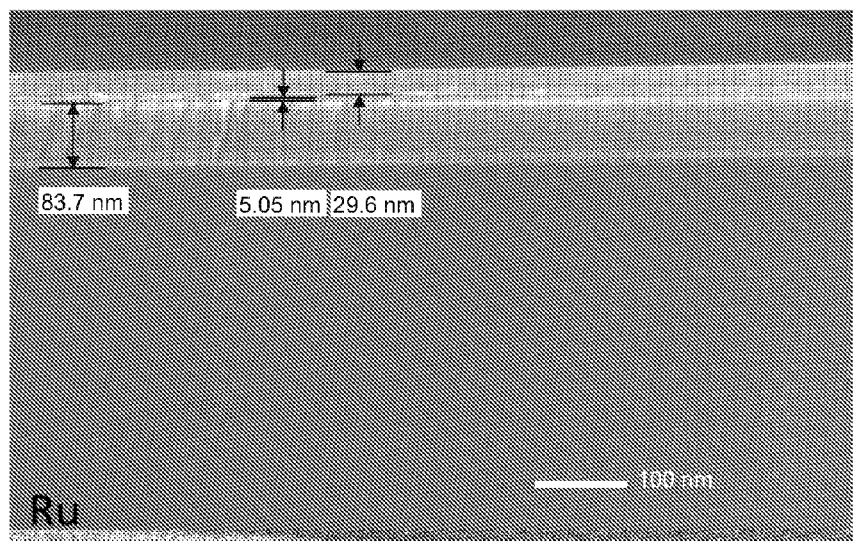
FIG. 14 provides a cross-sectional SEM micrograph of a nickel film on a $Ru/SiO_2$ substrate formed from $Ni(dmap)_2$.
Figure 15:
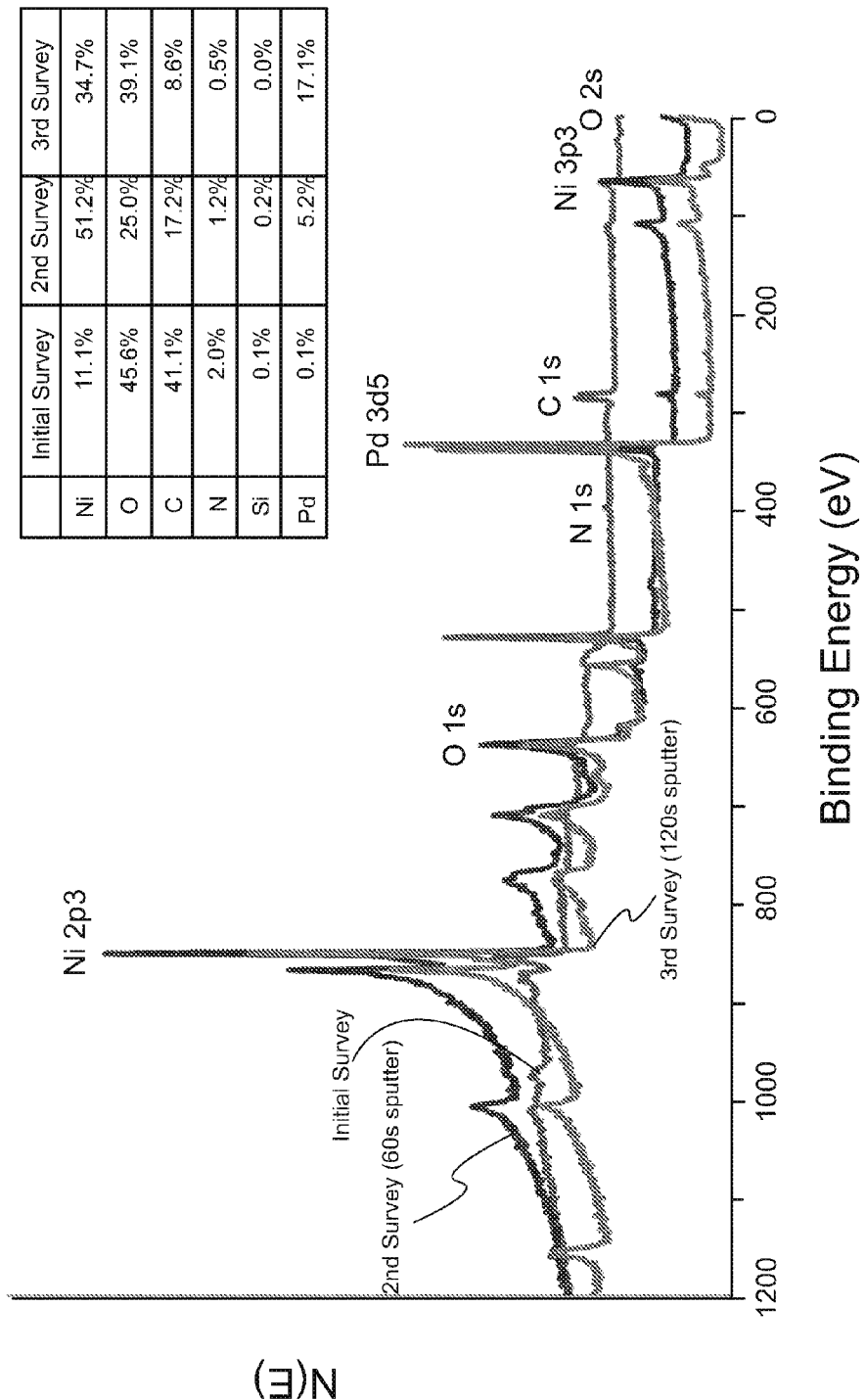
FIG. 15 provides XPS survey scans of a 32 nm nickel film deposited on Pd at 150° C. formed from $Ni(dmap)_2$.
Figure 16:
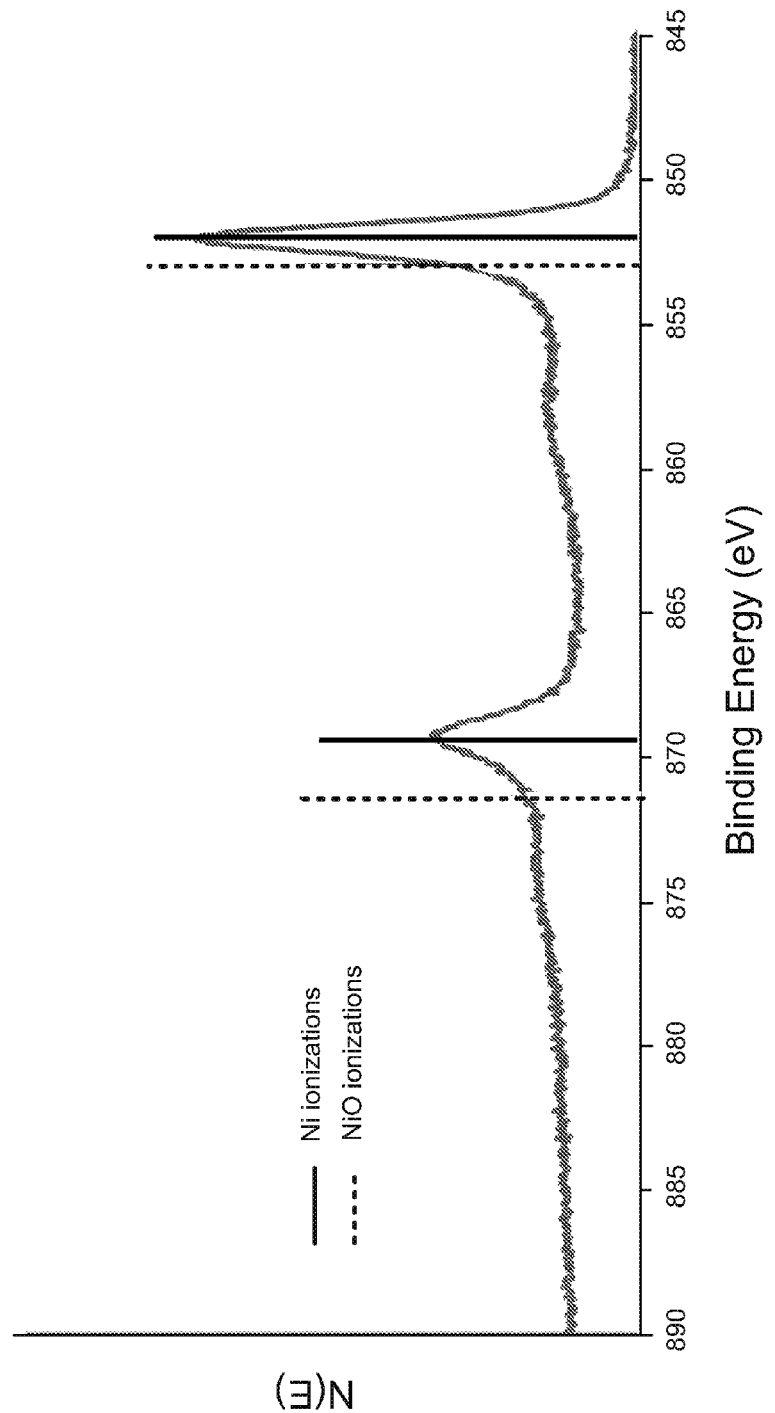
FIG. 16 provides an XPS high-resolution multiplex of the Ni 2p3 region of a film formed from $Ni(dmap)_2$.
Figure 17:
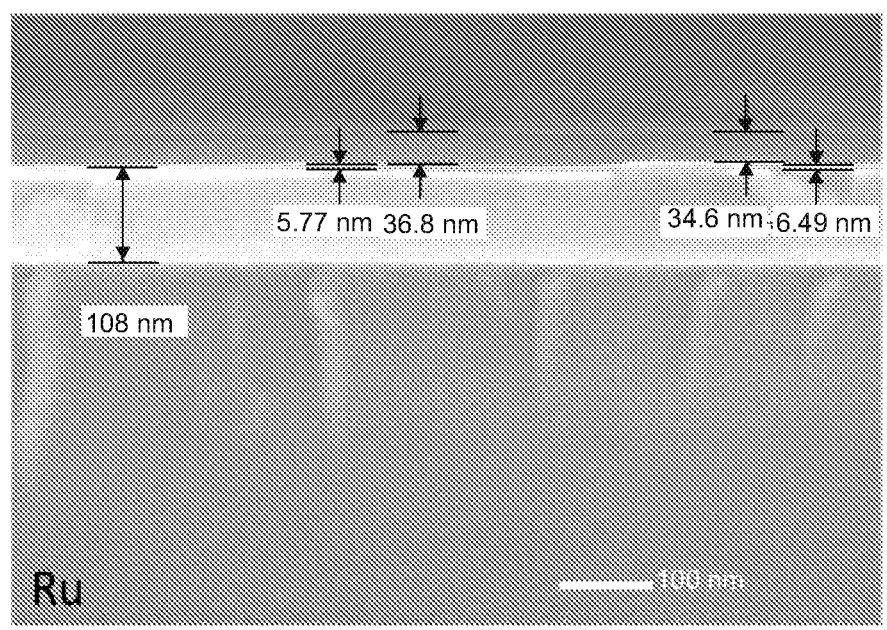
FIG. 17 provides a cross-sectional SEM micrograph of a chromium film on a $Ru/SiO_2$ substrate formed from $Cr(dad^{tBu2})_2$.
Figure 18:
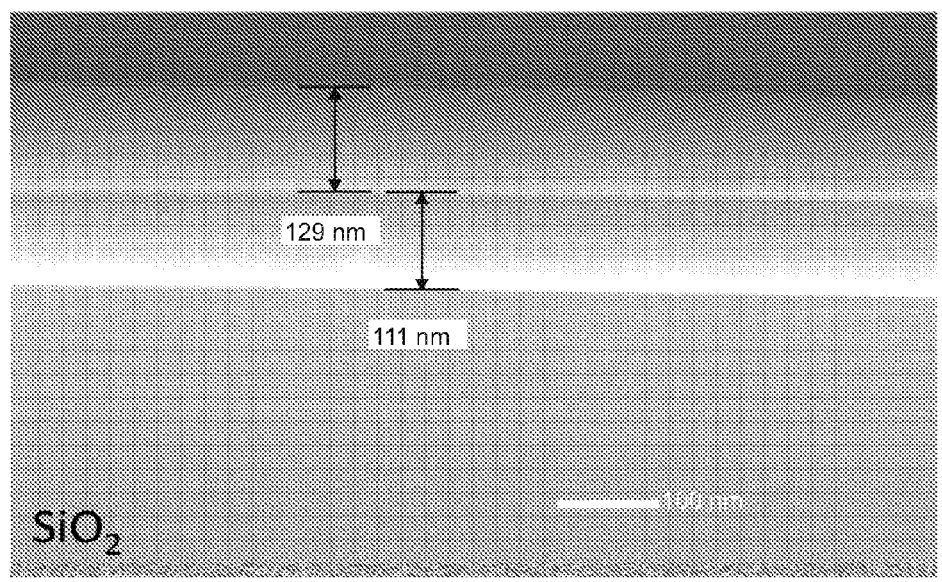
FIG. 18 provides a cross-sectional SEM micrograph of chromium film on a $SiO_2$ substrate formed from $Cr(dad^{tBu2})_2$.
Figure 19:
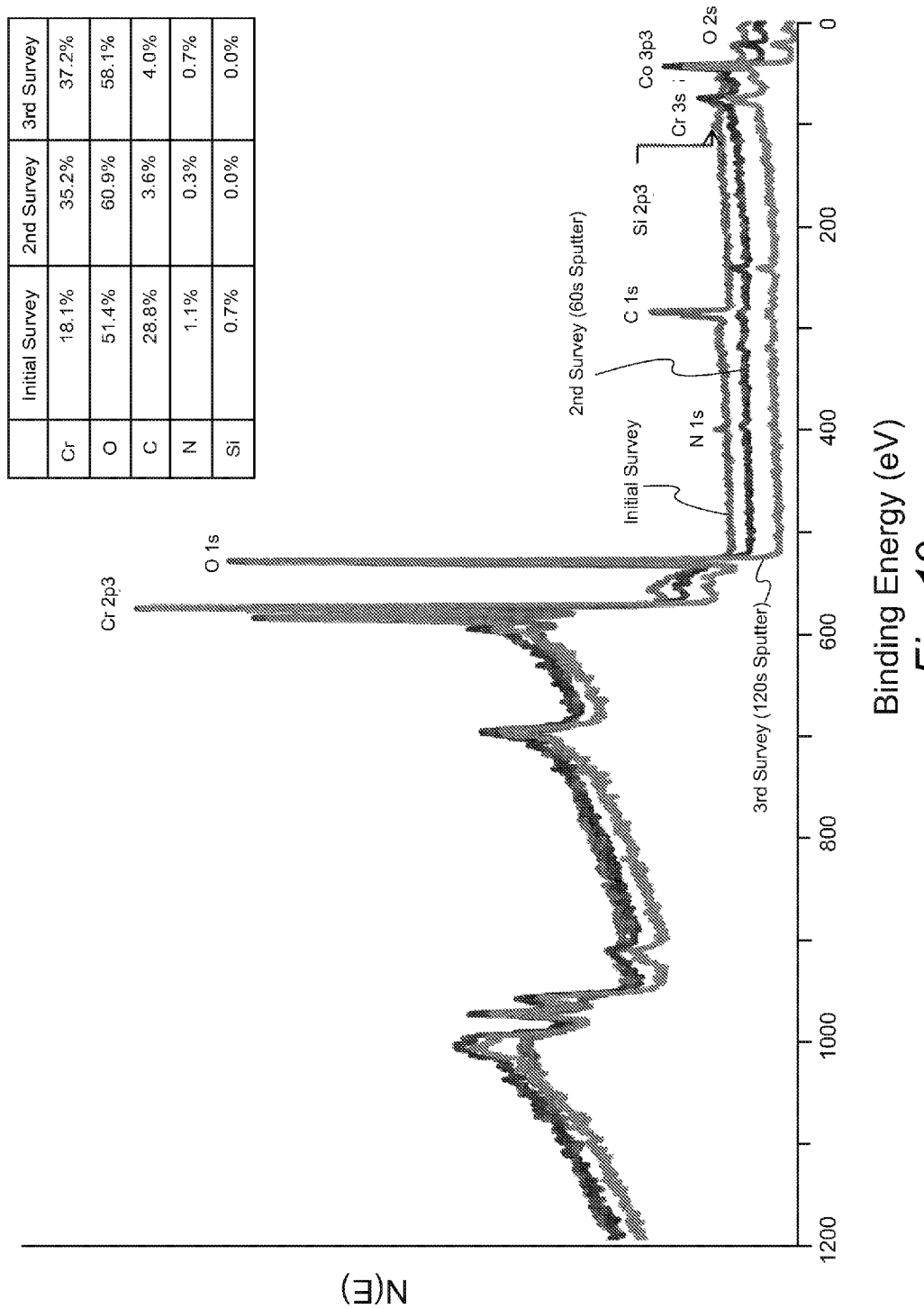
FIG. 19 provides XPS survey scnas of a 124 nm thick chromium film deposited on thermal $SiO_2$ at 225° C. formed from $Cr(dad^{tBu2})_2$.
Figure 20:
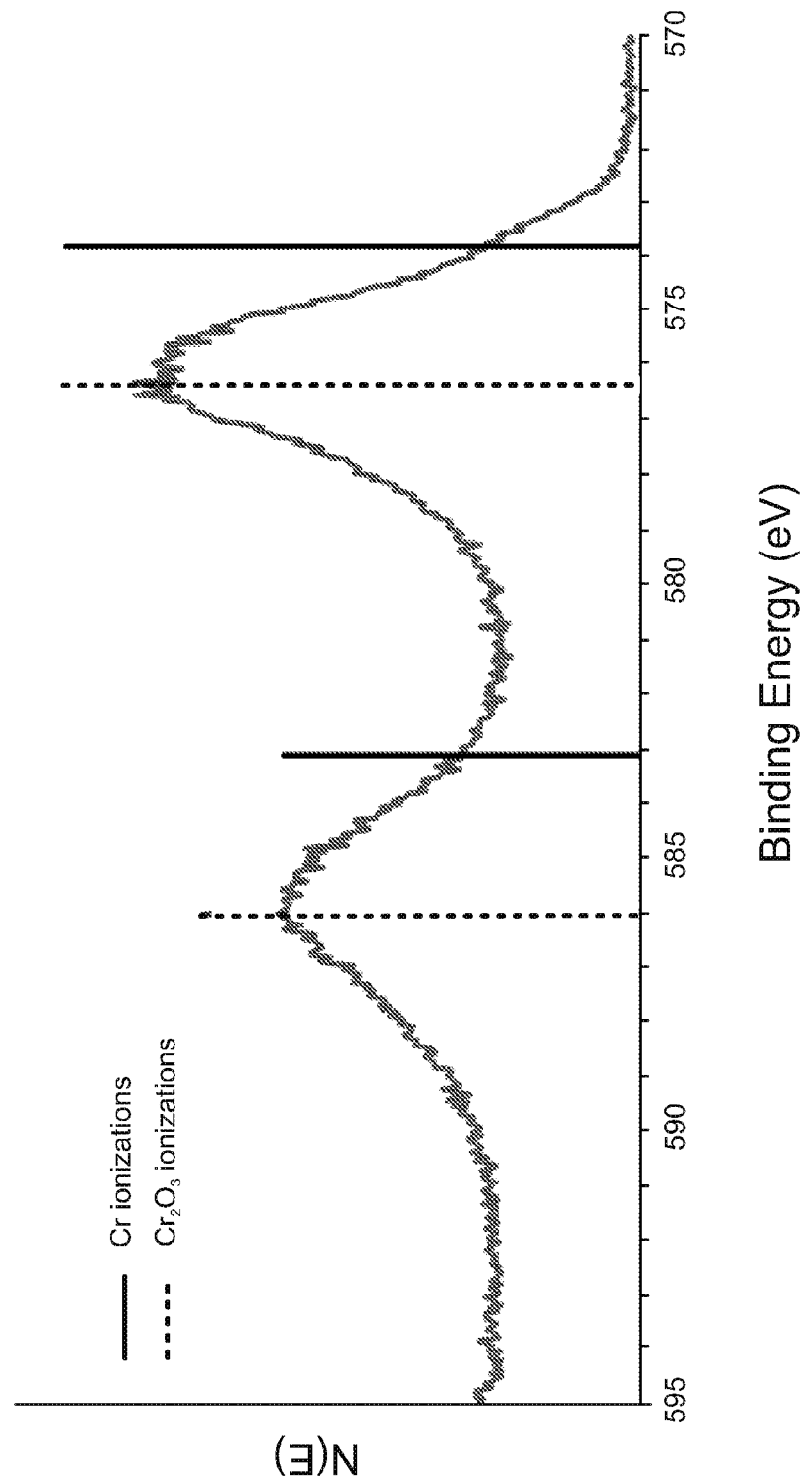
FIG. 20 provides an XPS high-resolution multiplex of the Cr 2p3 region of a film formed from $Cr(dad^{tBu2})_2$.
Figure 21:
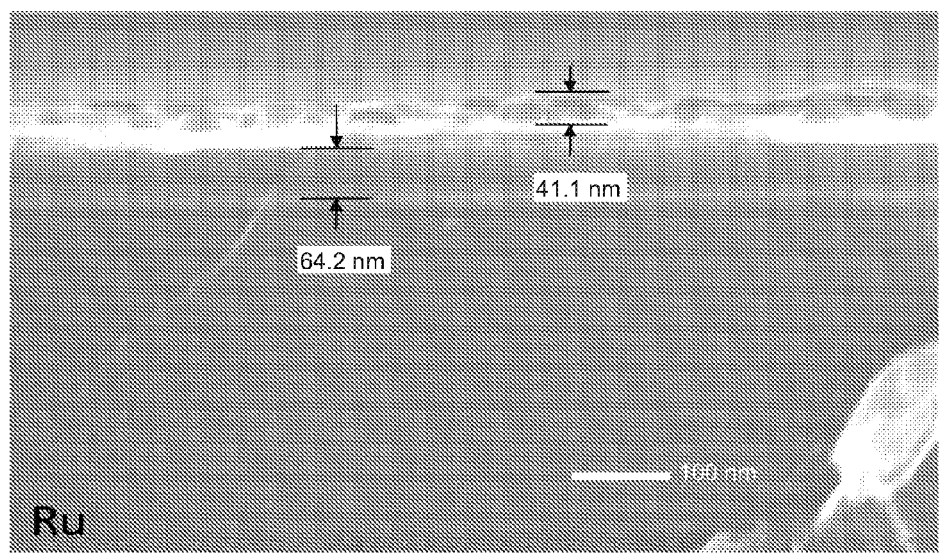
FIG. 21 provides a cross-sectional SEM micrograph of a manganese film on a $Ru/SiO_2$ substrate formed from $Mn(dad^{tBu2})_2$.
Figure 22:
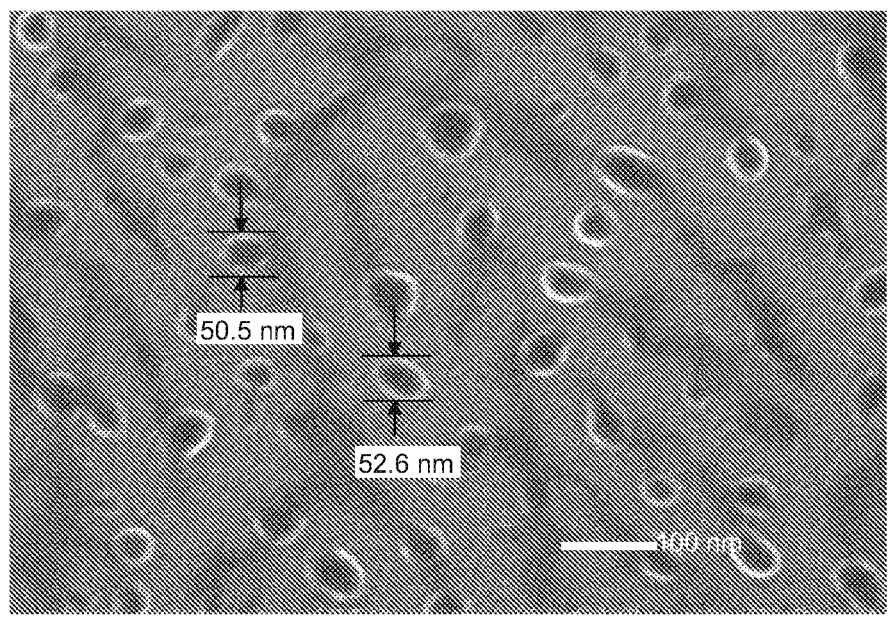
FIG. 22 provides a top-down SEM micrograph of a manganese film on a $Ru/SiO_2$ substrate formed from $Mn(dad^{tBu2})_2$.
Figure 23:
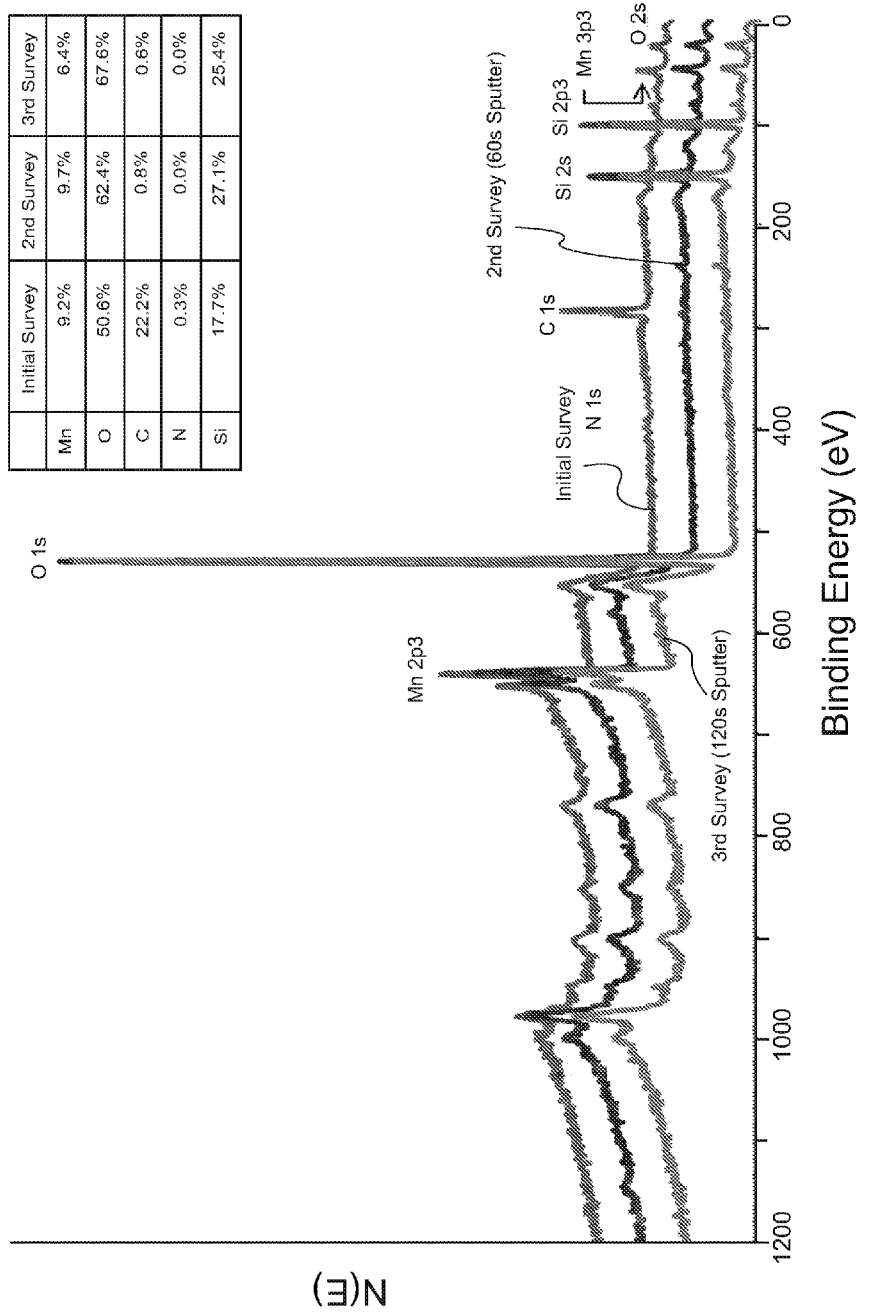
FIG. 23 provides XPS survey scans of a 27 nm manganese film deposited on $SiO_2$ at 225° C. formed from $Mn(dad^{tBu2})_2$.
Figure 24:
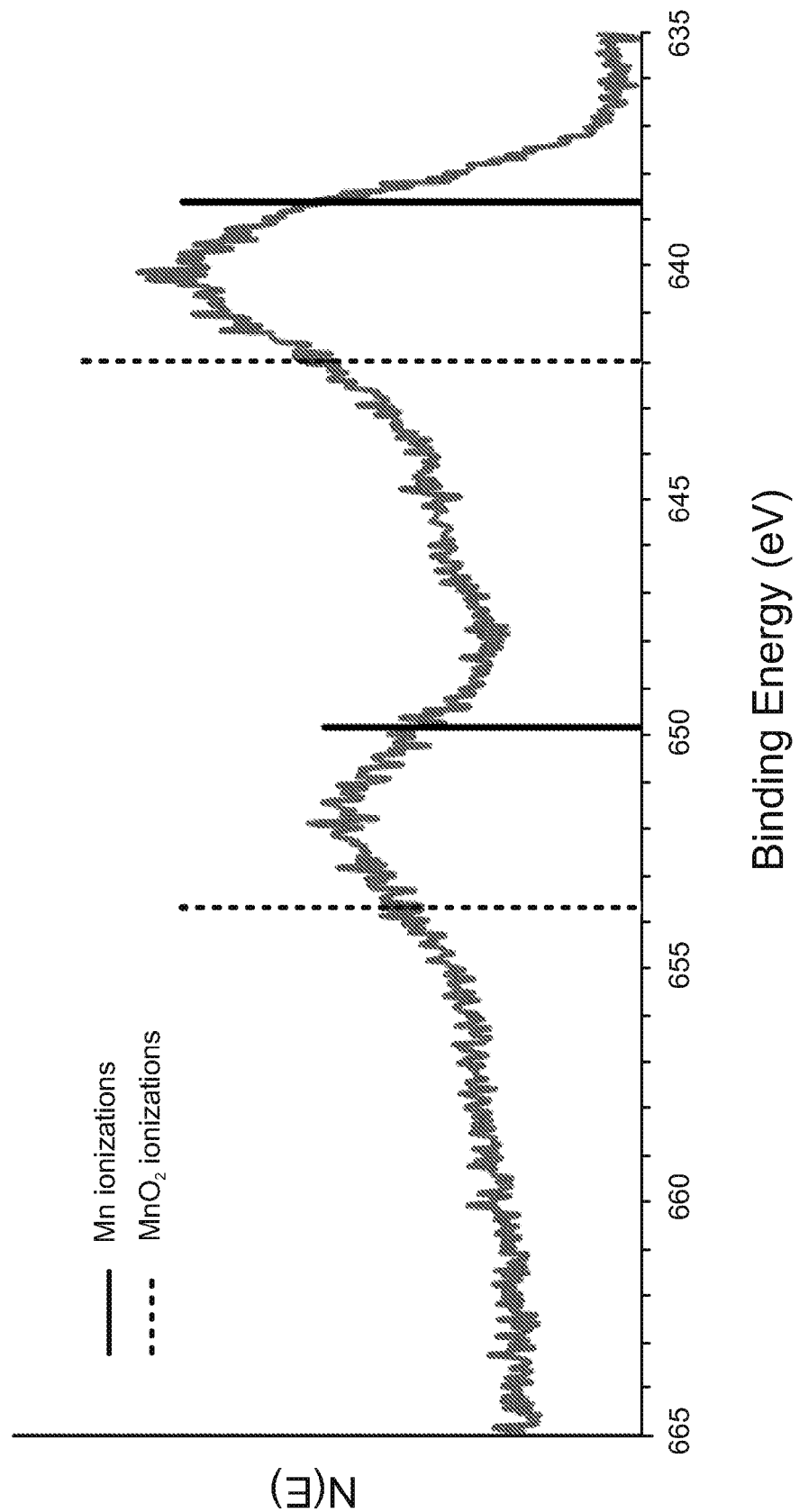
FIG. 24 provides an XPS high-resolution multiplex of the Mn 2p3 region of a film formed from $Mn(dad^{tBu2})_2$.
Figure 25:
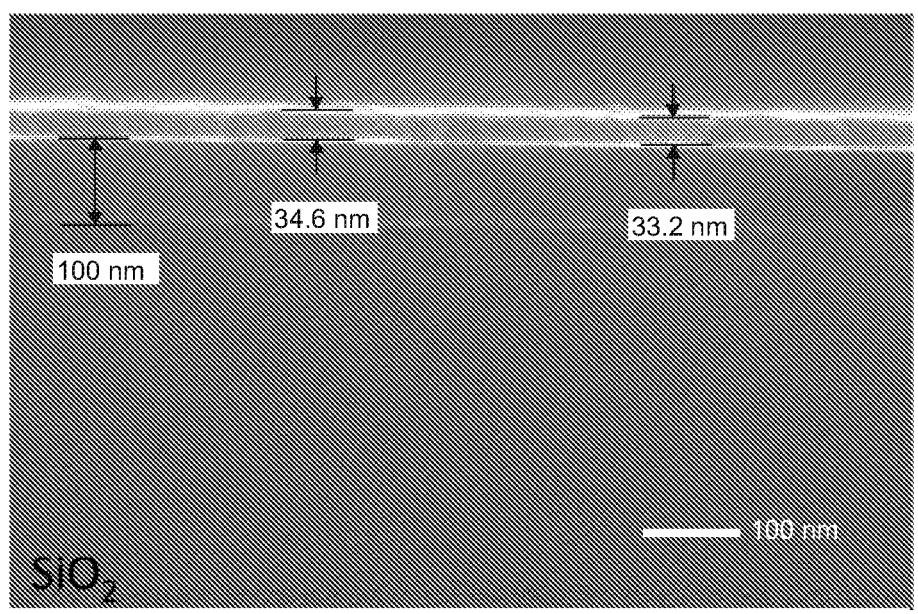
FIG. 25 provides a cross-sectional SEM micrograph of an iron film on a thermal $SiO_2$ substrate formed from $Fe(dad^{tBu2})_2$.
Figure 26:
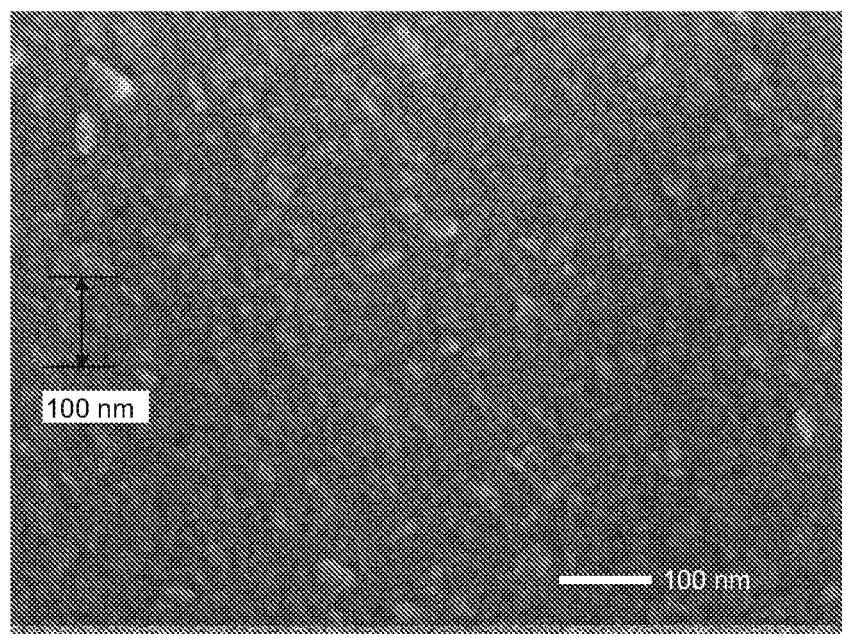
FIG. 26 provides a top-down SEM micrograph of an iron film on thermal $SiO_2$ formed from $Fe(dad^{tBu2})_2$.
Figure 27:
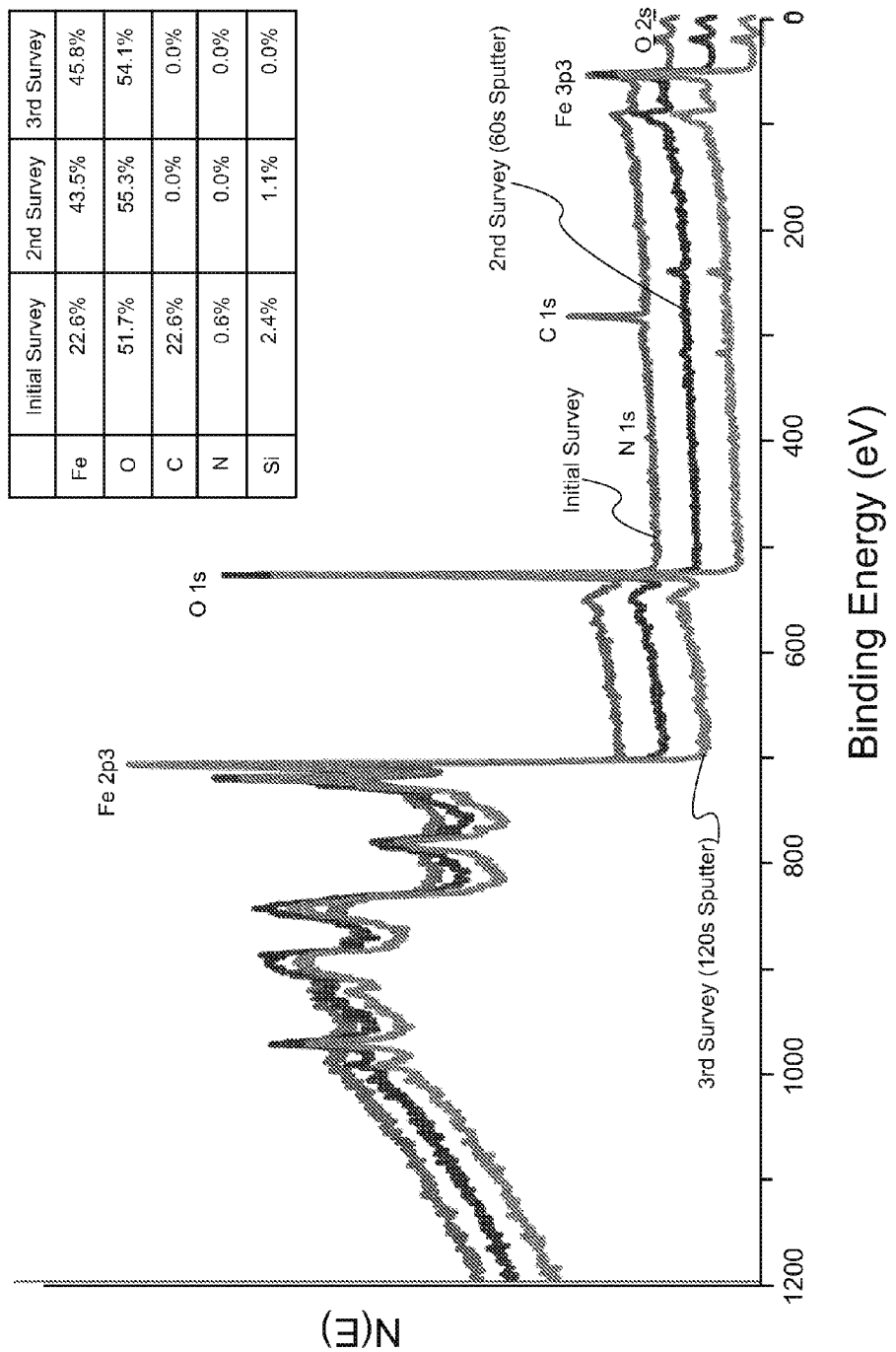
FIG. 27 provides XPS survey scans of a 35 nm thick iron film deposited on $Ru/SiO_2$ at 225° C. formed from $Fe(dad^{tBu2})_2$.
Figure 28:
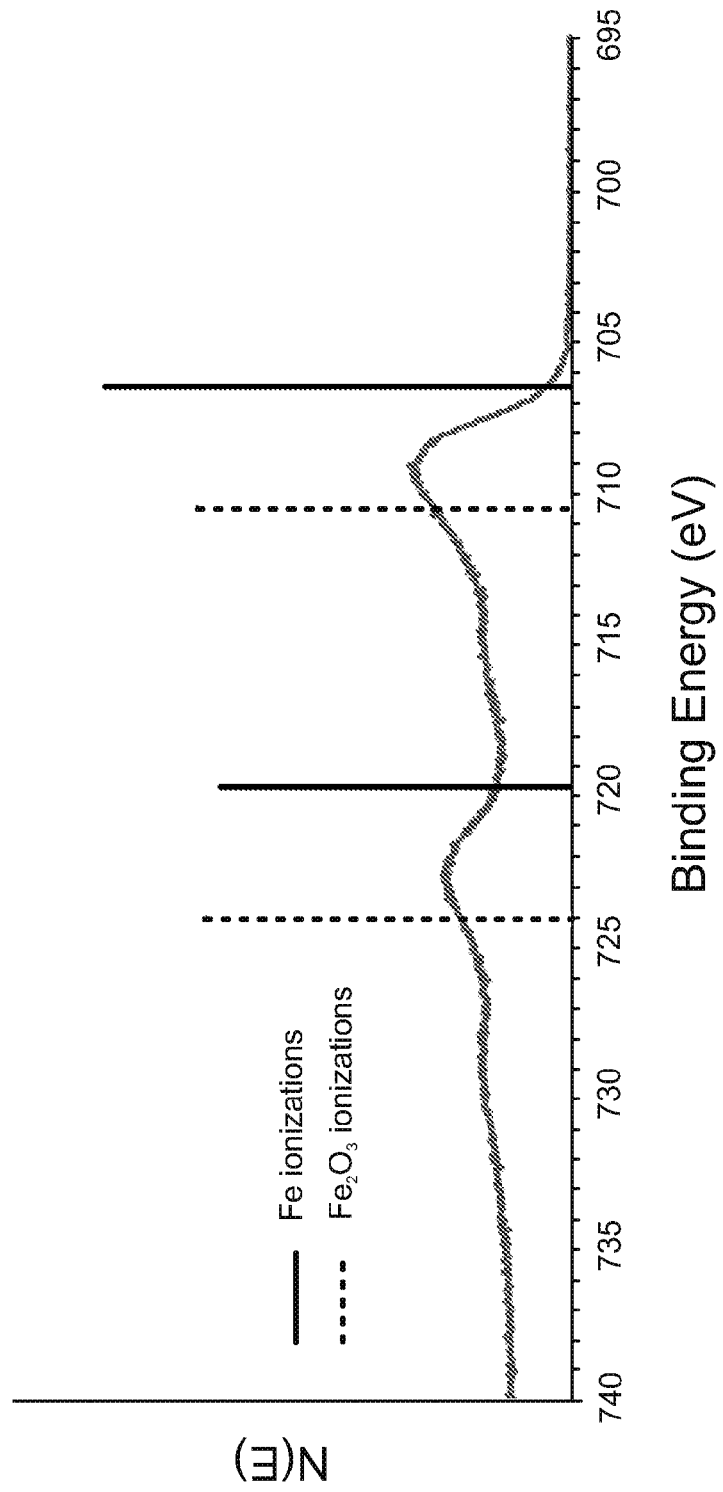
FIG. 28 provides an XPS high-resolution multiplex of the Fe 2p3 region of a film formed from $Fe(dad^{tBu2})_2$.
Figure 29:
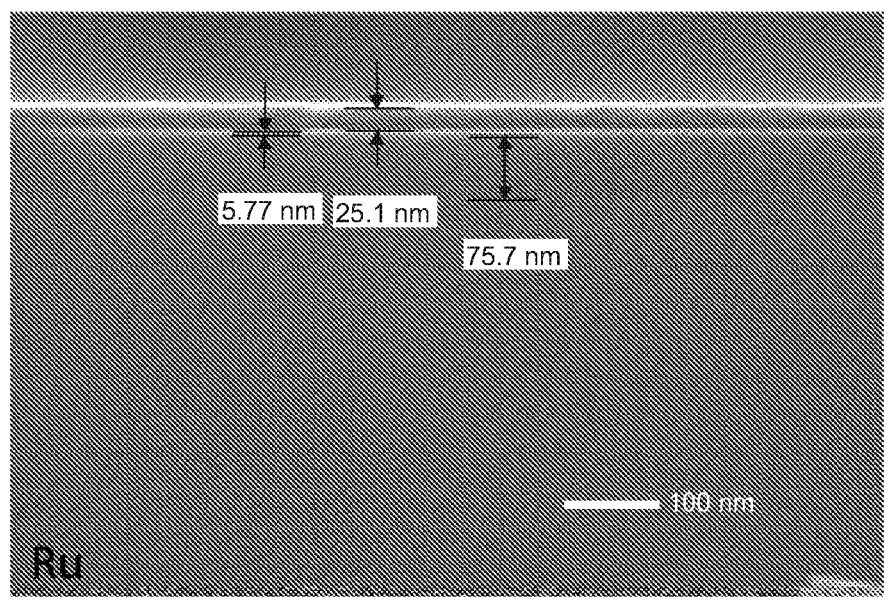
FIG. 29 provides a cross-sectional SEM micrograph of a cobalt film on a $Ru/SiO_2$ substrate formed from $Co(dad^{tBu2})_2$.
Figure 30:
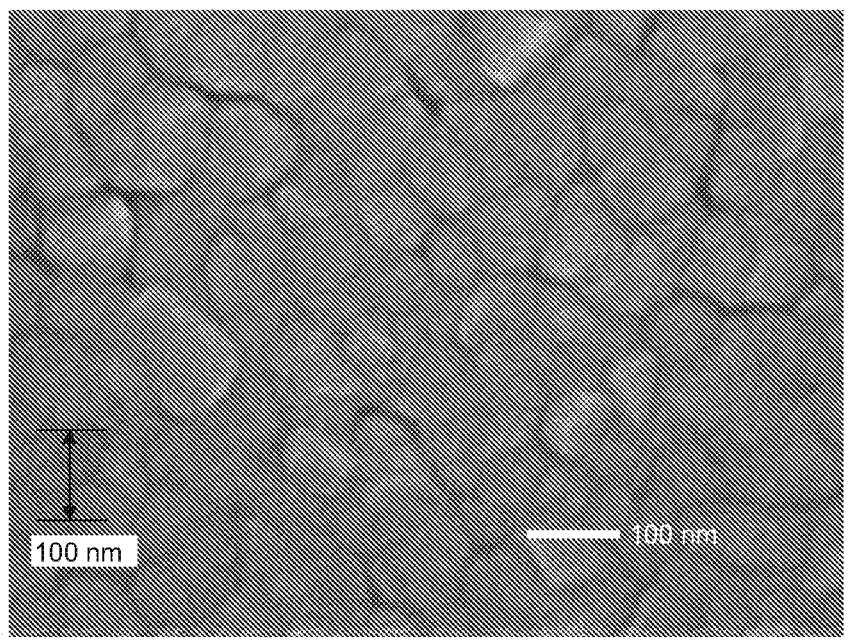
FIG. 30 provides a top-down SEM micrograph of a cobalt film on a thermal $SiO_2$ substrate formed from $Co(dad^{tBu2})_2$.
Figure 31:
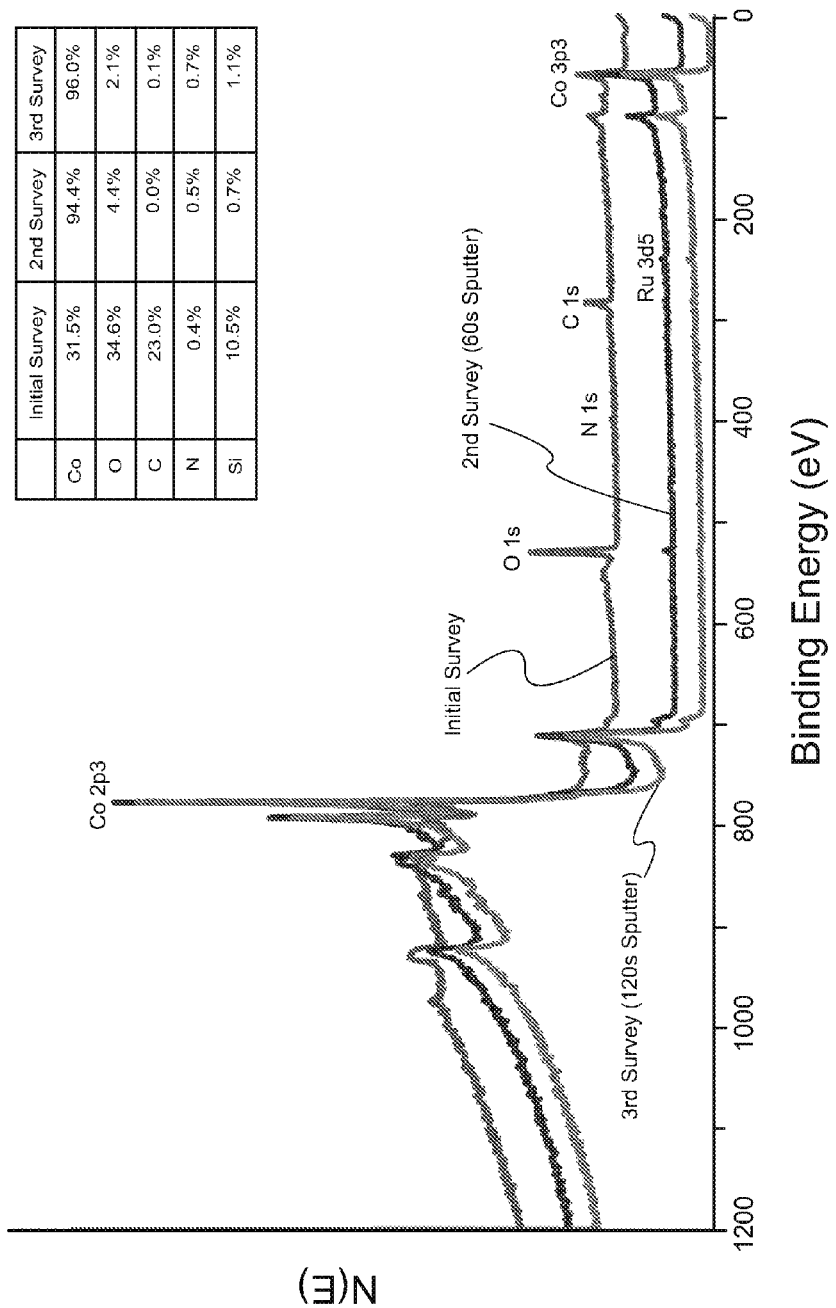
FIG. 31 provides XPS survey scans of a 24 nm thick cobalt film deposited on $Ru/SiO_2$ at 180° C. from $Co(dad^{tBu2})_2$.
Figure 32:
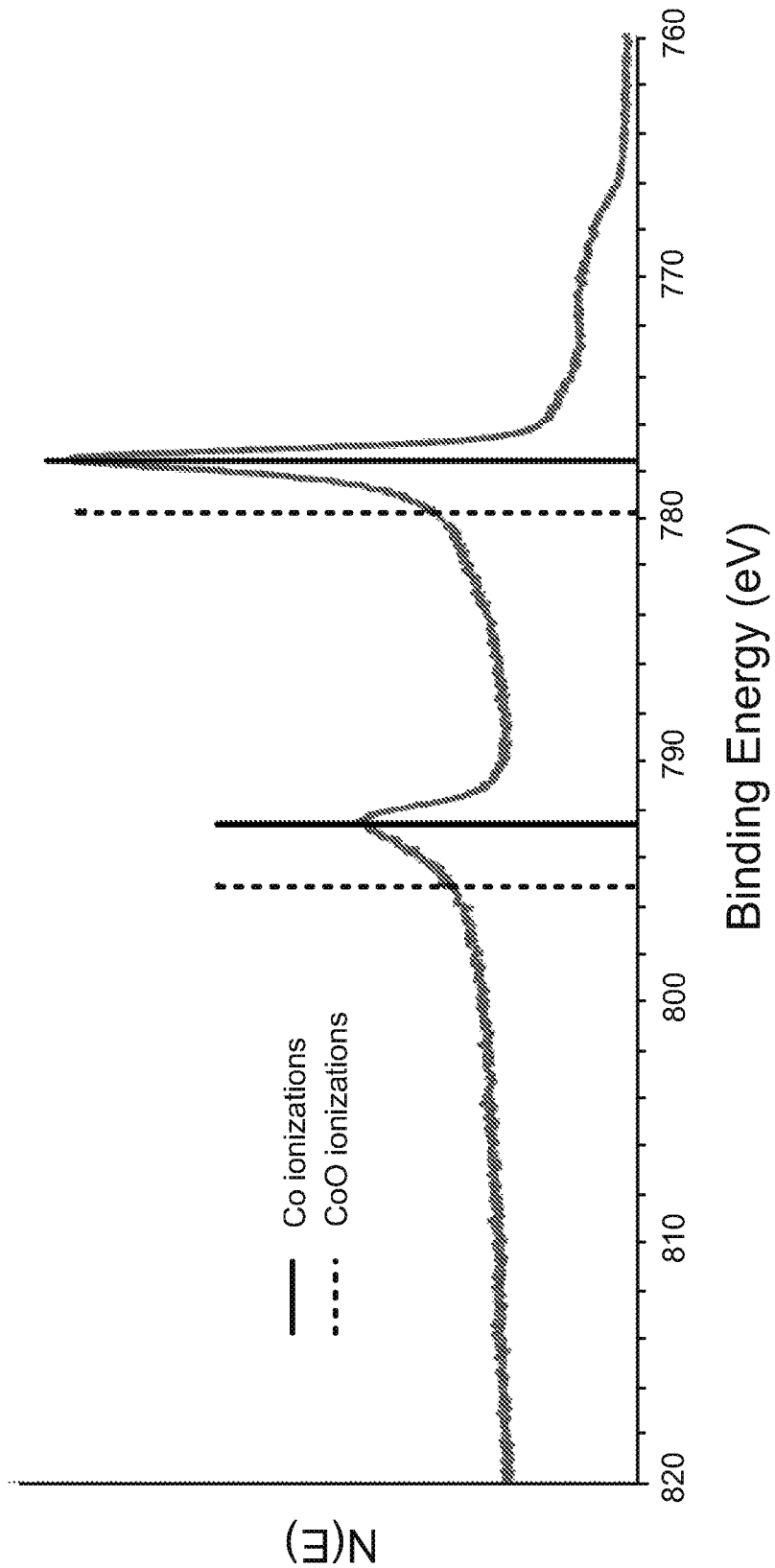
FIG. 32 provides an XPS high-resolution multiplex of the Co 2p3 region of a film formed from $Co(dad^{tBu2})_2$.
Figure 33:
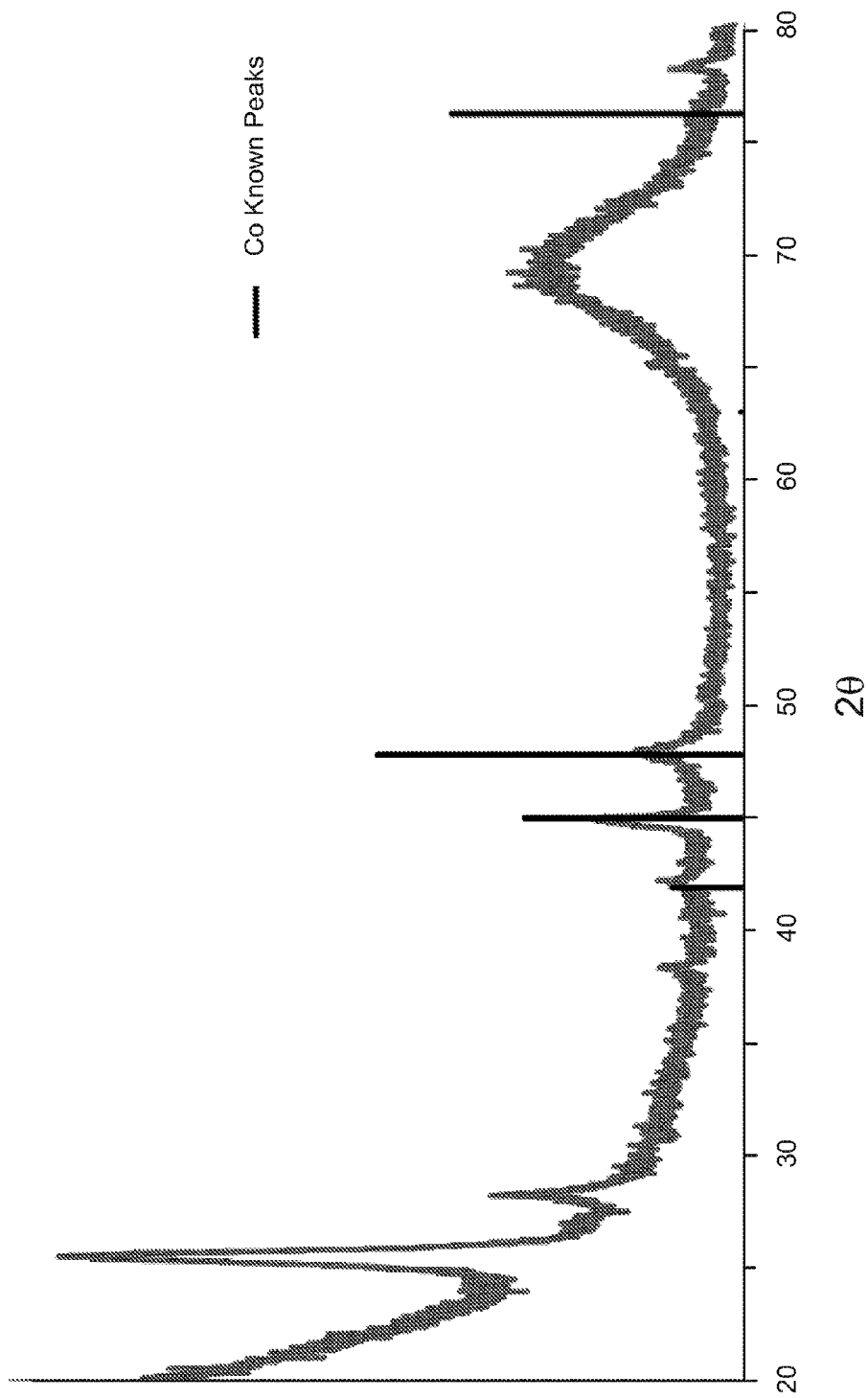
FIG. 33 provides an X-ray diffraction spectrum of showing cobalt metal on a $SiO_2$ substrate formed from $Co(dad^{tBu2})_2$.
Figure 34:
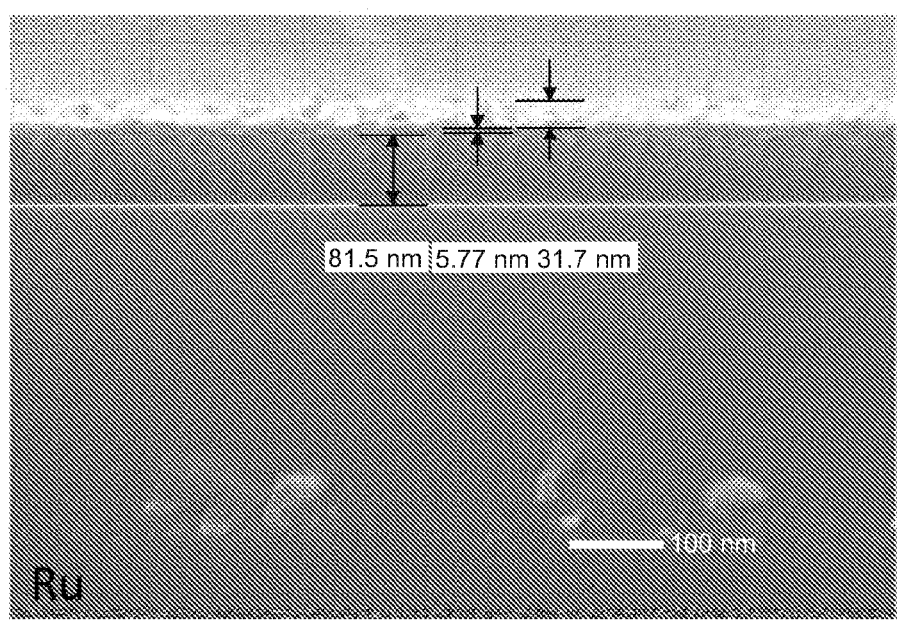
FIG. 34 provides a cross-sectional SEM micrograph of a nickel film on a $Ru/SiO_2$ substrate formed from $Ni(dad^{tBu2})_2$.
Figure 35:
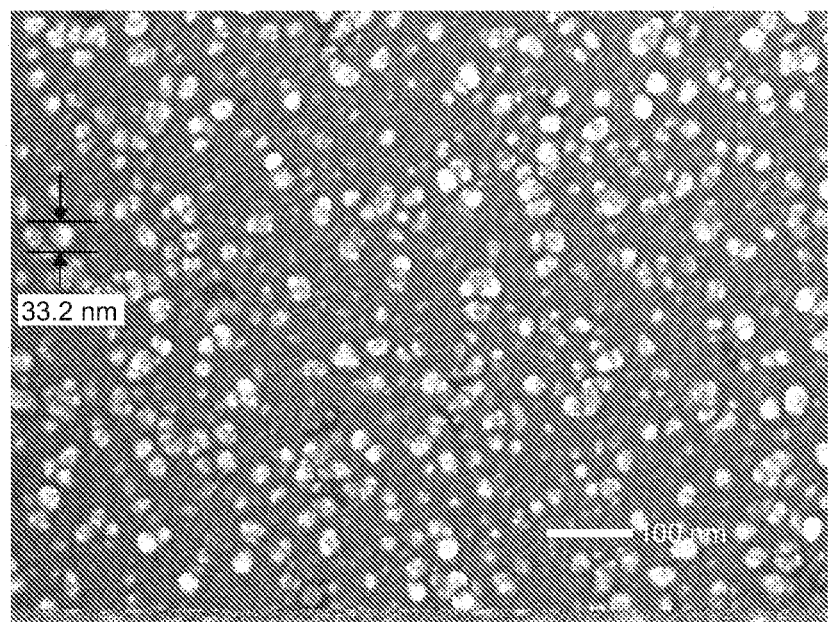
FIG. 35 provides a top-down SEM micrograph of a nickel film on a copper substrate formed from $Ni(dad^{tBu2})_2$.
Figure 36:
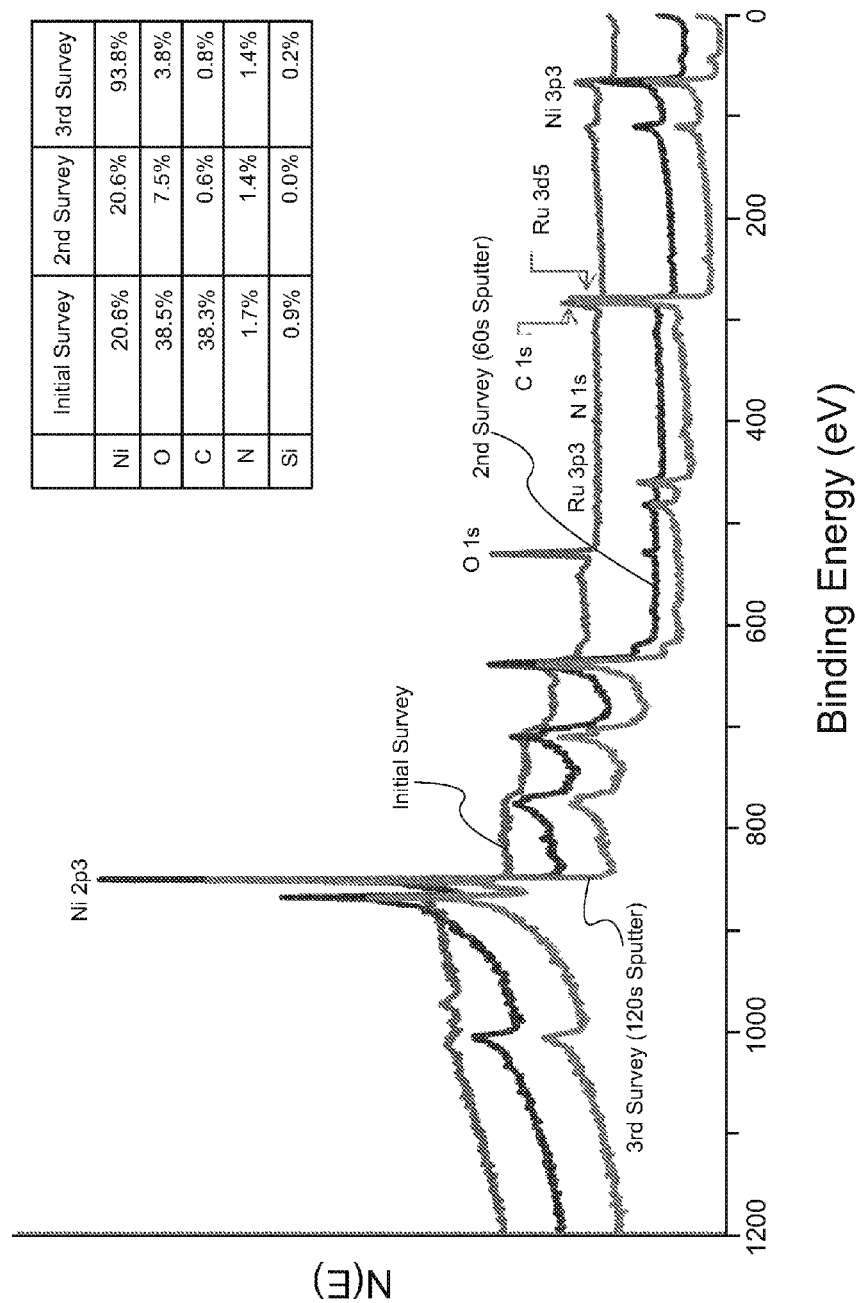
FIG. 36: provides XPS survey scans of a 34 nm thick nickel film deposited on $Ru/SiO_2$ at 180° C. from $Ni(dad^{tBu2})_2$.
Figure 37:
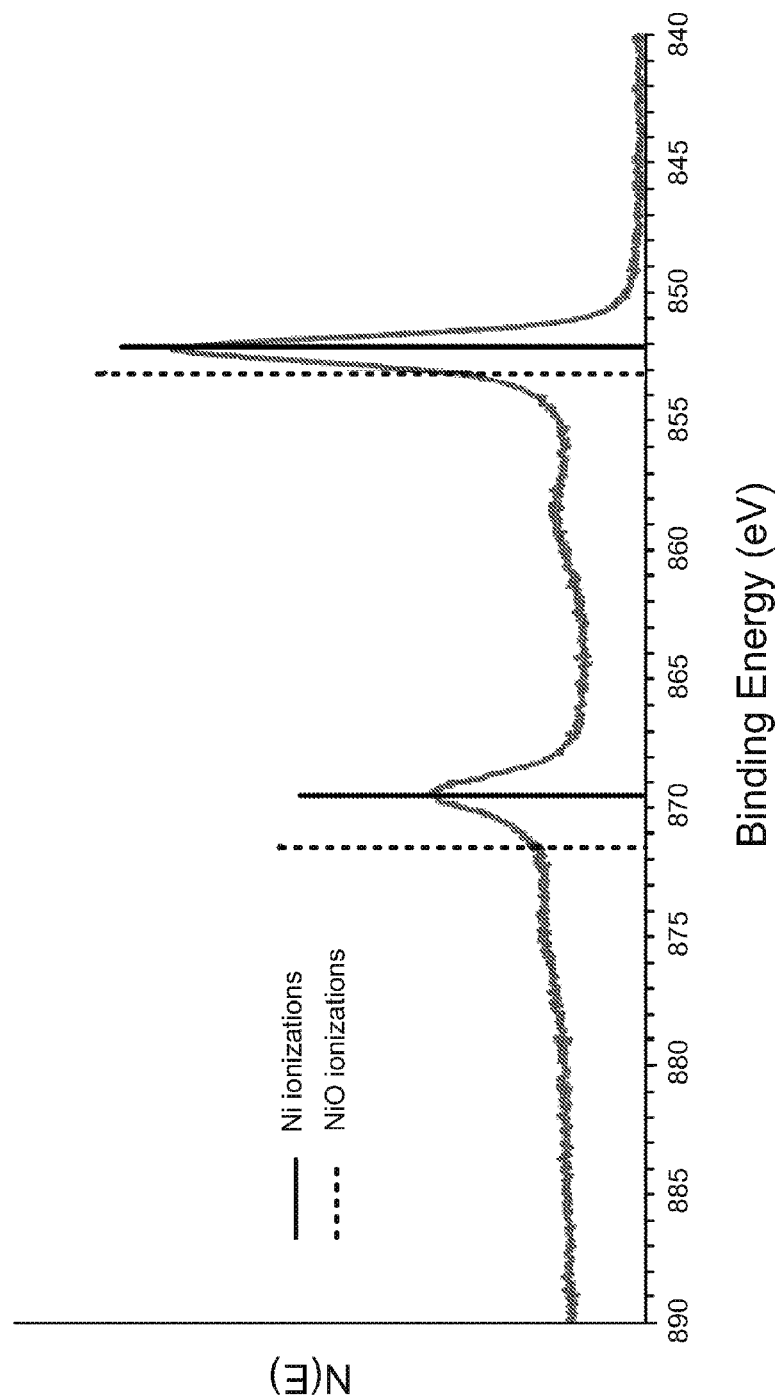
FIG. 37: provides an XPS high-resolution multiplex of the Ni 2p3 region for a film formed from $Ni(dad^{tBu2})_2$.

Solution reactions were conducted with a variety of metal salts in THF. Upon refluxing with DHP, precipitate formation was observed from Cu, Ni, Co, Fe, Zn, and Cr salts (Table 3). Copper precipitate was observed as regions of copper-colored film on the flask and metallic flakes in solution, while cobalt and iron precipitated out as the ferromagnetic metals, sticking to the stir bar. The precipitate resulting from the reaction of copper bis(2,2,6,6-tetramethyl-3,5-heptanedionate) [Cu(tmhd)₂] with DHP was identified as copper metal by XRD (FIG. 8).

TABLE 3

Reaction matrix of metal salts with DHP

| | | Reaction | | Reflux | | |
|---|---|---|---|---|---|---|
| $ML_2$ | THF | Temp | Time (min) | Temp | Time (min) | Reaction solution → Precipitate |
| Cu(dmap)₂ | 50 ml | RT | 15 | 65° C. | 60 | Cu flakes; Cu & green residue on flask |
| Cu(tmhd)₂ | 70 ml | RT | 30 | 65° C. | 95 | Cu & green flakes; Cu & purple residue on flask |
| NiCl₂ | 50 ml | RT | 15 | 65° C. | 70 | Tan powder |
| CoCl₂ | 40 ml | RT | 35 | 65° C. | 60 | Dark green powder at RT (sticks to stir bar) |
| FeCl₂ | 60 ml | RT | 35 | 65° C. | 60 | Film on flask; black powder (sticks to stir bar) |
| ZnCl₂ | 75 ml | RT | 15 | 65° C. | 60 | Few metallic flakes → white precipitate after about 3 days |
| CrCl₂ | 70 ml | RT | 23 | 65° C. | 60 | Silver-colored flakes → grey suspension |
| MnCl₂ | 50 ml | RT | 15 | 65° C. | 60 | None |

A binary process using Cu(dmap)₂ and DHP at 150° C. failed to produce films on any substrates (Si(100), SiH, thermal SiO₂, Cu, Pt, Pd, TiN, and Ru/SiO₂, Co/SiO₂). A three-step process was subsequently attempted, whereby formic acid was used to produce the metal formate, which was then reduced to copper metal by 1,4-bis(trimethylsilyl)-1,4-dihydropyrazine. Subsequent applications of this general approach used numerous metal precursors, including Cu and Ni(dmap)₂ and various metal 1,4-di-tert-butyldiazadiene complexes [M(dad$^{tBu2}$)₂]. Each deposition cycle consisted of a precursor pulse (3.0 s for M(dmap)₂ and 6.0 s for M(dad$^{tBu2}$)₂), a 5.0 s purge, a 0.2 s pulse of formic acid, a 5.0 s purge, a 1.0 s pulse of DHP, and a final 10.0 s purge. Delivery temperatures were maintained at 100° C. and 150° C. for M(dmap)₂ and M(dad$^{tBu2}$)₂ precursors, respectively. Delivery temperatures were maintained at 70° C. and 21° C. for DHP and formic acid, respectively. Selected films from each deposition were characterized by SEM, XRD, and XPS as provided by FIGS. 9-37.

Aluminum and Titanium Experimental Section

Figure 38:
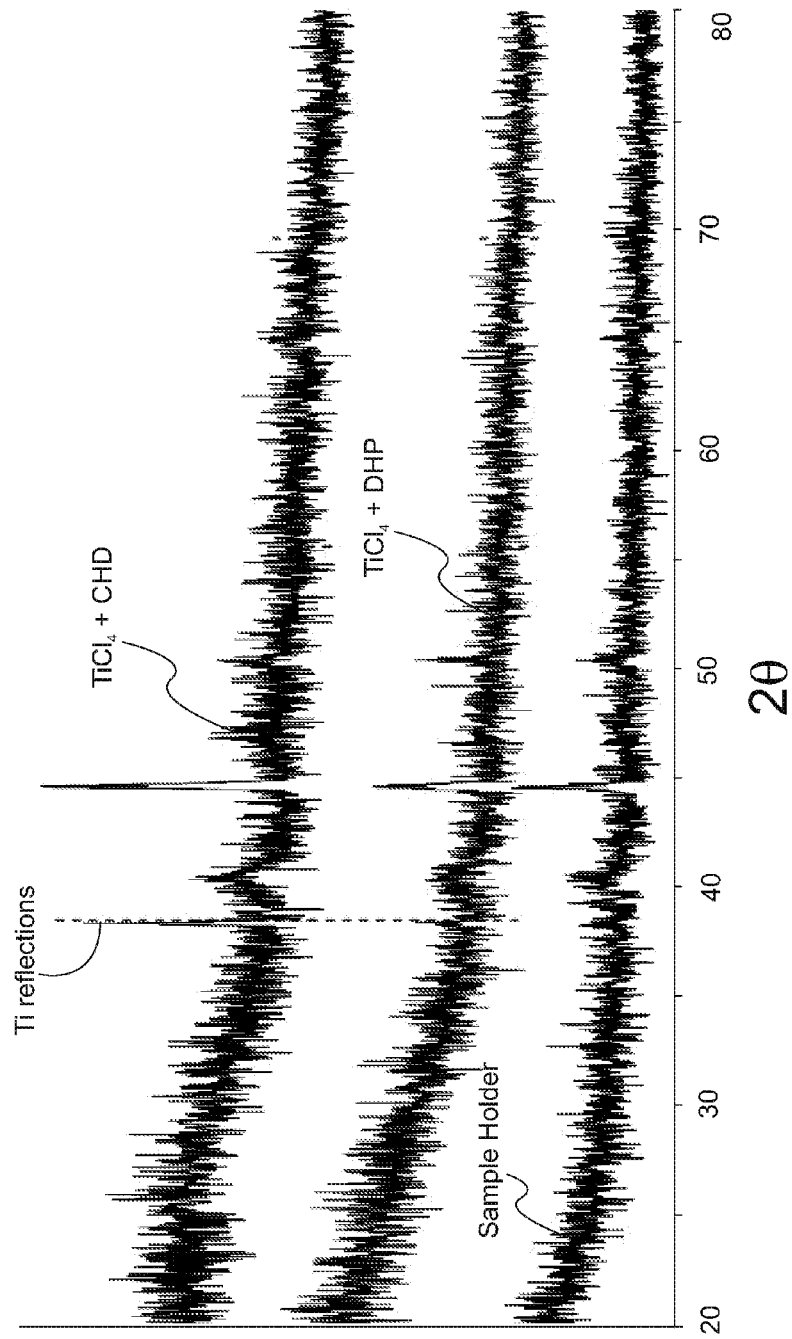
FIG. 38 provides X-ray diffraction (XRD) spectra for solution reaction precipitates formed from the reaction with titanium tetrachloride and CHD (e.g., formula IA) and titanium tetrachloride and DHP (e.g., formula IB)

Solution Screening Experiments:
$TiCl_4$+CHD $TiCl_4$ was reacted with a 2.5 molar excess of CHD in toluene. Upon addition of the $TiCl_4$ to the CHD solution, the mixture turned a dark rust-brown color with a dark precipitate. The mixture was stirred at ambient temperature for ~24 hrs. The solvent was removed under vacuum using a hot water bath. XRD analysis of the precipitate powder showed the major reflection of Ti metal ($2\theta$=38.4°, FIG. 38).
$TiCl_4$+DHP $TiCl_4$ was reacted with a 2.6 molar excess of DHP in toluene. $TiCl_4$ dissolved in toluene yielding a clear bright orange-colored solution. Upon addition of DHP, the solution immediately turned black with a very dark green/black precipitate. The mixture was stirred for ~24 hrs at ambient temperature. The solvent was removed under vacuum using a hot water bath. A small peak in the XRD spectrum matched that for the major reflection of Ti metal ($2\theta$=38.48, FIG. 38). FIG. 38 provides XRD patterns for solution reaction precipitates formed from the reaction with $TiCl_4$ and CHD and $TiCl_4$ and DHP. The spectra show peaks corresponding to titanium metal, thereby verifying the formation of titanium metal in the zero oxidation state.
$SiCl_4$+DHP DHP completely dissolved in 40 mL of toluene, yielding a yellow solution. $SiCl_4$ was directly added to the DHP solution, immediately producing a very faint white cloudiness near the bottom of the flask. The mixture was stirred at ambient temperature for ~72 hrs. A white precipitate was allowed to settle to the bottom of the flask. The solvent was removed under vacuum using a hot water bath. The yellow solution became increasingly dark as the solvent was removed; approximately 2-3 mL of liquid remained that would not evaporate. The remaining dark yellow slurry immediately turned brown upon air exposure. XRD analysis of the powder did not show any identifiable reflections.

ALD Deposition Experiments:
$TiCl_4$+CHD

Titanium film growth was demonstrated using $TiCl_4$+CHD. Each cycle consisted of a 0.2 s pulse of $TiCl_4$, a 15.0 s purge, a 1.0 s pulse of CHD, and a 10.0 s purge. The $TiCl_4$ bubbler was maintained at 20° C. and the reaction chamber was held at 180° C. The temperature of the solid state booster for CHD delivery was set to 75° C. After 1,000 cycles, definitive films were observed on Pd, Pt, and $SiO_2$ with growth rates of approximately 0.09 Å/cycle, 0.15 Å/cycle, and 0.08 Å/cycle, respectively. Discontinuous (island-type) growth was observed by SEM on the Co substrate. Faint films were observed on the Ru and Cu substrates; their presence was confirmed by SEM analysis.

As used herein for the ALD experiments, platinum substrates consist of silicon substrates with a thermal oxide over coated with a platinum layer. Palladium substrates consist of silicon substrates with a thermal oxide over coated with a palladium layer. Cobalt substrates consist of silicon substrates with a thermal oxide over coated with a cobalt layer. It should be appreciated that SEM cross-sections are not able to distinguish the metal coating the substrate and the ALD film deposited thereon.

Figure 39:
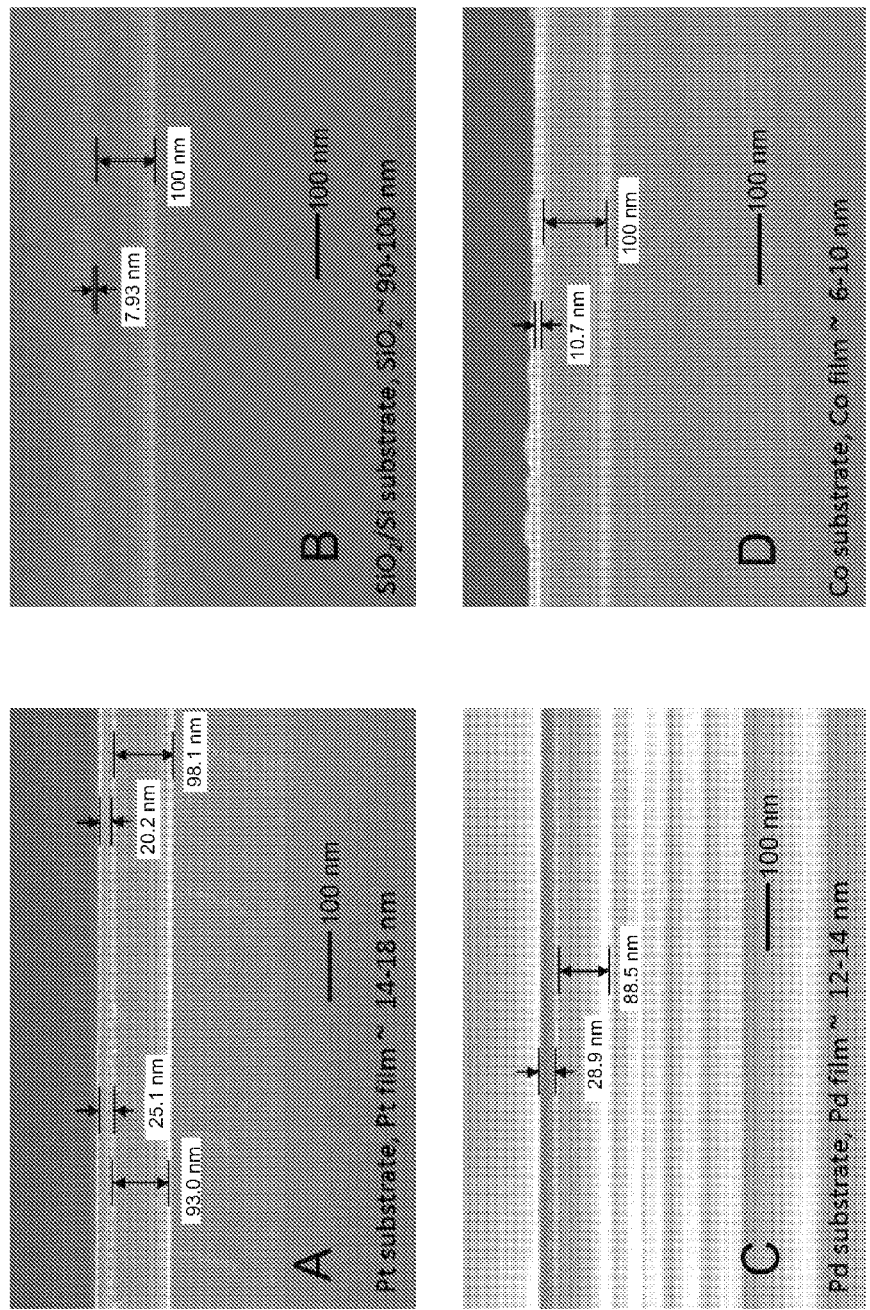
FIG. 39A provides an SEM cross-section for an ALD film deposited on a platinum substrate from the reaction with titanium tetrachloride and CHD at 180° C.
FIG. 39B provides an SEM cross-section for an ALD film deposited on a silicon substrate with a thermal silicon oxide layer from the reaction with titanium tetrachloride and CHD at 180° C.
FIG. 39C provides an SEM cross-section for an ALD film deposited on a palladium substrate from the reaction with titanium tetrachloride and CHD at 180° C.
FIG. 39D provides an SEM cross-section for an ALD film deposited on a cobalt substrate from the reaction with titanium tetrachloride and CHD at 180° C.

FIG. 39A provides an SEM cross-section for an ALD film deposited on a platinum substrate from the reaction with $TiCl_4$ and CHD at 180° C. From the micrograph, the combined platinum and titanium thickness is about 25 nm with an approximate platinum layer thickness of about 14 to 18 nm and a titanium layer thickness from 7 to 11 nm. FIG. 39B provides an SEM cross-section for an ALD film deposited on a silicon substrate with a thermal silicon oxide layer from the reaction with $TiCl_4$ and CHD at 180° C. From the micrograph, the titanium layer thickness is about 8 nm. FIG. 39C provides an SEM cross-section for an ALD film deposited on a palladium substrate from the reaction with titanium tetrachloride and CHD at 180° C. From the micrograph, the combined palladium and titanium thickness is about 29 nm with an approximate palladium layer thickness of about 12 to 14 nm and a titanium layer thickness from 15 to 17 nm. FIG. 39D provides an SEM cross-section for an ALD film deposited on a cobalt substrate from the reaction with titanium tetrachloride and CHD at 180° C. From the micrograph, the combined cobalt and titanium thickness is about 11 nm with an approximate cobalt layer thickness of about 6 to 10 nm and titanium layer thickness of about 1 to 5 nm.

Figure 40:
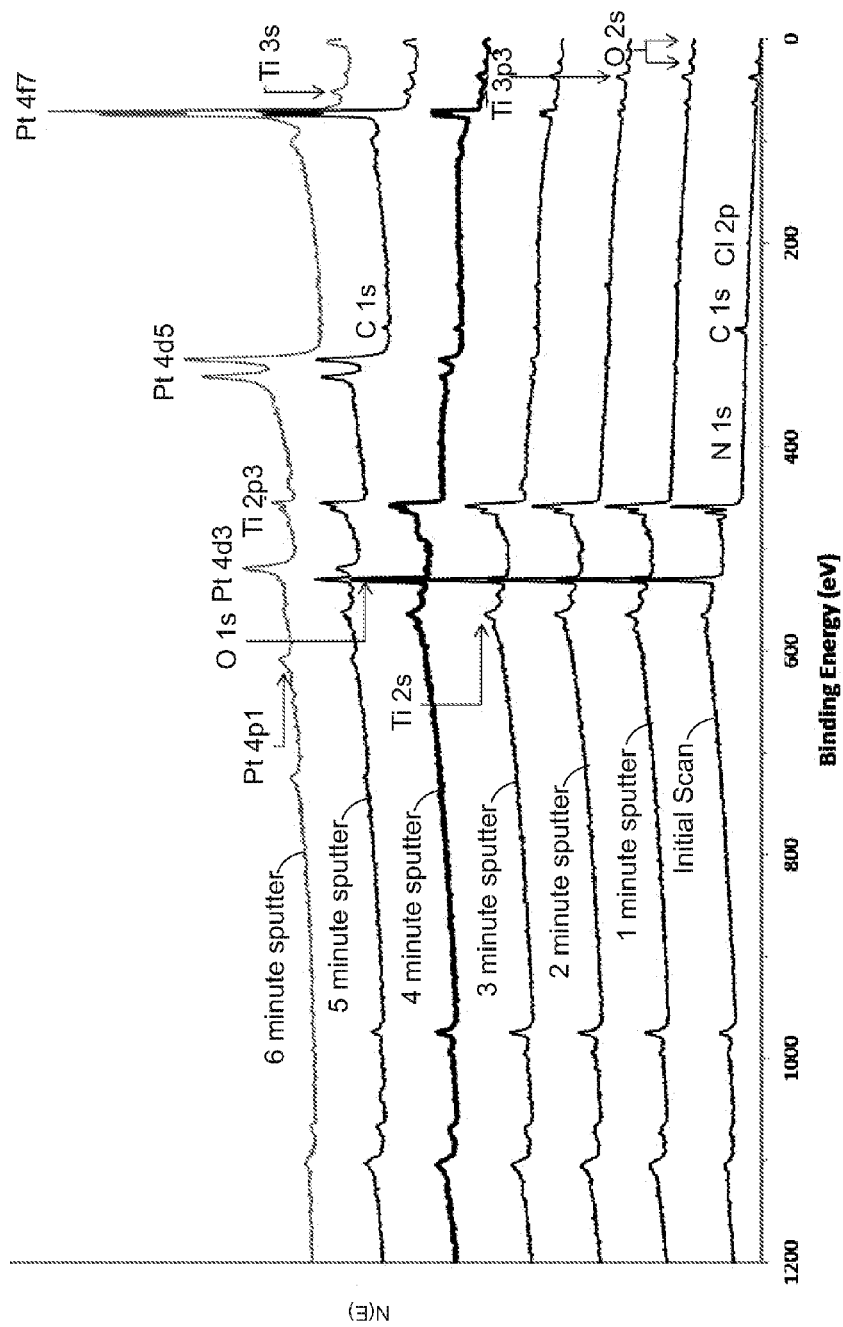
FIG. 40 provides XPS survey scans for an ALD film deposited on a platinum substrate from the reaction with titanium tetrachloride and CHD at 180° C.
Figure 41:
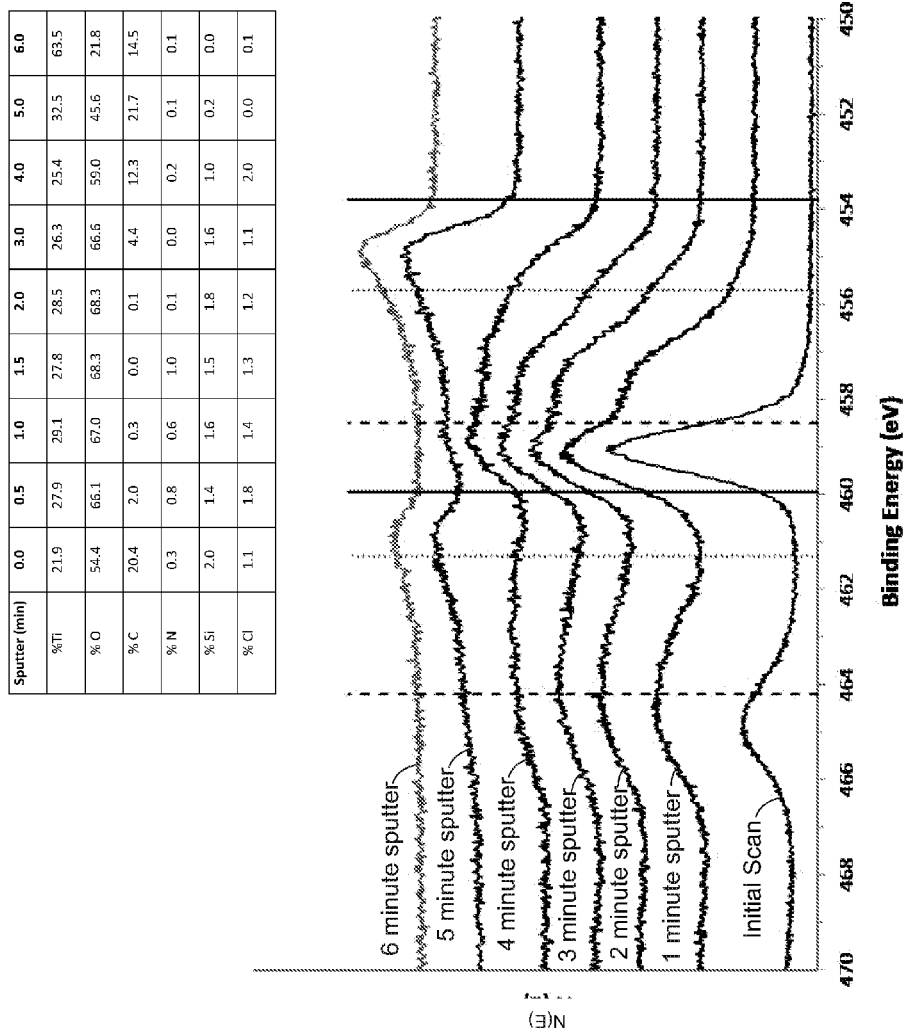
FIG. 41 provides XPS multiplex scans for an ALD film deposited on a platinum substrate from the reaction with titanium tetrachloride and CHD at 180° C.
Figure 42:
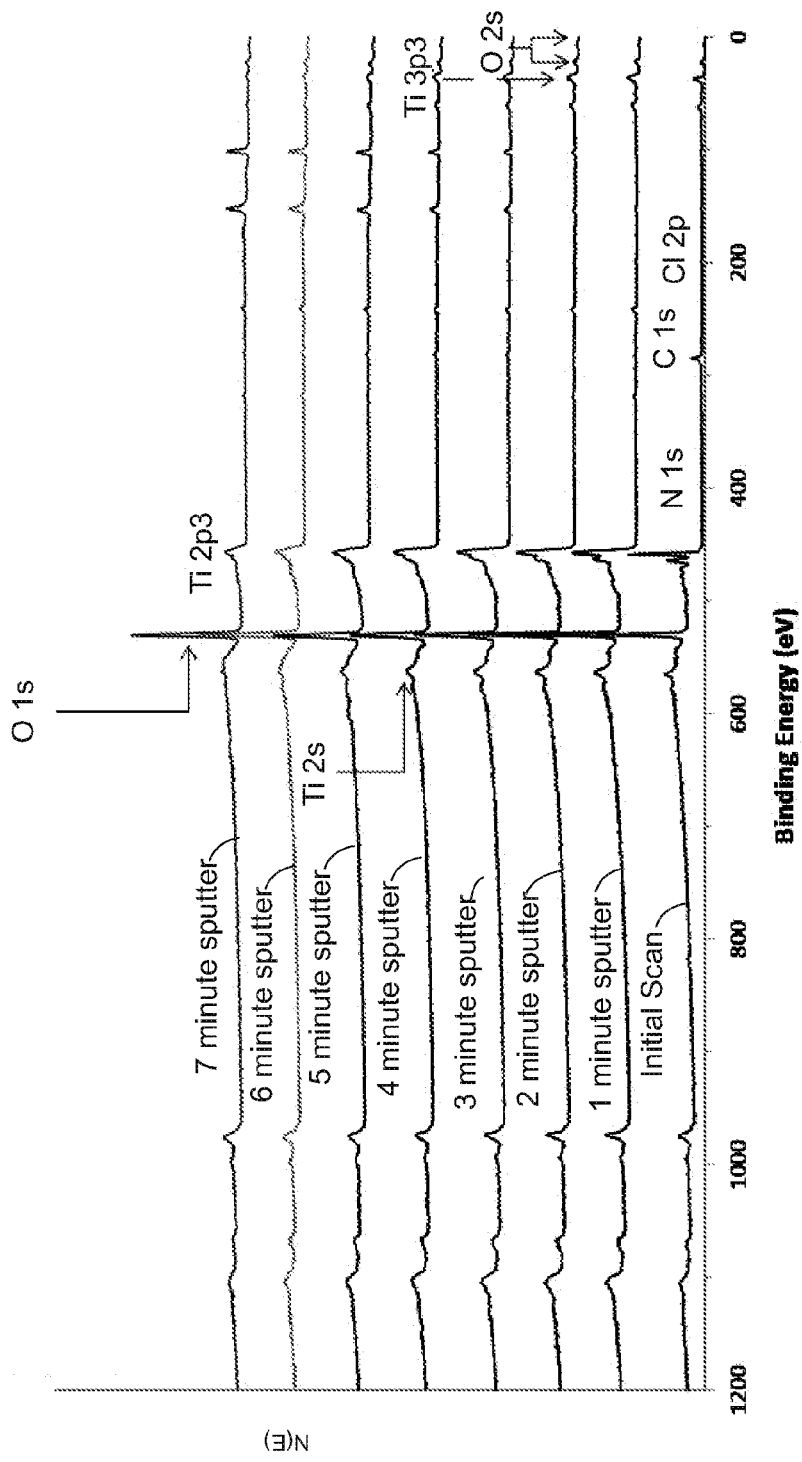
FIG. 42 provides XPS survey scans for ALD film deposited on a silicon substrate with a thermal silicon oxide layer from the reaction with titanium tetrachloride and CHD at 180° C.
Figure 43:
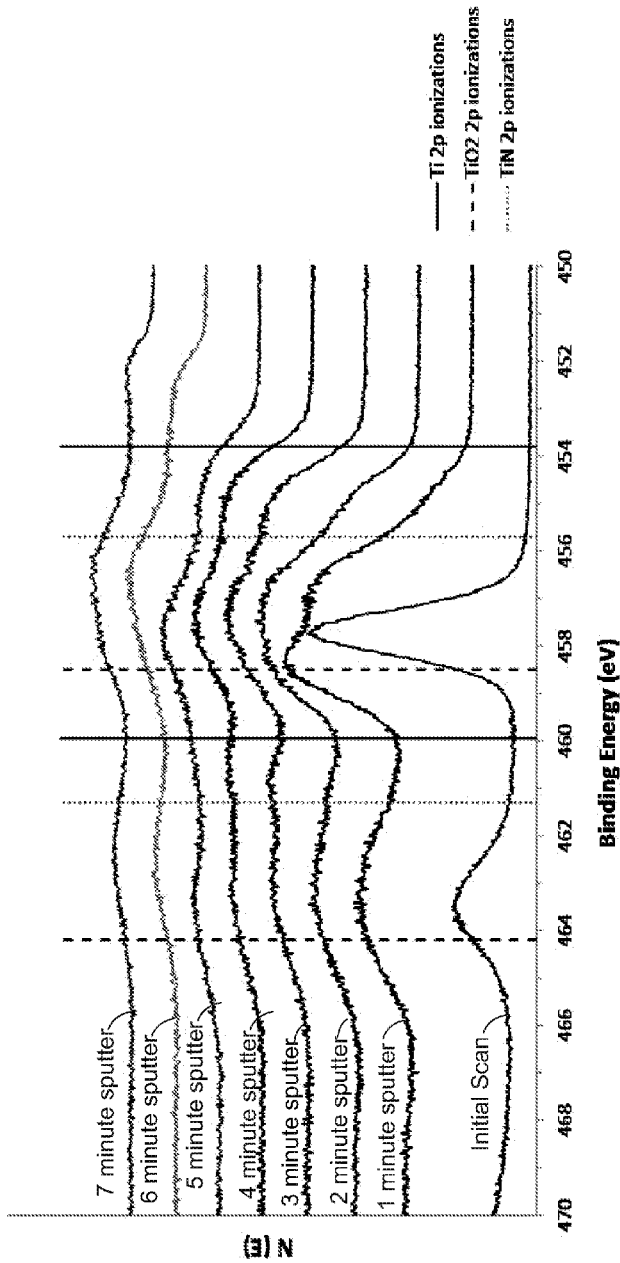
FIG. 43 provides XPS multiplex scans for an ALD film deposited on silicon substrate with a thermal silicon oxide layer from the reaction with titanium tetrachloride and CHD at 180° C.

FIGS. 40 and 41 respectively show XPS survey scans and XPS multiplex scans for an 8 nm ALD film deposited on a platinum substrate by reacting TiCl4 and CHD at 180° C. The scans confirm the presence of a titanium-containing film. FIGS. 42 and 43 respectively show XPS survey scans and XPS multiplex scans for an 8 nm ALD film deposited on a silicon oxide coated silicon substrate by reacting TiCl4 and CHD at 180 C. The scans confirm the presence of a titanium-containing film.
$TiCl_4$+DHP Titanium film growth was demonstrated using $TiCl_4$+DHP. Each cycle consisted of a 0.2 s pulse of $TiCl_4$, a 15.0 s purge, a 1.0 s pulse of DHP, and a 10.0 s purge. The $TiCl_4$ bubbler was maintained at 20° C. and the reaction chamber was held at 100° C. The temperature of the solid state booster for DHP delivery was set to 75° C. After 3,000 cycles, definitive film growth was achieved on Pd, Pt, TiN, Co, Cu, Ru, Si(100), and $SiO_2$. Average approximate growth rates were determined by SEM analysis: Pd (0.04 Å/cycle), Pt (0.11 Å/cycle), TiN (0.04 Å/cycle), Co (0.13 Å/cycle), Cu (0.11 Å/cycle), Ru (0.08 Å/cycle), Si (0.11 Å/cycle), and $SiO_2$ (0.12 Å/cycle).

Figure 44:
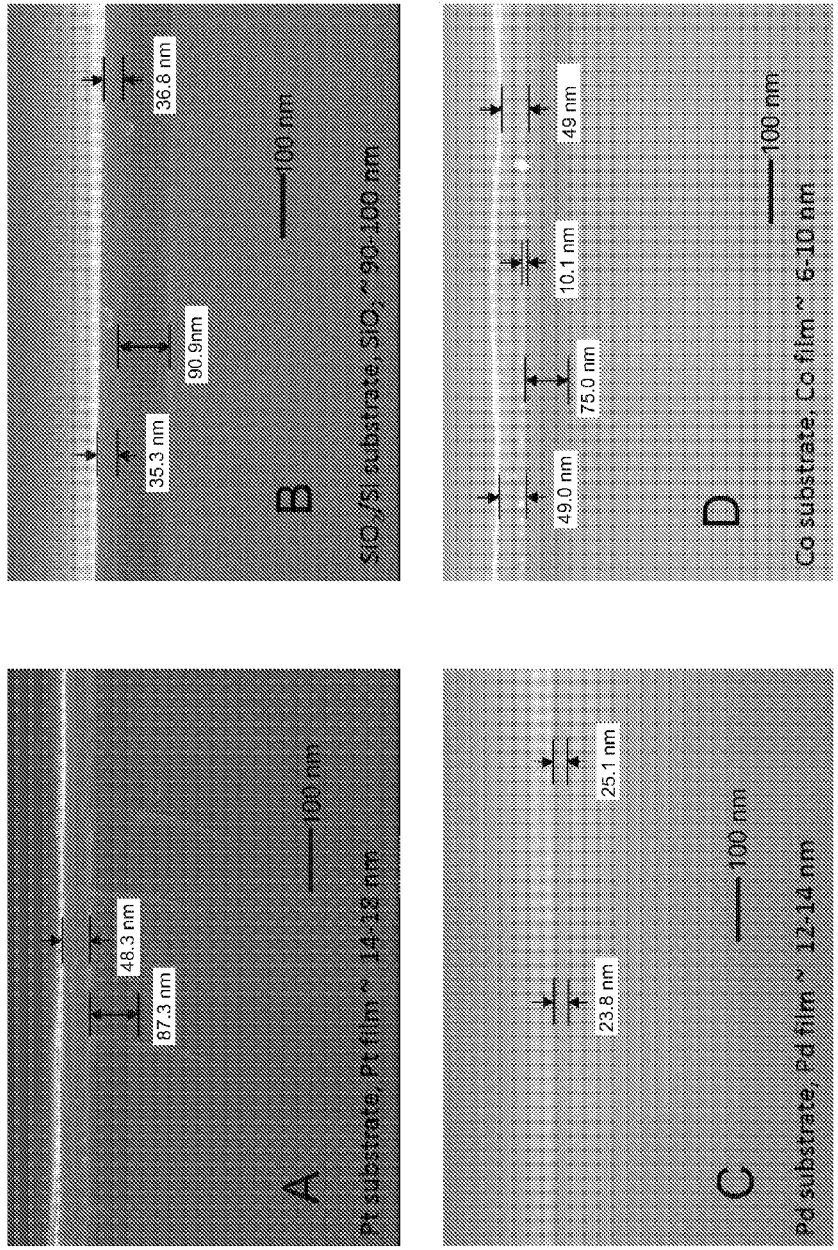
FIG. 44A provides an SEM cross-section for an ALD film deposited on a platinum substrate from the reaction with titanium tetrachloride and DHP.
FIG. 44B provides an SEM cross-section for an ALD film on a silicon substrate with a thermal silicon oxide layer from the reaction with titanium tetrachloride and DHP.
FIG. 44C provides an SEM cross-section for an ALD film on a palladium substrate from the reaction with titanium tetrachloride and DHP.
FIG. 44D provides an SEM cross-section for an ALD film on a cobalt substrate from the reaction with titanium tetrachloride and DHP.

FIG. 44A provides an SEM cross-section for an ALD film deposited on a platinum substrate from the reaction with titanium tetrachloride and DHP. From the micrograph, the combined platinum and titanium thickness is about 48 nm with an approximate platinum layer thickness of about 14 to 18 nm and a titanium layer thickness from 30 to 34 nm. FIG. 44B provides an SEM cross-section for an ALD film on a silicon substrate with a thermal silicon oxide layer from the reaction with titanium tetrachloride and DHP. From the micrograph, the titanium layer thickness is about 35 nm. FIG. 44C provides an SEM cross-section for an ALD film on a palladium substrate from the reaction with titanium tetrachloride and DHP. From the micrograph, the combined palladium and titanium thickness is about 24 nm with an approximate palladium layer thickness of about 12 to 14 nm and a titanium layer thickness of about 10 to 12 nm. FIG. 44D provides an SEM cross-section for an ALD film on a cobalt substrate from the reaction with titanium tetrachloride and DHP. From the micrograph, the combined cobalt and titanium thickness is about 48 nm with an approximate titanium layer thickness of about 6 to 10 nm and a titanium layer thickness of about 38 to 42 nm.

Figure 45:
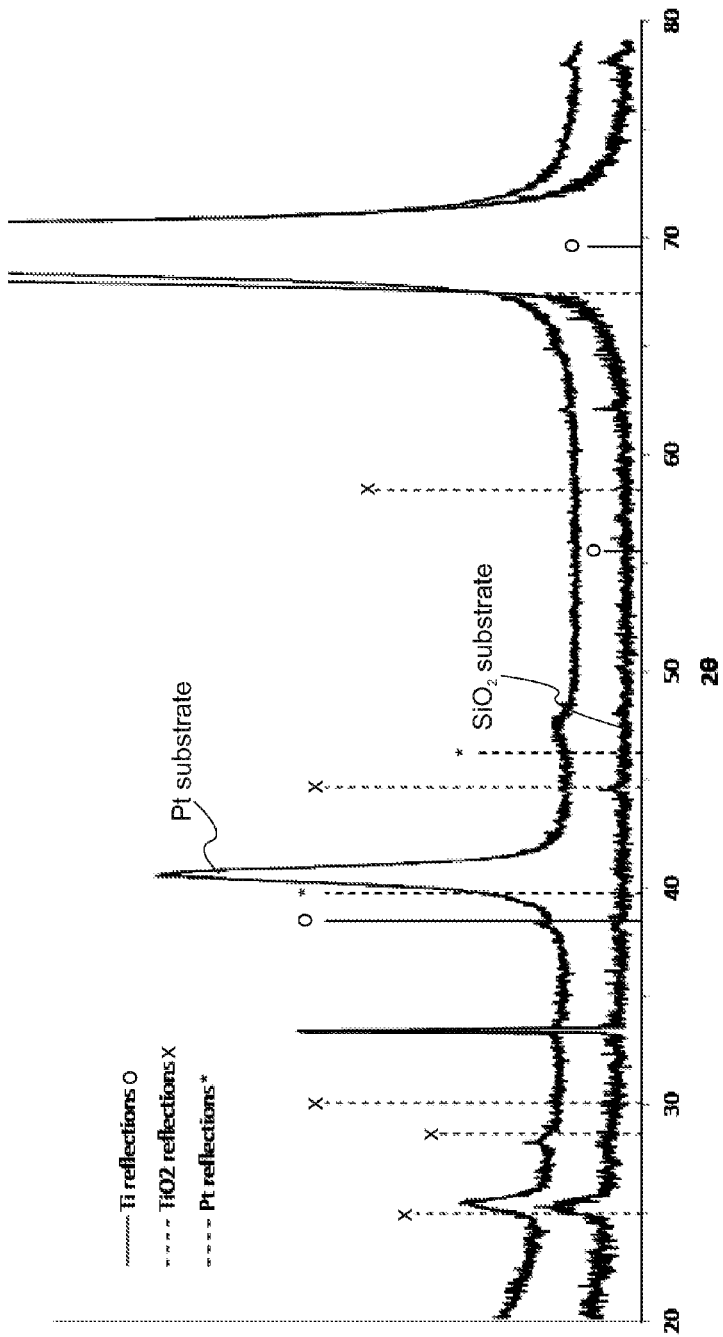
FIG. 45 provides X-ray diffraction (XRD) spectra for ALD films formed from the reaction with titanium tetrachloride and DHP on a platinum substrate and a silicon oxide substrate.
Figure 46:
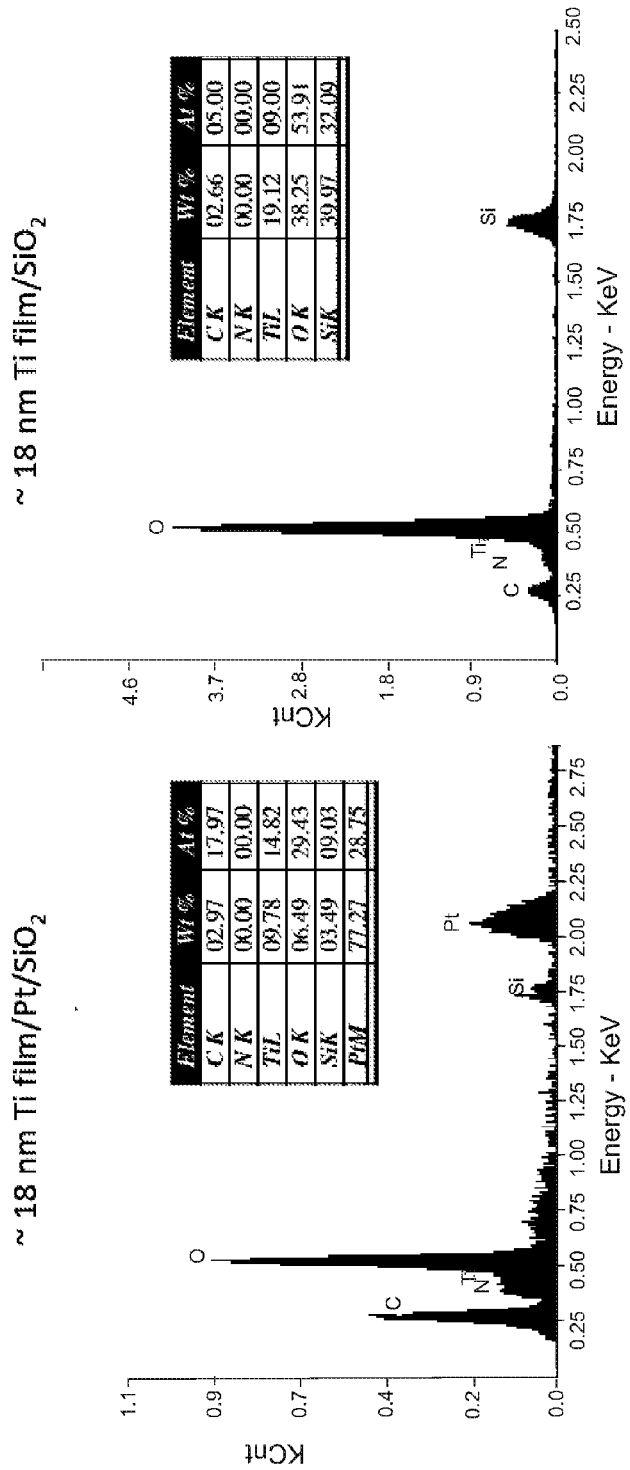
FIG. 46 provides Energy-dispersive X-ray (EDS) spectra for ALD films formed from the reaction with titanium tetrachloride and DHP on a platinum substrate and a silicon oxide substrates.
Figure 47:
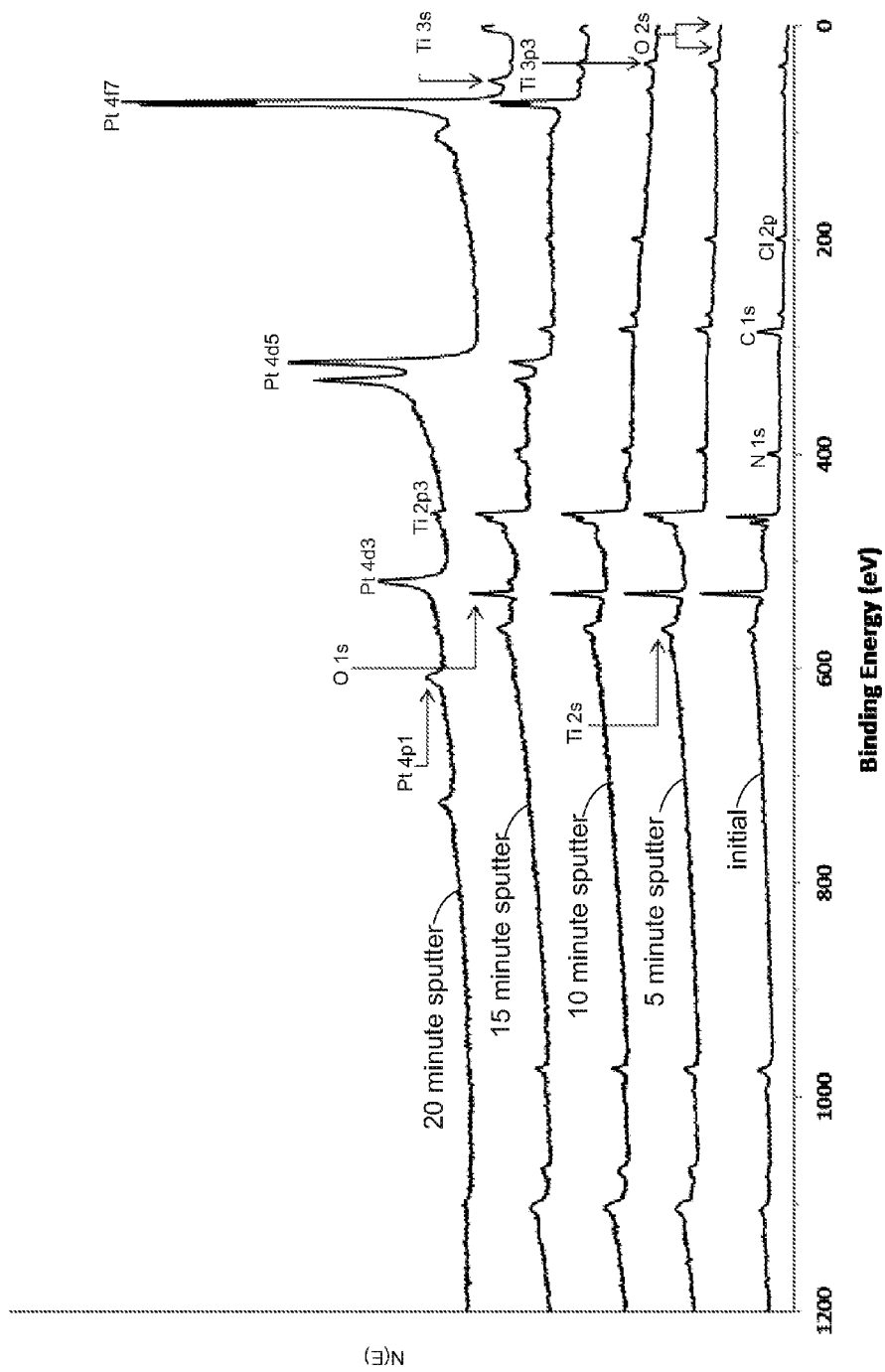
FIG. 47 provides XPS survey scans for an ALD film deposited on a platinum substrate from the reaction with titanium tetrachloride and DHP at 100° C.
Figure 48:
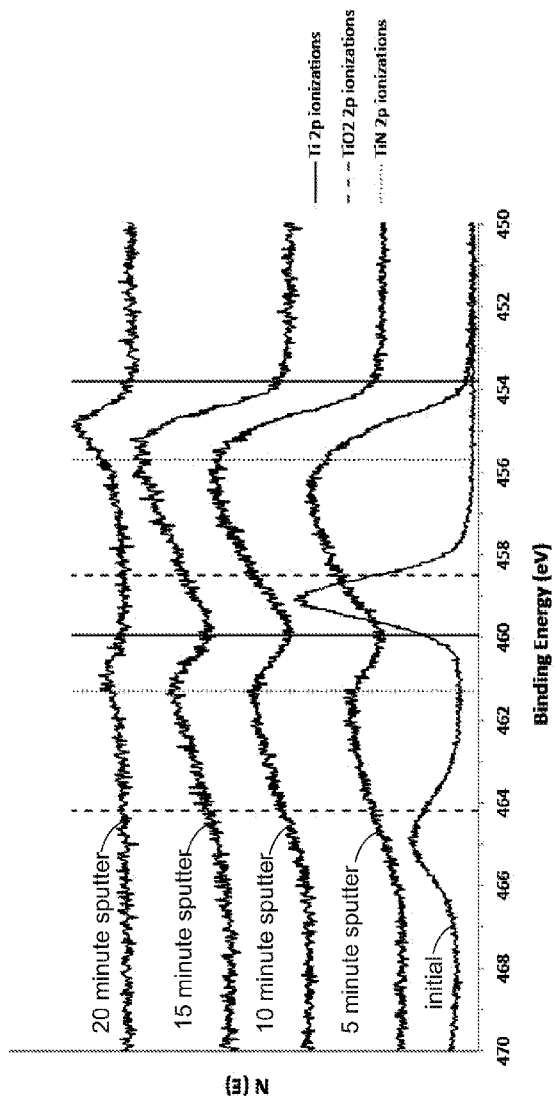
FIG. 48 provides XPS multiplex scans for an ALD film deposited on a platinum substrate from the reaction with titanium tetrachloride and DHP at 100° C.
Figure 49:
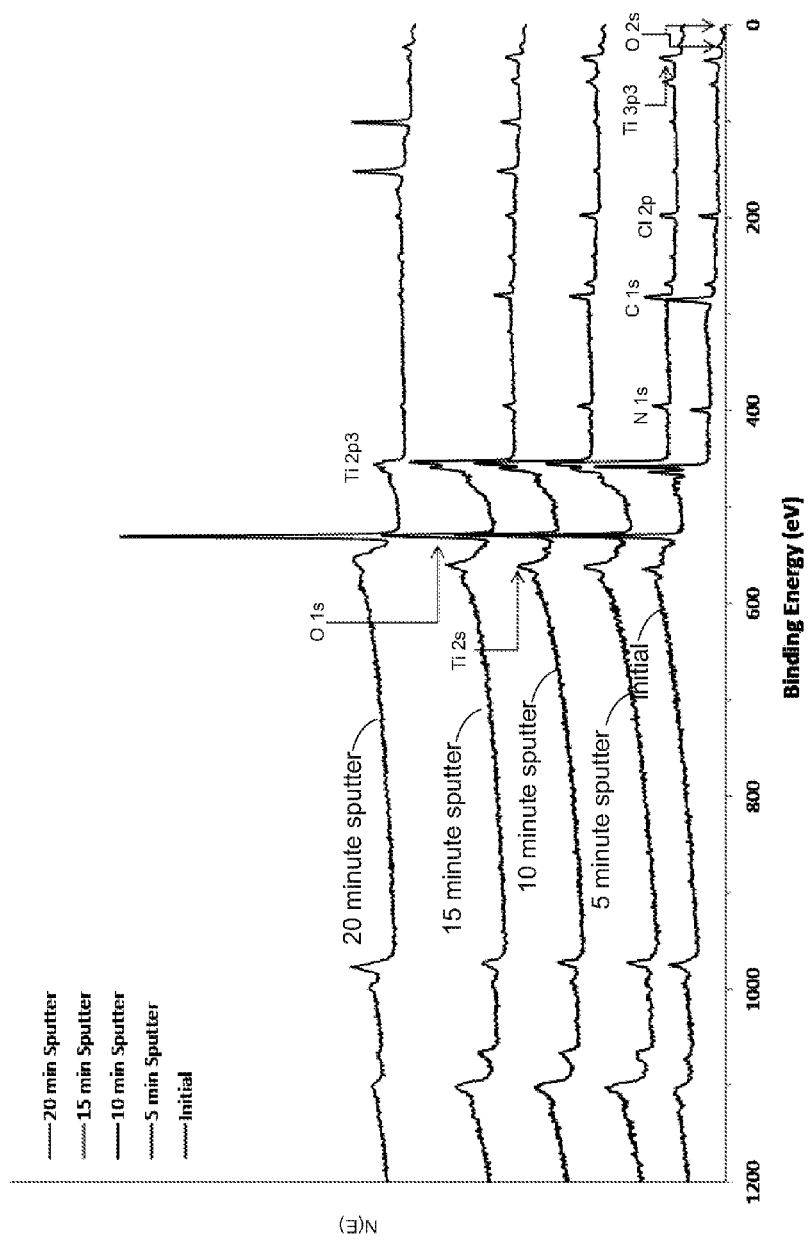
FIG. 49 provides XPS survey scans for an ALD film deposited a silicon substrate with a thermal silicon oxide layer from the reaction with titanium tetrachloride and DHP at 100° C.
Figure 50:
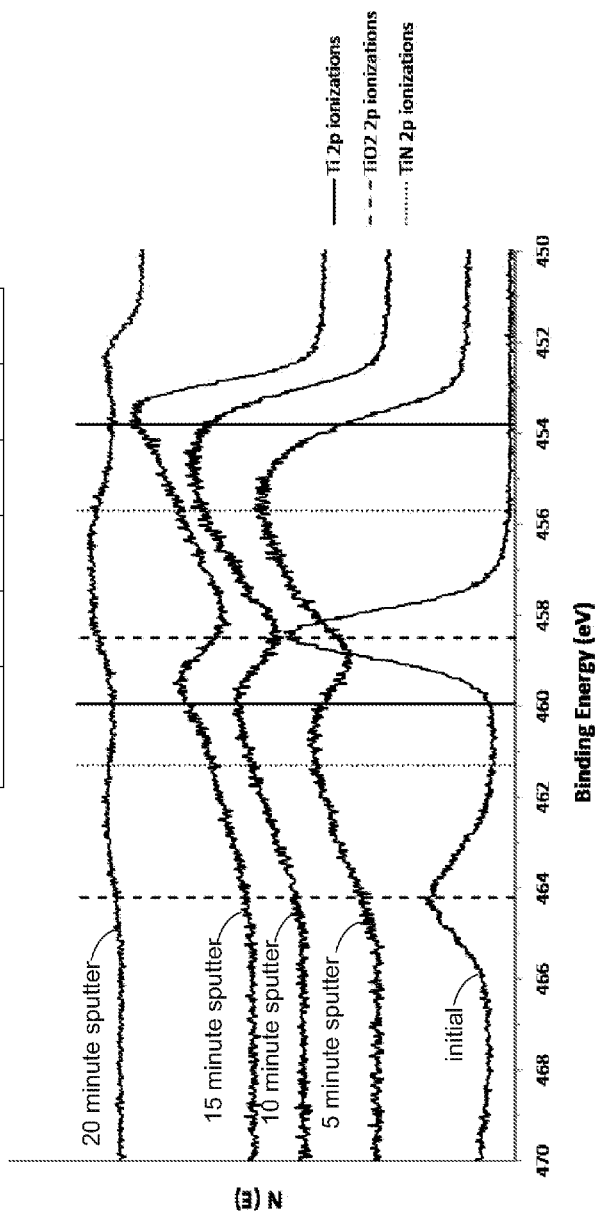
FIG. 50 provides XPS multiplex scans for an ALD film deposited on a silicon substrate with a thermal silicon oxide layer from the reaction with titanium tetrachloride and DHP at 100° C.

FIG. 45 provides X-ray diffraction (XRD) spectra for ALD films formed from the reaction with $TiCl_4$ and DHP on platinum substrates and silicon oxide substrates. It should be noted that the major Ti reflection appears on the Pt substrate as a minor component ($2\theta$=38.48°) and the major $TiO_2$ reflection appears on the $SiO_2$ substrate as a minor component ($2\theta$=44.67°). The thicknesses of the titanium films are about 30 to 35 nm. FIG. 46 provides EDS spectra for ALD films formed from the reaction with TiCl$_4$ and DHP on platinum substrates and silicon oxide substrates. The oxide film gradually changes in oxidation state from TiO$_2$→Ti$_2$O$_3$→TiO→ (by XPS analysis). It is hypothesized that oxide growth is controlled by oxygen diffusion through the existing oxide film (Brunette, D. M.; Tengvall, P.; Textor, M.; Thomsen, P. *Titanium in Medicine*; Springer, 2001; pp. 178-182). Finally, the thickness of the interfacial gradient layer is 39±2 nm for polished commercially prepared titanium by RBS analysis (Brunette, D. M.; Tengvall, P.; Textor, M.; Thomsen, P. *Titanium in Medicine*; Springer, 2001; pp. 178-182). FIGS. 47 and 48, respectively, show XPS survey scans and XPS multiplex scans for a 34 nm ALD film deposited on a platinum substrate by reacting TiCl4 and DHP at 100 C. The scans confirm the presence of a titanium-containing film. FIGS. 49 and 50, respectively, show XPS survey scans and XPS multiplex scans for a 35 nm ALD film deposited on a silicon oxide coated silicon substrate by reacting TiCl4 and DHP at 100 C. The scans confirm the presence of a titanium-containing film.

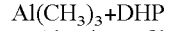

Aluminum film growth was demonstrated using Al(CH$_3$)$_3$ and DHP. Each cycle consisted of a 0.1 s pulse of Al(CH$_3$)$_3$, a 8.0 s purge, a 1.0 s pulse of DHP, and a 10.0 s purge. The temperature of the Al(CH$_3$)$_3$ and DHP bubblers were 20° C. and 70° C., respectively. The reaction chamber was maintained at 180° C. After 1,000 cycles, films were observed on the Co and SiO$_2$ substrates. The film on SiO$_2$ was very thin, but observable by SEM. The growth rate on the Co substrate was approximately 0.15 Å/cycle.

Figure 51:
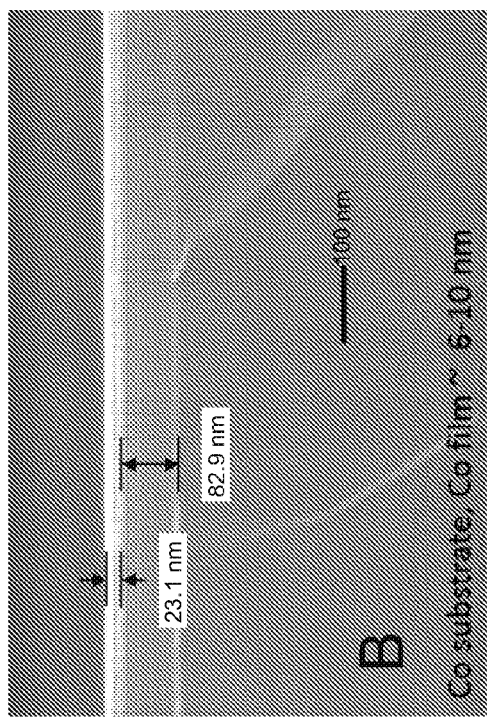
FIG. 51A provides a SEM cross-section of an aluminum film deposited on a silicon substrate with a thermal silicon oxide layer from trimethylaluminum and DHP at 180° C.
FIG. 51B provides a SEM cross-section of an aluminum film deposited on a cobalt-coated silicon substrate from trimethylaluminum and DHP at 180° C.
Figure 51:
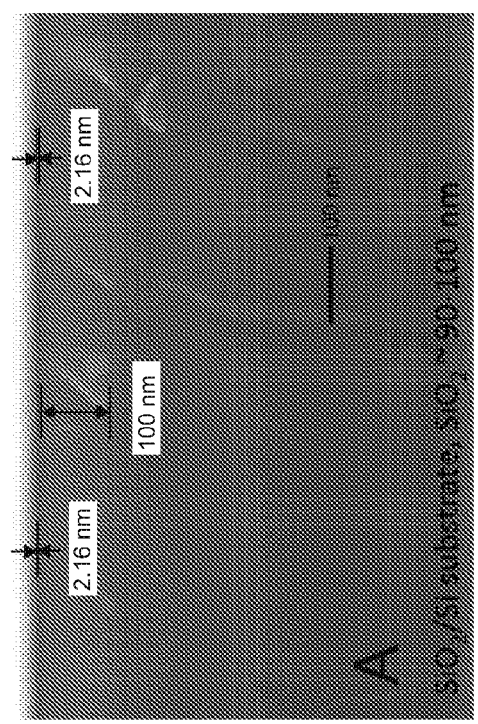

FIG. 51A provides a SEM cross-section for an aluminum-containing film deposited on a silicon oxide coated silicon substrate from trimethylaluminum and DHP at 180° C. From the micrograph, the aluminum layer thickness of about 2 nm. FIG. 51B provides a SEM cross-section for an aluminum-containing film deposited on a cobalt-coated silicon substrate from trimethylaluminum and DHP at 180° C. From the micrograph, the combined cobalt and aluminum thickness is about 23 nm with the cobalt layer having a thickness from about 6 to 10 nm and the aluminum layer having a thickness from about 13 to 17 nm.

Figure 52:
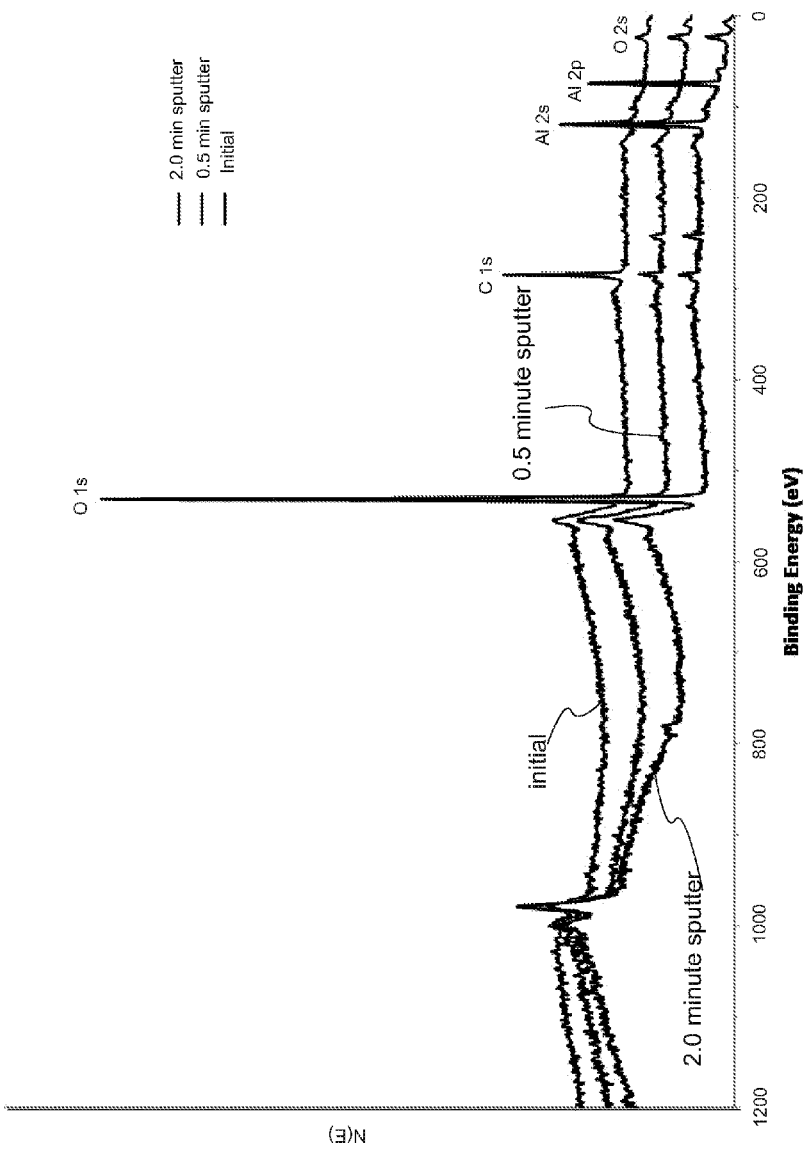
FIG. 52 provides XPS survey scans for an ALD film deposited on a cobalt-coated silicon substrate from trimethylaluminum and DHP at 180° C.
Figure 53:
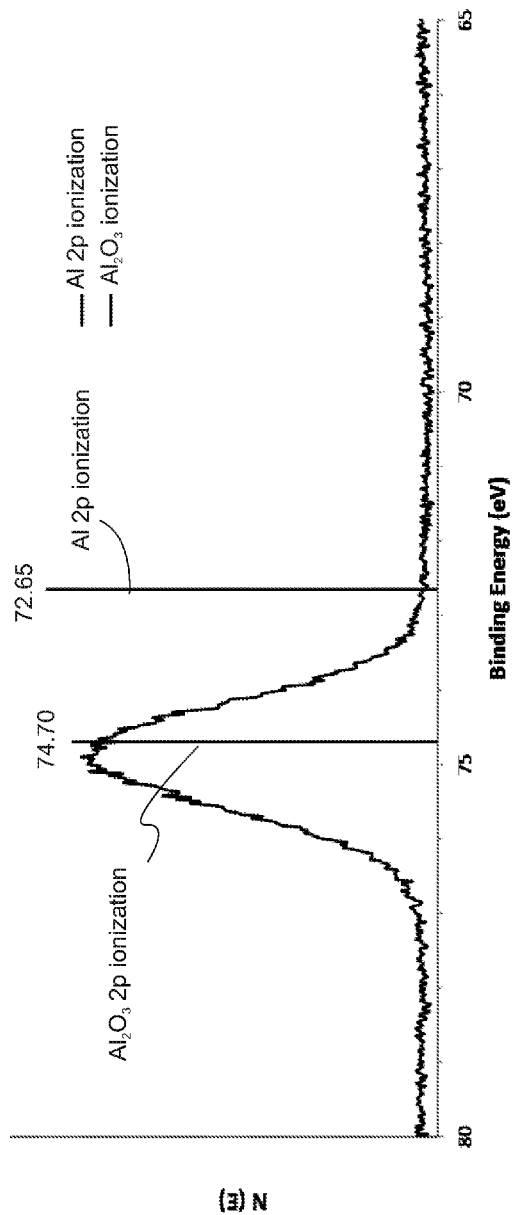
FIG. 53 provides XPS multiplex scans for an ALD film deposited on a cobalt-coated silicon substrate from trimethylaluminum and DHP at 180° C.

FIGS. 52 and 53 respectively show XPS survey scans and XPS multiplex scans for a 15 nm film deposited on a cobalt-coated substrate by reacting trimethylaluminum and DHP at 180 C. The scans confirm the presence of an aluminum-containing film.

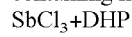

Antimony film growth was demonstrated using SbCl$_3$ and DHP. Each cycle consisted of a 5.0 s pulse of SbCl$_3$, a 15.0 s purge, a 1.0 s pulse of DHP, and a 10.0 s purge. The temperature of the solid state booster for SbCl$_3$ delivery was set to 40° C. The DHP bubbler was set to 70° C. and the reaction chamber was held at 180° C. After 1,000 cycles, films were deposited on Cu, Pt, and Pd substrates. A growth rate of 0.20 Å/cycle was achieved on the Pt substrate. Growth on the Cu and Pd substrates was non-uniform and granular. Analysis by top-down SEM revealed dense crystalline morphologies on the Pt and Pd substrates.

Figure 54:
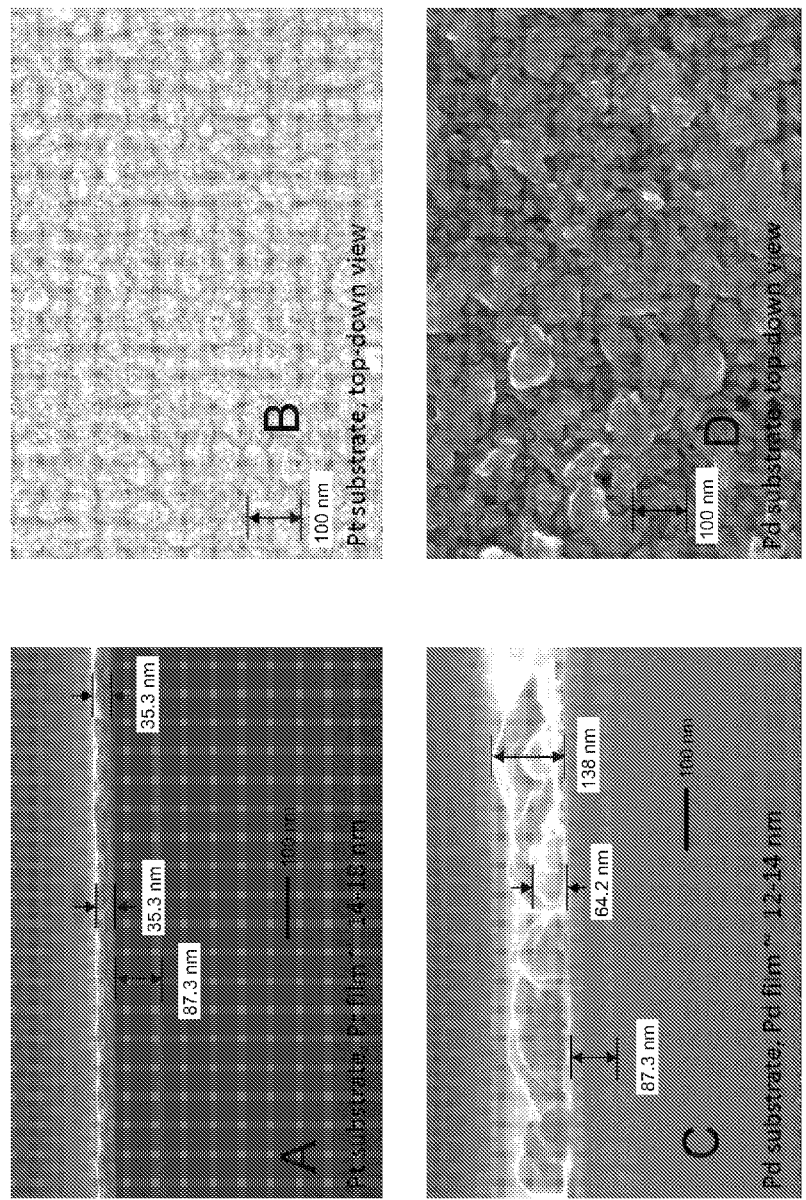
FIG. 54A provides an SEM cross-section for an ALD film deposited on a platinum substrate from antimony trichloride and DHP at 180° C.
FIG. 54B provides an SEM top-down view for an ALD film deposited on a platinum substrate from antimony trichloride and DHP at 180° C.
FIG. 54C provides an SEM cross-section for an ALD film deposited on a palladium substrate from antimony trichloride and DHP at 180° C.
FIG. 54D provides an SEM top-down view for an ALD film deposited on a palladium substrate from antimony trichloride and DHP at 180° C.

FIG. 54A provides an SEM cross-section for an ALD film deposited on a platinum substrate from SbCl$_3$ and DHP at 180° C. From the micrograph, the combined platinum and antimony thickness is about 35 nm with the cobalt layer having a thickness from about 14 to 18 nm and the antimony layer having a thickness from about 17 to 21 nm. FIG. 54B provides an SEM top-down view for an ALD film deposited on a platinum substrate from antimony trichloride and DHP at 180° C. FIG. 54C provides an SEM cross-section for an ALD film deposited on a palladium substrate from SbCl$_3$ and DHP at 180° C. From the micrograph, the combined platinum and antimony thickness is about 64 to 136 nm with the cobalt layer having a thickness from about 12 to 14 nm and the antimony layer having a thickness from about 50 to 124 nm. This film is granular and highly non-uniform.

Figure 55:
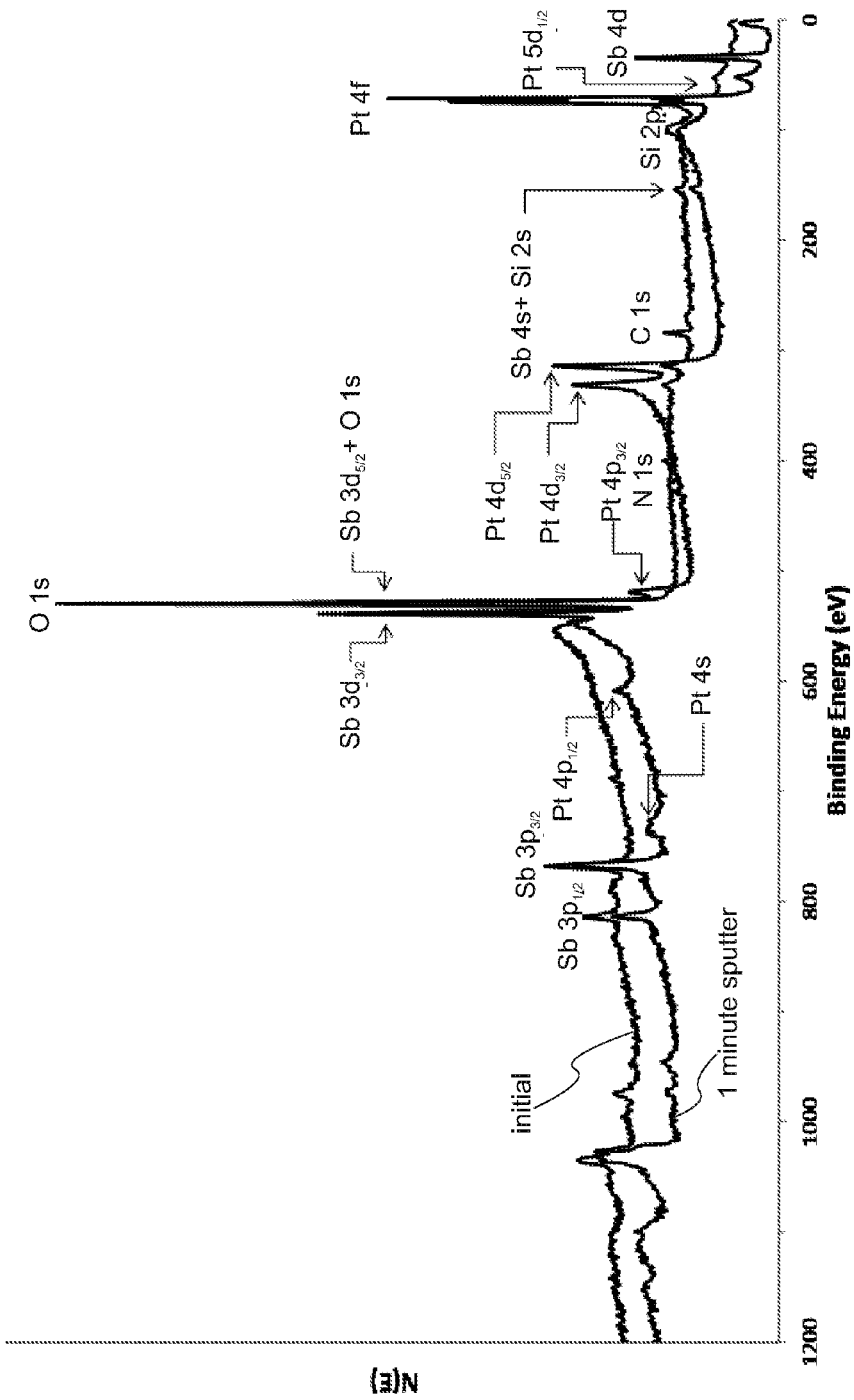
FIG. 55 provides XPS survey scans for an ALD film deposited on a palladium substrate from antimony trichloride and DHP at 180° C.
Figure 56:
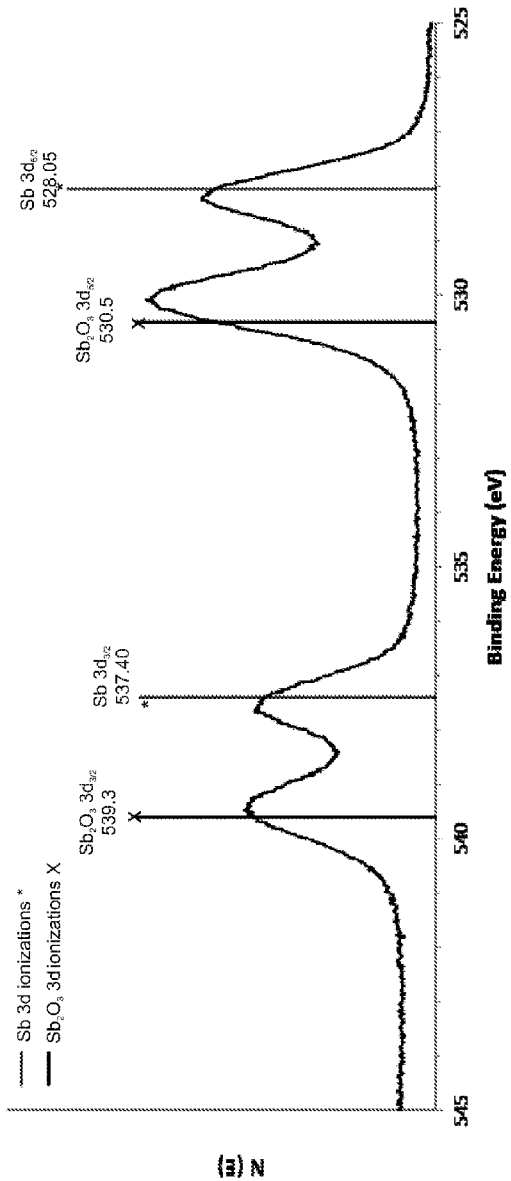
FIG. 56 provides XPS multiplex scans for an ALD film deposited on a palladium substrate from antimony trichloride and DHP at 180° C.

FIG. 54D provides an SEM top-down view for an ALD film deposited on a palladium substrate from SbCl$_3$ and DHP at 180° C. FIGS. 55 and 56, respectively, show XPS survey scans and XPS multiplex scans for a 20 nm film deposited on a platinum substrate by reacting SbCl$_3$ and DHP at 180 C. The scans confirm the presence of an antimony-containing film.

Synthesis of Metal Complexes:

The synthesis of the 1,4-di-tert-butyl-1,4-diazabutadiene ligand (dad$^{tBu2}$) was performed in accordance with a literature procedure (Kliegman, J. M.; Barnes, R. K. Tetrahedron 1970, 26, 2555-2560):

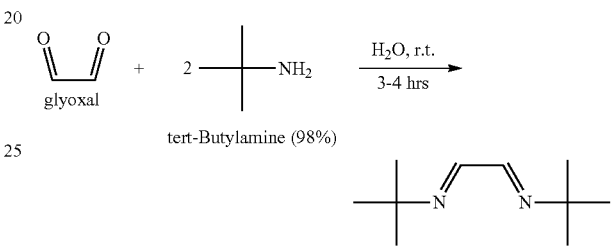

A previously reported procedure was used for the subsequent syntheses of Cr—, Mn—, Fe—, Co—, and Ni(dad$^{tBu2}$)$_2$ compounds (Knisley, T. J.; Ariyasena, T. C.; Sajavaara, T.; Saly, M. J.; Winter, C. H. Chem. Mater. 2011, 23, 4417-4419). The syntheses of Mg- and Zn(dad$^{tBu2}$)$_2$ followed an identical process. This general method was modified for the syntheses of Al- and Ti(dad$^{tBu2}$)$_2$ compounds, whereby the reagents were cooled to −78° C. prior to cannulation of the ligand to the metal salt.

Crystal structures have been published for several M(dad$^{tBu2}$)$_2$ complexes (M=Mg, Al, Cr, Fe, Co, Ni, Zn) (Cardiner, M. G.; Hanson, G. R.; Henderson, M. J.; Lee, F. C. Raston, C. L. Inorg. Chem. 1994, 33, 2456-2461; Geoffrey, F.; Cloke, N.; Dalby, C. I.; Henderson, M. J.; Hitchcock, P. B.; Kennard, C. H. L.; Lamb, R. N.; Raston, C. L. J. Chem. Soc., Chem. Commun. 1990, 1394-1396; Knisley, T. J.; Ariyasena, T. C.; Sajavaara, T.; Saly, M. J.; Winter, C. H. Chem. Mater. 2011, 23, 4417-4419). Ti(dad$^{tBu2}$)$_2$ and Mn(dad$^{tBu2}$)$_2$ have been reported in the literature, however, their structures have not been published (Tom Dieck, H.; Rieger, H. J.; Fendesak, G. Inorganica Chimica Acta 1990, 177, 191-197; Knisley, T. J.; Ariyasena, T. C.; Sajavaara, T.; Saly, M. J.; Winter, C. H. Chem. Mater. 2011, 23, 4417-4419). Following the synthesis outlined in Scheme 3, a low-resolution structure of Ti(dad$^{tBu2}$)$_2$ was obtained with crystals grown by sublimation of the crude product at 120° C./0.05 Torr.

Scheme 1: Synthetic procedure for M(dad$^{tBu2}$)$_2$ compounds, where M = Mg, Cr, Mn, Fe, Ni, Co, Zn

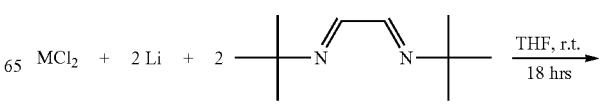

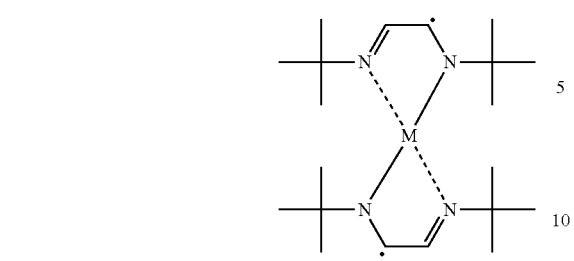

Scheme 2: Synthetic procedure for Al(dad$^{tBu2}$)$_2$

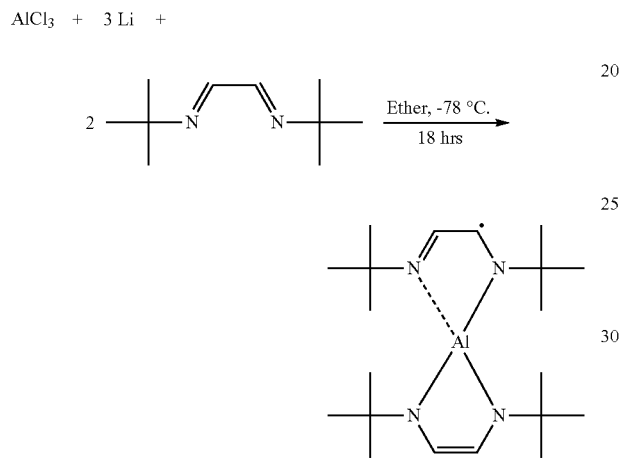

Scheme 3: Synthetic procedure for Ti(dad$^{tBu2}$)$_2$

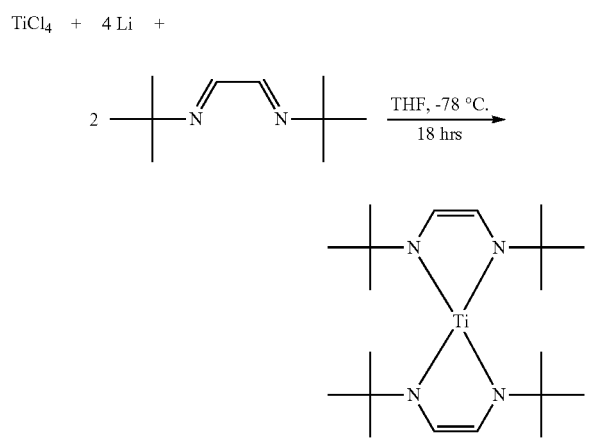

The procedure outlined in Scheme 2 afforded a mixture of Al(dad$^{tBu2}$)Cl$_2$ and Al(dad$^{tBu2}$)$_2$. These products were separable due to their difference in volatility. The novel Al(dad$^{tBu2}$)Cl$_2$ compound sublimed at 105° C./0.05 Torr, while the unexpected Al(dad$^{tBu2}$)$_2$ product sublimed at 130° C./0.05 Torr. Preparative sublimation studies on Al(dad$^{tBu2}$)Cl$_2$ resulted in 88.9% recovered material, with 5.5% non-volatile residue. The melting point was determined as 157-158° C.

Scheme 4: Synthetic procedure for Al(dad$^{tBu2}$)Cl$_2$

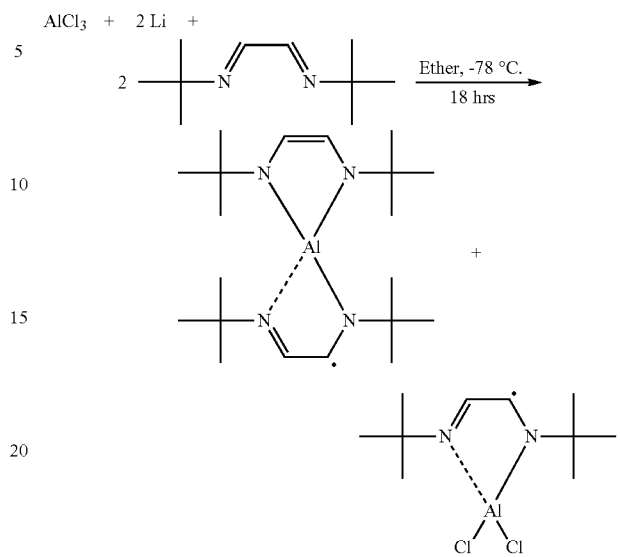

The general class of M($^{R2}$DAD)Cl$_2$ (R=iPr, tBu, phenyl, methylphenyl, etc.) compounds may be especially useful for the deposition process described herein. Previously reported compounds of this family include 1,4-di(4-methylphenyl)1,4-diazabutadiene]ZnCl$_2$,$^L$ and Ti(dad$^{tBu2}$)Cl$_2$(Tom Dieck, H.; Rieger, H. J.; Fendesak, G. Inorganica Chimica Acta 1990, 177, 191-197) however, the latter exists as a dimer in the solid state, where the titanium atoms are bridged by two chloro ligands. To date, no compounds of this general class have been used as precursors for film growth.

ALD Deposition Experiments

Co(dad$^{tBu2}$)$_2$+HCOOH

Metallic cobalt films were grown by ALD using a binary process of Co(dad$^{tBu2}$)$_2$+HCOOH. Each cycle consisted of a 6.0 s pulse of Co(dad$^{tBu2}$)$_2$, a 5.0 s purge, a 0.2 s pulse of HCOOH, and a 5.0 s purge. The Co(dad$^{tBu2}$)$_2$ was delivered by a solid state booster, maintained at a temperature of 140° C., affording a source temperature of 137±1° C. The HCOOH was delivered by a bubbler maintained at 23° C. Purified nitrogen was used as the carrier gas, with flow rates of 80 sccm for both precursors. The temperature of the reaction chamber spanned a range of 140-240° C. during the deposition experiments. All films were grown for 1000 cycles and allowed to cool to ambient temperature before exposure to air. Growth was achieved on a variety of metallic and insulating substrates, including Si(100), SiO$_2$, Cu, Pt, Pd, and Ru.

Figure 57:
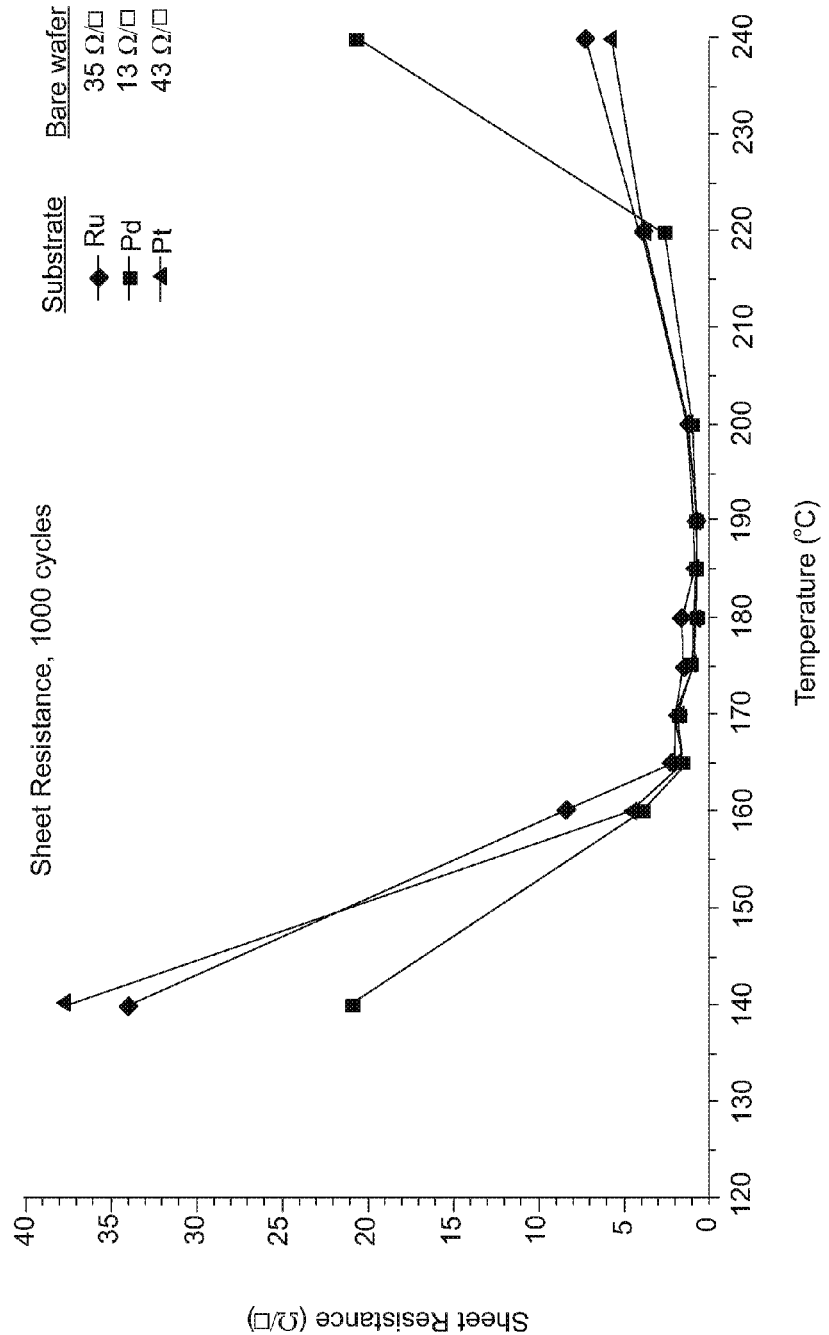
FIG. 57 provides sheet resistances for cobalt films grown on Ru, Pt, and Pd substrates.

Cobalt films deposited within the 165-200° C. window had extremely low sheet resistivities of 1-2Ω/□ when grown on Ru, Pt, and Pd substrates (FIG. 57). The bulk resistivities of the cobalt films grown on Ru within the 165-225° C. temperature range are 13-19 μΩ cm; these values approach that of bulk cobalt metal (6.24 μΩ cm at 20° C.).

Figure 58:
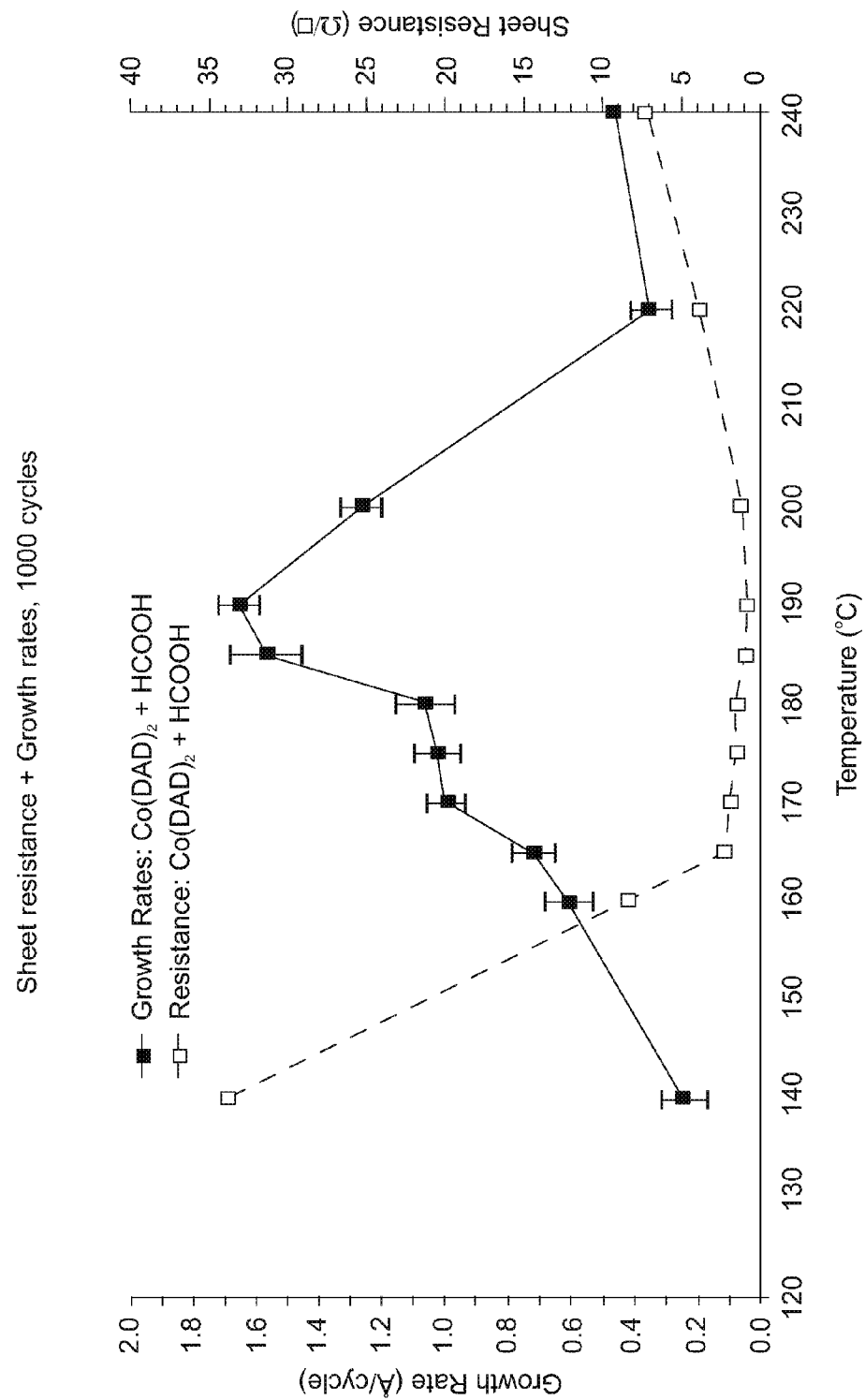
FIG. 58 provides growth rates and sheet resistances versus temperature for cobalt films on a Ru substrate.
Figure 59:
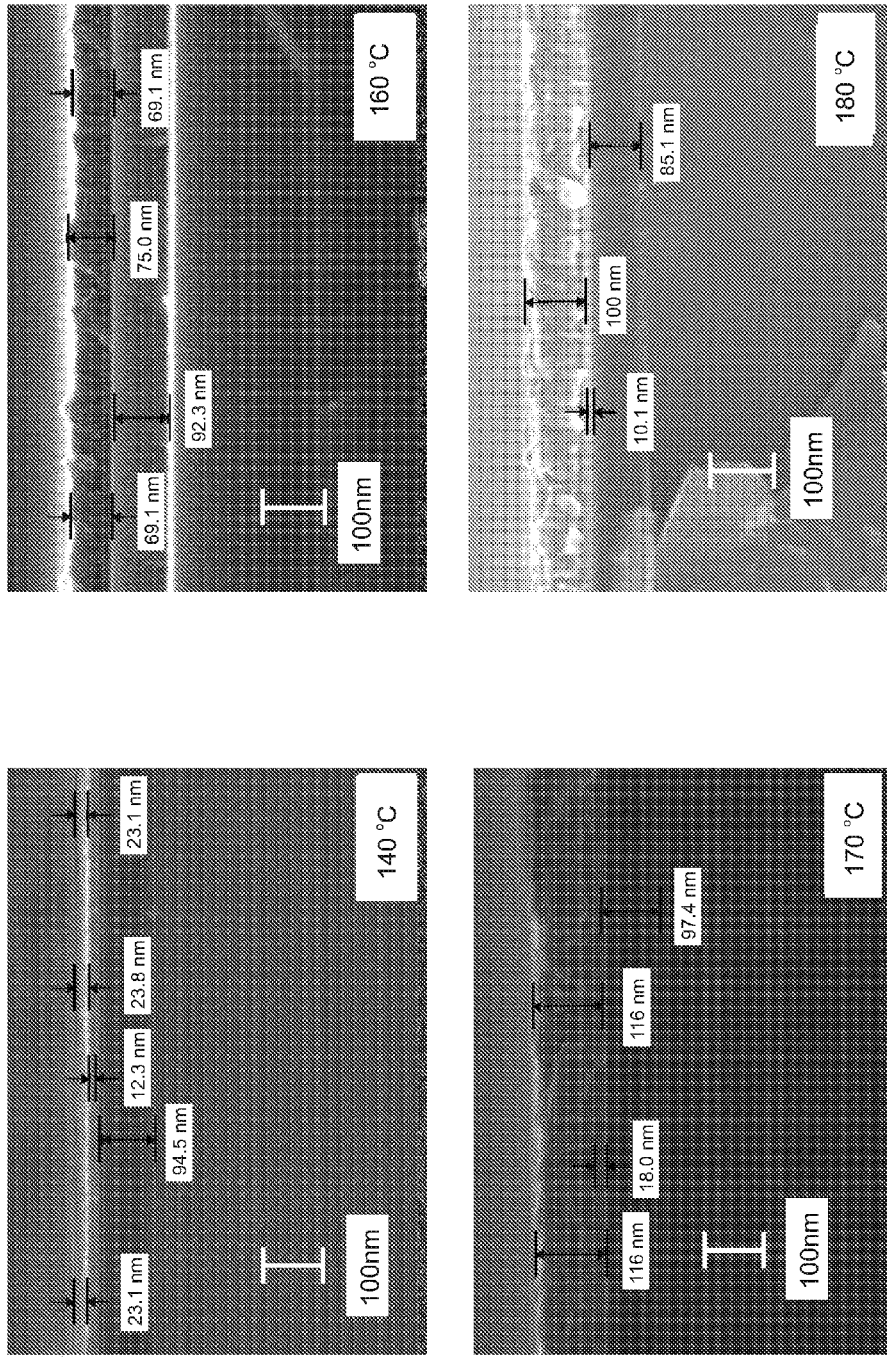
FIG. 59 provides SEM cross-sectional micrographs of cobalt films on Ru substrates.
Figure 60:
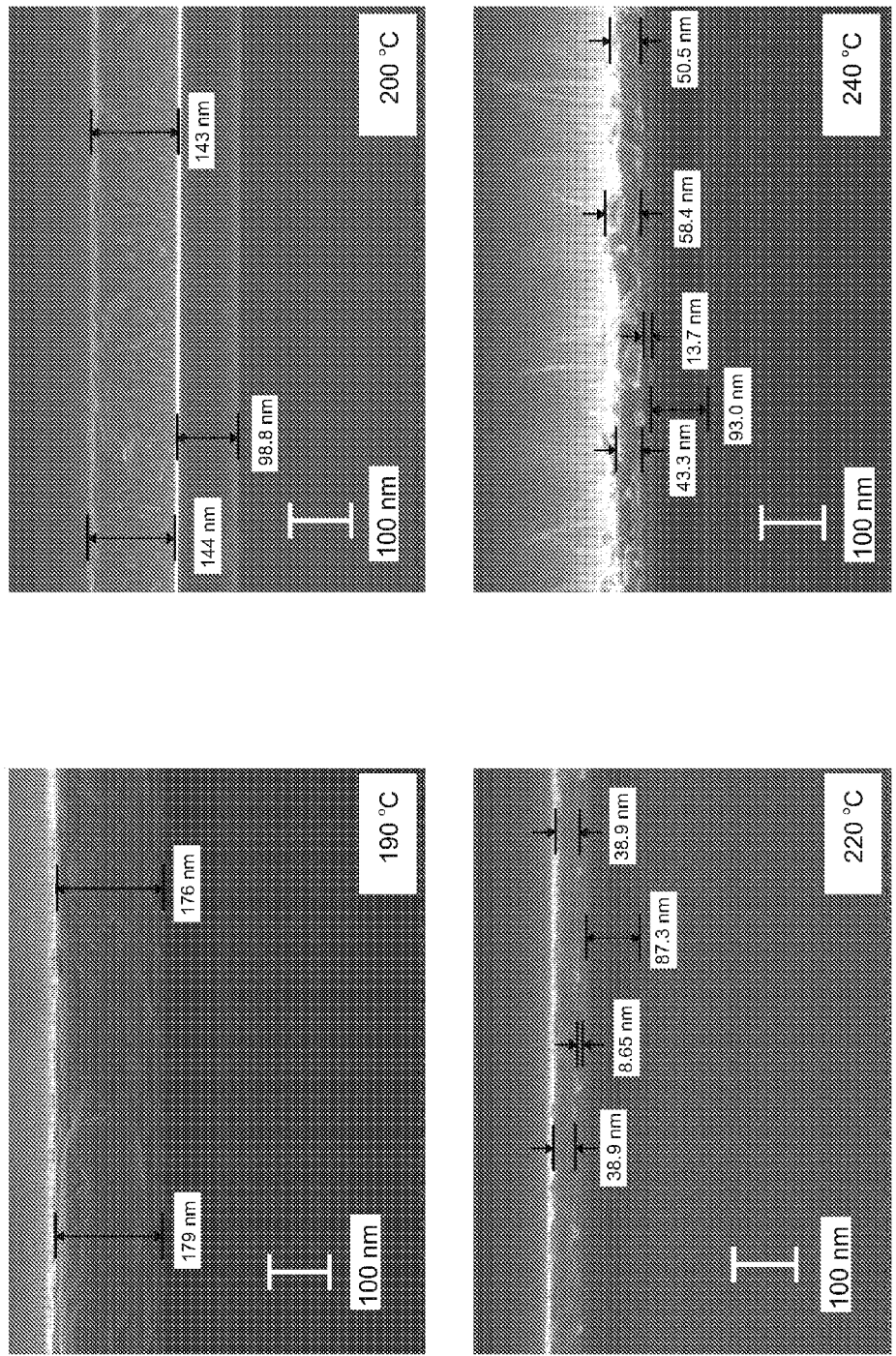
FIG. 60 provides SEM cross-sectional micrographs of cobalt films on Ru substrates.
Figure 61:
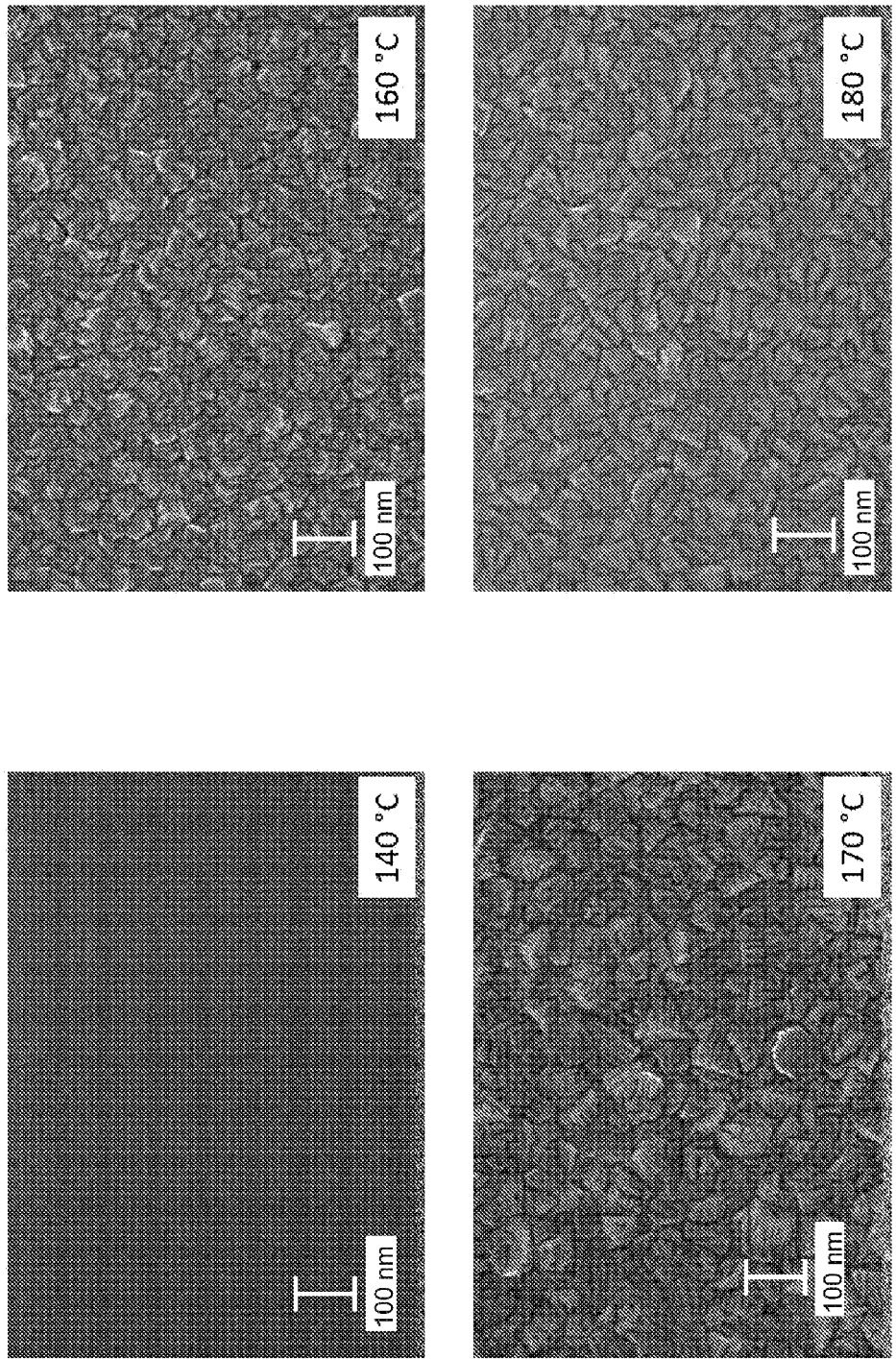
FIG. 61 provides SEM top-down view micrographs of cobalt films on Ru substrates.
Figure 62:
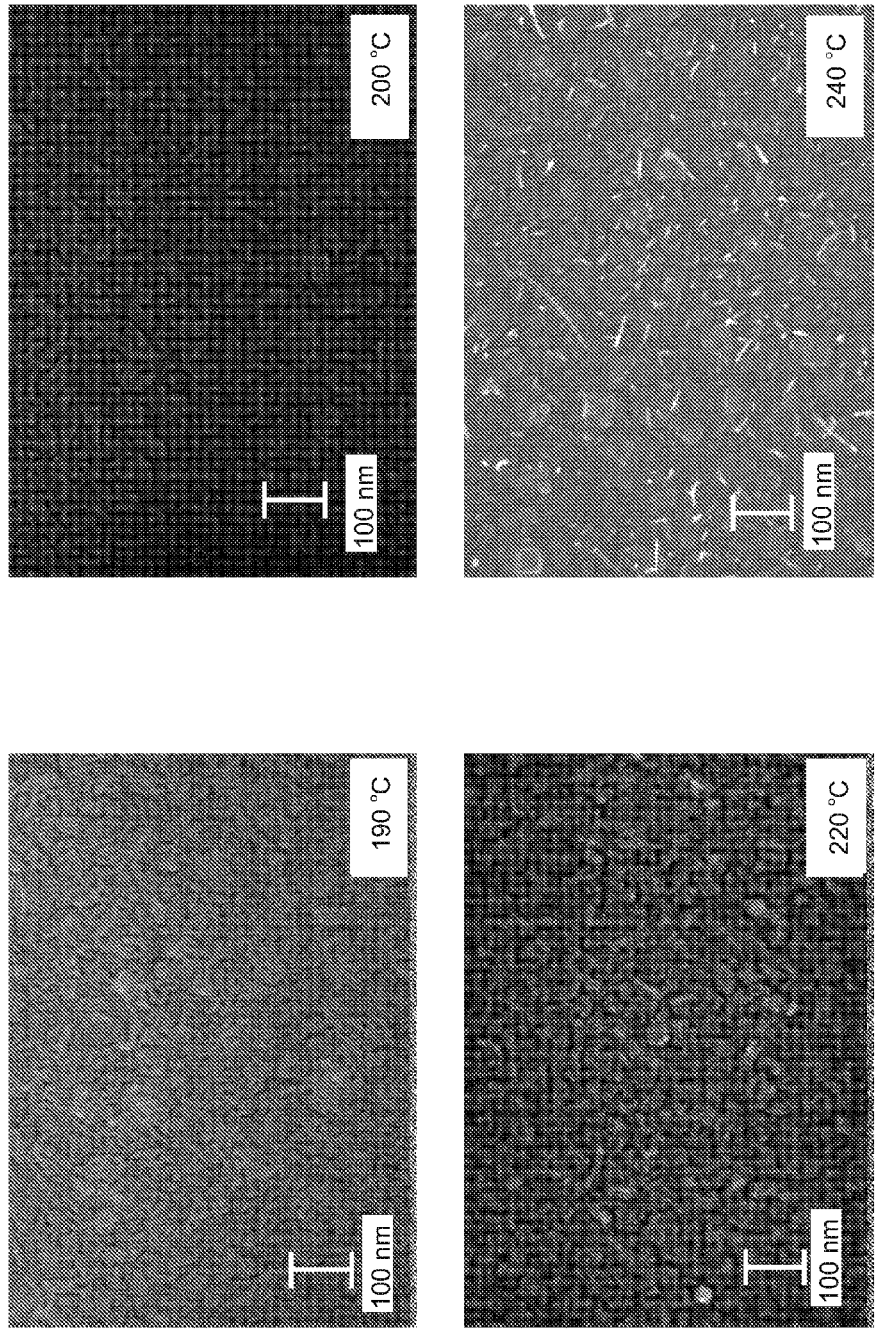
FIG. 62 provides SEM top-down view micrographs of cobalt films on Ru substrates.

Films deposited on Ru substrates at 165° C., 180° C., and 200° C. had respective growth rates of 1.15 Å/cycle, 1.06 Å/cycle, 1.27 Å/cycle. A region of constant growth was observed from 170-180° C. (FIG. 58). Cross-sectional SEM micrographs show uniform, granular films within the 160-220° C. range (FIGS. 59-60). Top-down SEM micrographs of these films show a granular morphology suggestive of metallic films (FIGS. 61-62). Analogous processes have been used for the deposition of elemental Ni films and films containing Cr, Fe, and Mn.

Preparation of Silicon Particles

All reactions were carried out under an argon atmosphere using standard Schlenk line and glovebox techniques.

Un-Capped Si Particles

Figure 63B:
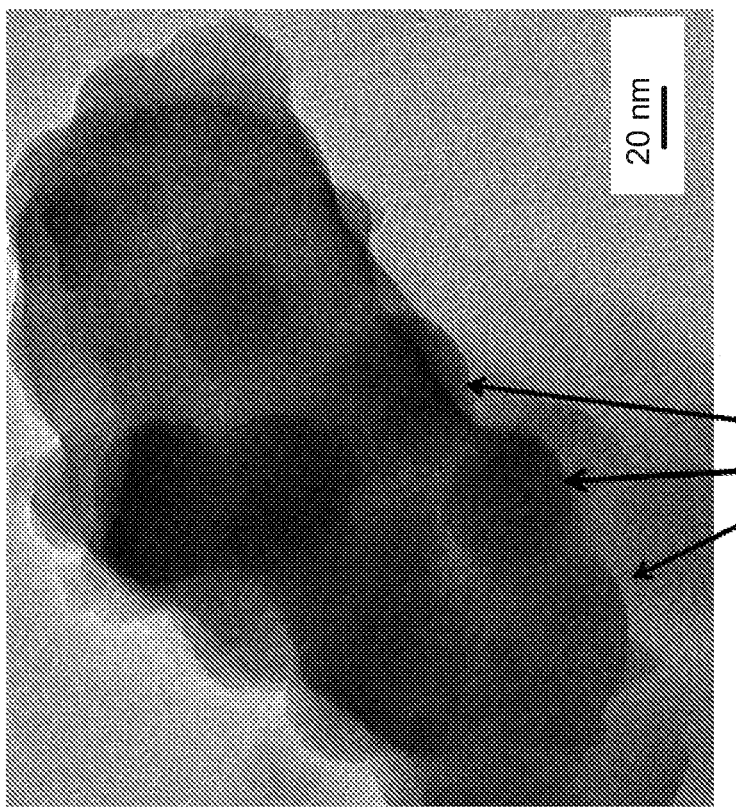
FIG. 63B provides a TEM image of methanol-washed un-capped Si particles.
Figure 63A:
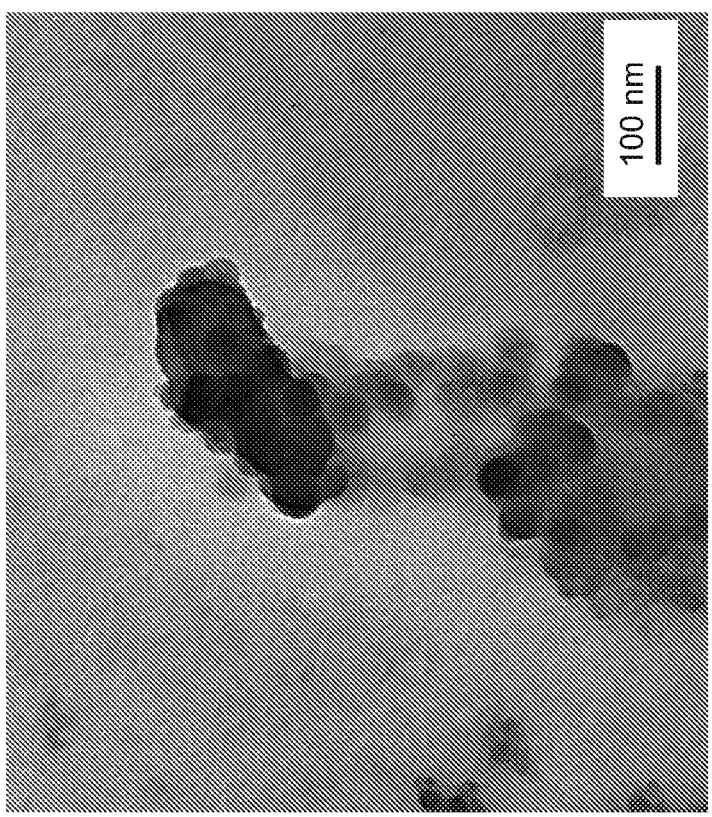
FIG. 63A provides a TEM image_of methanol-washed un-capped Si particles.
Figure 64:
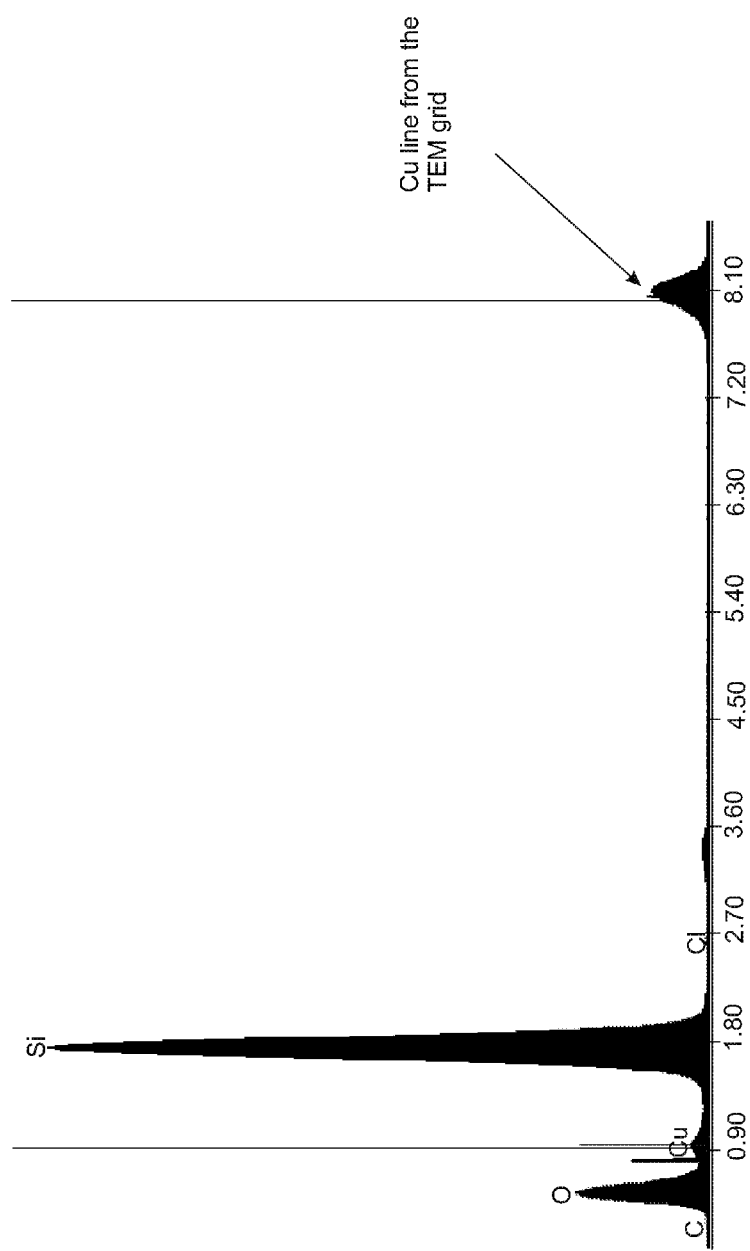
FIG. 64 provides an EDS analysis of methanol-washed Si particles.
Figure 65:
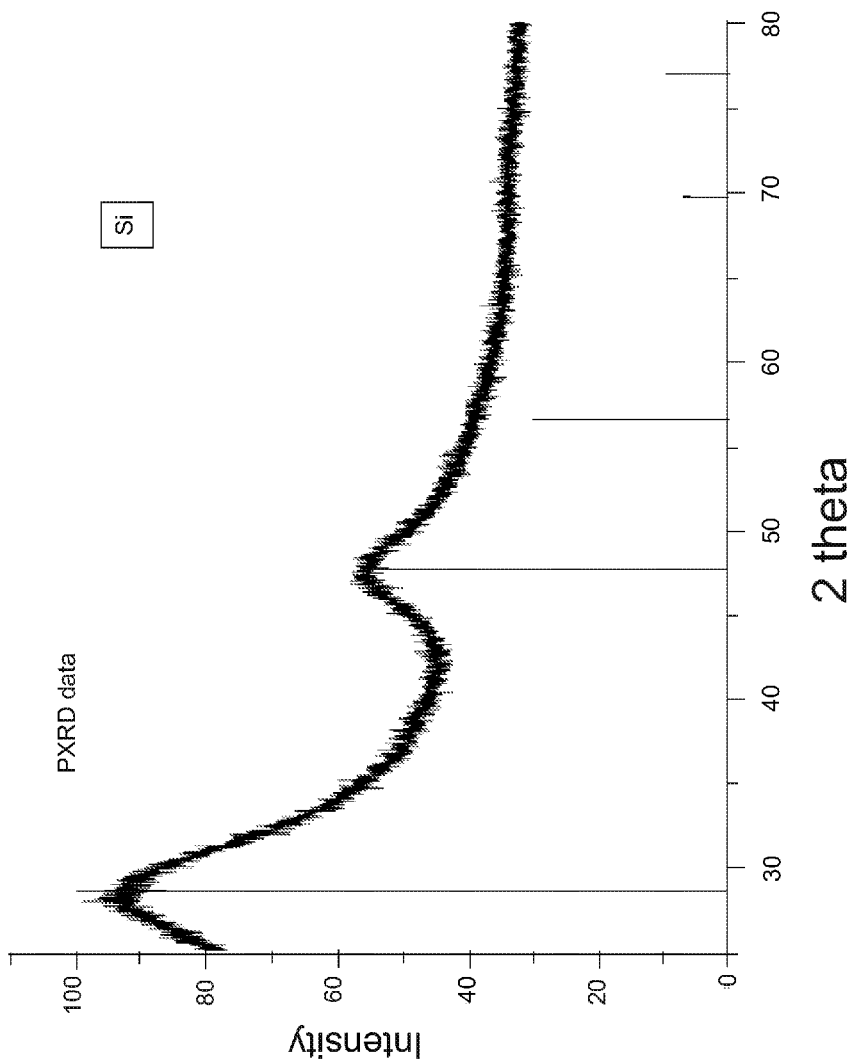
FIG. 65 provides a PXRD spectrum of Si particles.
Figure 66A:
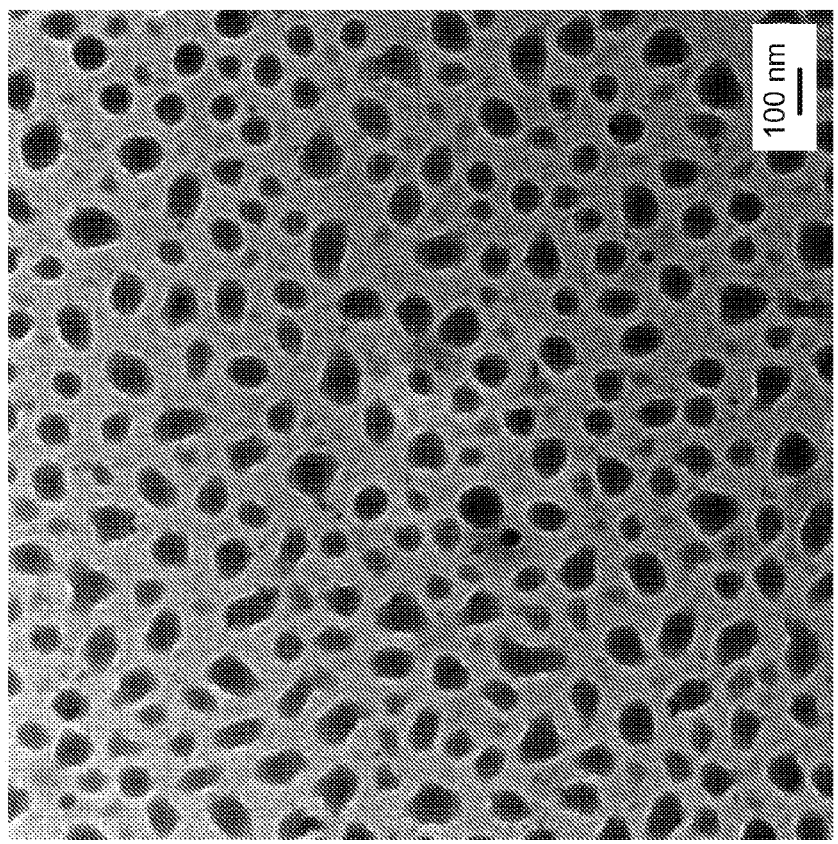
FIG. 66A provides a TEM image of Si particles.
Figure 66B:
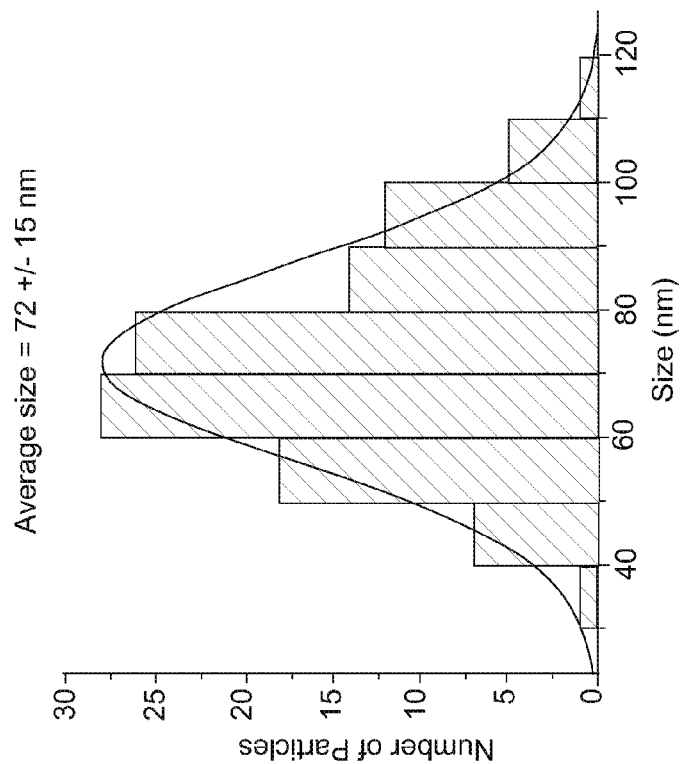
FIG. 66B provides a size distribution of Si particles.

The synthesis of Si particles was performed by taking 2.5 mmol of SiCl$_4$ and 5 mmol of 1,4-bis(trimethylsilyl)dihydropyrazine (DHP) in 15 mL of toluene and refluxing at 110° C. for 6 hours. Then, the solvent and other by-products were removed from the reaction mixture by vacuum drying for 30 mins. A dark brown solid product was isolated and purified using methanol by sonication followed by centrifuging 3 times. The resultant solid was then dried for further characterization. FIG. 63 provides TEM images of methanol washed un-capped Si particles. FIG. 64 provides EDS analysis of methanol washed Si particles. The EDS data exhibits an intense Si signal that is consistent with literature reports for silicon and negligible amounts of C and Cl. EDS collected in different areas of the grid shows very similar signal pattern. The possible existence of surface oxidation is noted since the samples were handled outside after isolation. FIG. 65 provides a PXRD scan of Si particles which matches published reference samples. FIG. 66 provides a TEM image and size distribution of Si particles;

1-Ocatanol Capped Si Particles

Figure 67A:
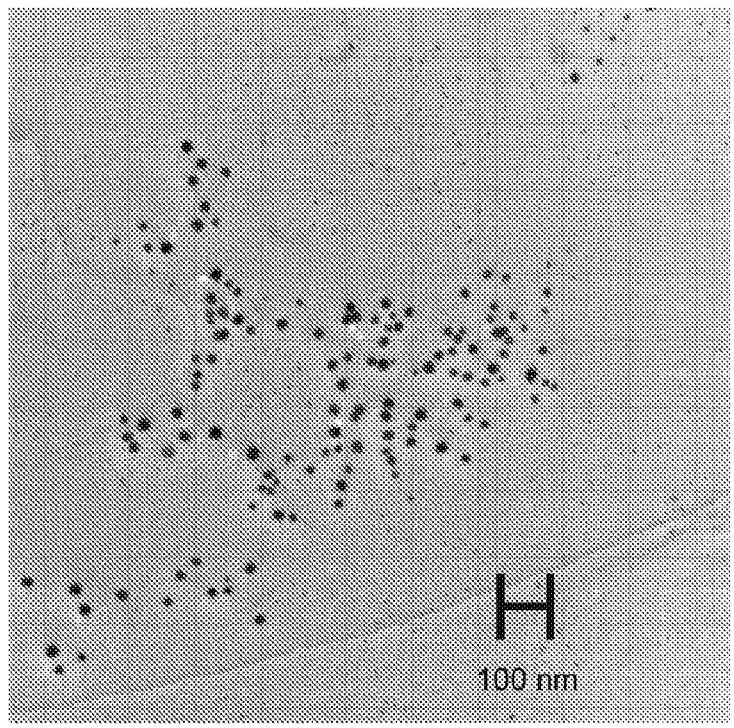
FIG. 67A provides a TEM image of Si particles in which methanol was added before reaction with 1-octanol.
Figure 67B:
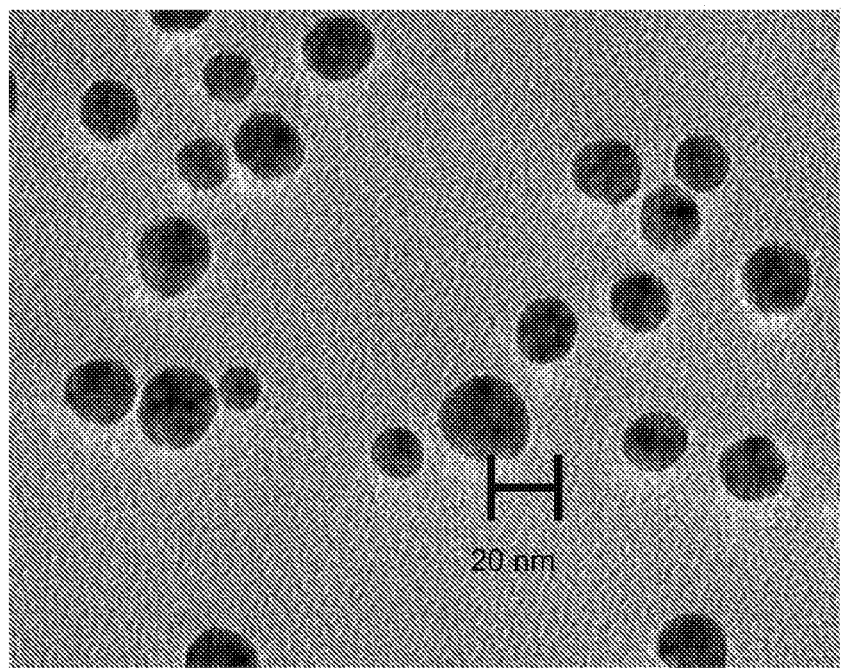
FIG. 67B provides a TEM image of Si particles in which methanol was added before reaction with 1-octanol.

The reaction was initiated as explained above by taking SiCl$_4$ and DHP in toluene and refluxing 110° C. After 3 hours of refluxing, 2 mL of 1-ocatanol was added to the reaction flask. The reaction was continued for another 3 hours. The isolation of particles was carried out as explained in the previous section. It was observed that 1-octanol may react with unreacted species in the reaction mixture. In order to prevent that, MeOH was used as a killing agent. FIG. 67 provides TEM images of Si particles in which methanol was added before reaction with 1-octanol. In general smaller particles are observed with two size distributions (3-4 nm and 12-20 nm)

Preparation of Germanium Particles

Figure 68:
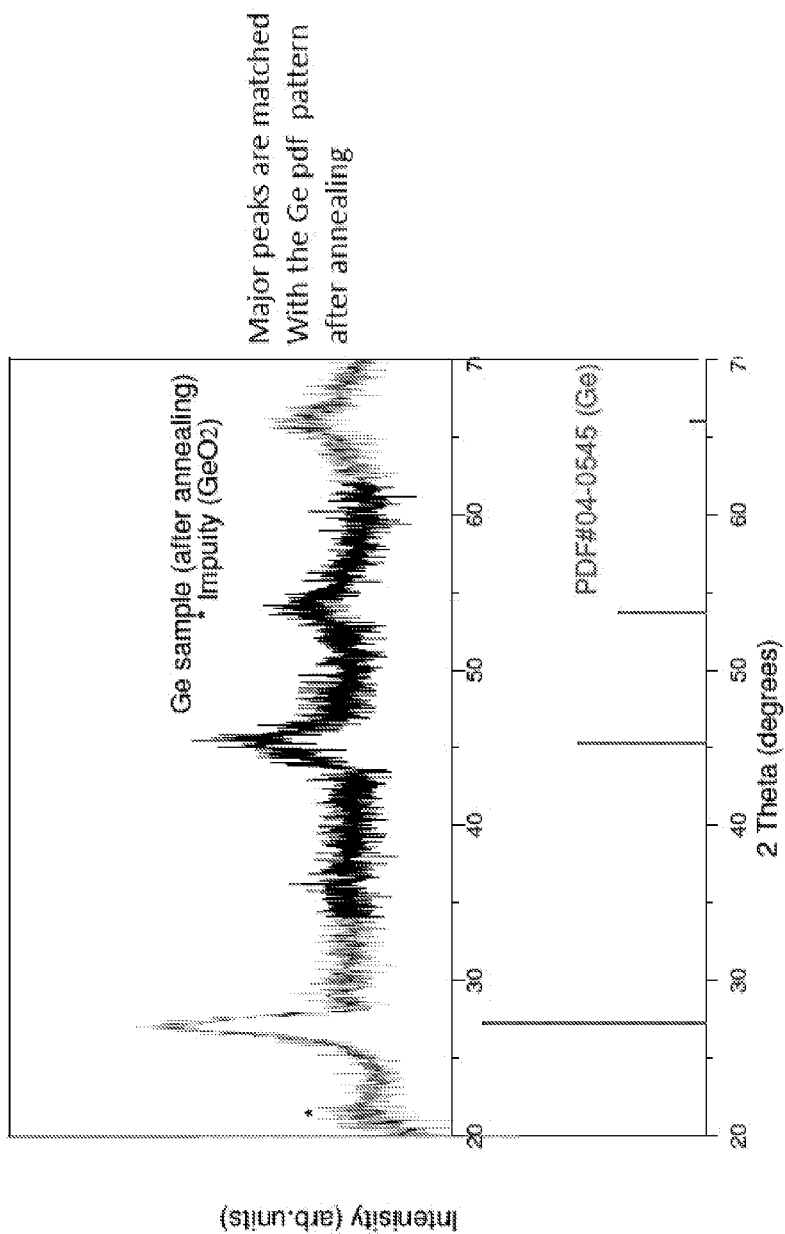
FIG. 68 provides the PXRD spectrum of the formed Ge particles.
Figure 69:
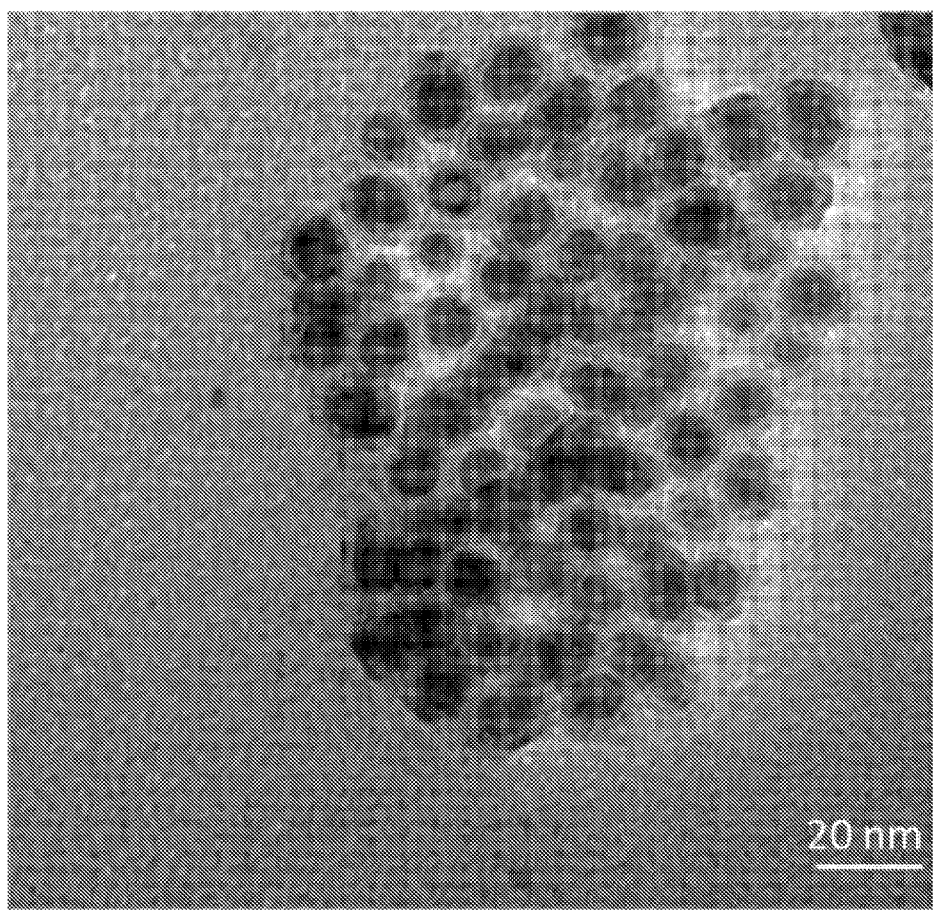
FIG. 69 provides a TEM image of the Ge nanoparticles. Since the samples were handled outside after isolation, it is believed that the lighter area around the nanoparticles may be due to the surface oxidation.

The synthesis of Ge particles was performed by reacting GeCl$_4$ with 1,4-bis(trimethylsilyl)dihydropyrazine (DHP) at a GeCl$_4$:DHP=1:2 molar ratio. The reduction of GeCl$_4$ is observed to be very fast compared to SiCl$_4$. The solution turns black (cloudy) immediately upon addition of GeCl$_4$ to the DHP/Toluene mixture at room temperature. FIG. 68 provides the powder X-ray diffraction pattern of the formed Ge particles. The major peaks are matched with the Ge pdf pattern after annealing. FIG. 69 provides TEM images of the Ge nanoparticles. Since the samples were handled outside after isolation, it is believed that the lighter area around the nanoparticles may be due to the surface oxidation.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method comprising:

providing a vapor of a first compound having an atom in an oxidized state, the atom in an oxidized state being in an oxidation state greater than 0, the atom in an oxidized state being selected from the group consisting of Groups 2-12 of the Periodic Table, the lanthanides, As, Sb, Bi, Te, Si, Ge, Sn, and Al;

providing a vapor of a reducing agent, the reducing agent selected from the group consisting of compounds described by formulae IA and IB:

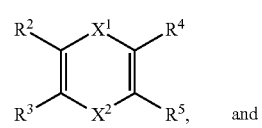

and

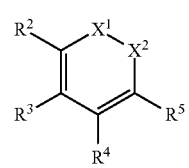

wherein:

$X^1$ is $CR^6(SiR^1R^{1'}R^{1''})$ or $N(SiR^1R^{1'}R^{1''})$;

$X^2$ is $CR^7(SiR^1R^{1'}R^{1''})$ or $N(SiR^1R^{1'}R^{1''})$; and $R^1$, $R^{1'}$, $R^{1''}$, $R^2$, $R^3$, $R^4$, $R^5$, $R^6$, and $R^7$ are each independently H, $C_{1-10}$ alkyl, $C_{6-14}$ aryl, or $C_{4-14}$ heteroaryl; and reacting the vapor of the first compound with the vapor of the reducing agent to convert the atom to a zero oxidation state.

2. The method of claim 1 wherein $R^1$, $R^{1'}$, $R^{1''}$ are each independently $C_{1-10}$ alkyl; $R^2$, $R^3$, $R^4$, $R^5$ are each independently H or $C_{1-10}$ alkyl; and $R^6$ and $R^7$ are H.

3. The method of claim 1 wherein the reducing agent is selected from the group consisting of:

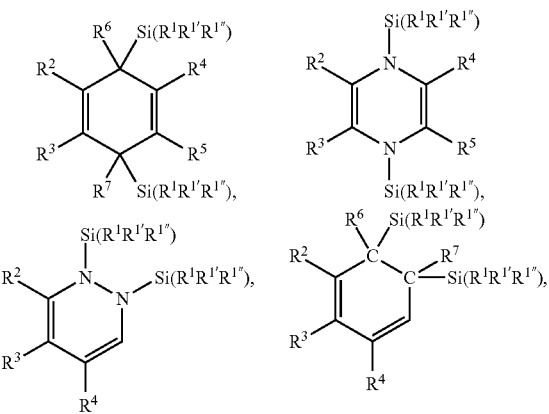

and combinations thereof.

4. The method of claim 3 wherein $R^1$, $R^{1'}$, $R^{1''}$ are each independently $C_{1-10}$ alkyl; $R^2$, $R^3$, $R^4$, $R^5$ are each independently H or $C_{1-10}$ alkyl; and $R^6$, and $R^7$ are H.

5. The method of claim 4 wherein the reducing agent is:

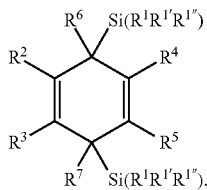

6. The method of claim 1 wherein the atom is in a positive oxidation state of 1, 2, 3, 4, 5, or 6.

7. The method of claim 1 wherein $R^2$, $R^3$, $R^4$, and $R^5$ are each independently hydrogen, methyl, ethyl, n-propyl, isopropyl, n-butyl, sec-butyl, isobutyl, t-butyl, or phenyl.

8. The method of claim 1 wherein $R^1$, $R^{1'}$, and $R^{1''}$ are each independently hydrogen, methyl, ethyl, n-propyl, isopropyl, n-butyl, sec-butyl, isobutyl, t-butyl, or phenyl.

9. The method of claim 1 wherein the atom is Cu, Cr, Mn, Fe, Co, Ti, or Ni.

10. The method of claim 1 comprising a deposition cycle including:
   a) contacting a substrate with the vapor of the first compound having an atom in an oxidized state to form a first modified surface; and
   c) contacting the first modified surface with the vapor of the reducing agent.

11. The method of claim 10 wherein a metal-containing layer is deposited on the substrate.

12. The method of claim 11 wherein the metal-containing layer includes a metal atom in the zero oxidation state.

13. The method of claim 10 wherein the reducing agent is described by formula (IIA):

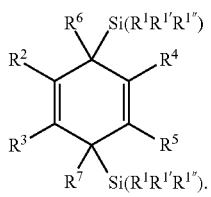

14. The method of claim 10 wherein the substrate is additionally contacted with the vapor of the first compound having an atom in an oxidized state and then the vapor of a reducing agent during a plurality of additional deposition cycles.

15. The method of claim 14 wherein the substrate is coated with from 1 to 5000 deposition cycles.

16. The method of claim 10 wherein the substrate is coated at a temperature from about 50 to 400° C.

17. The method of claim 10 wherein the substrate is contacted with a purge gas after contacting the substrate with vapor of a metal-containing compound including a metal atom in an oxidized state and before contacting the substrate with the vapor of the reducing agent.

18. The method of claim 17 wherein the substrate is contacted with the purge gas after contacting the substrate with the vapor of the reducing agent and before a subsequent step of contacting vapor of a metal-containing compound including a metal atom in an oxidized state.

19. The method of claim 10 wherein the first compound having an atom in an oxidized state is reacted with the reducing agent in a gaseous state.

20. A method of forming a layer on a substrate, the method comprising a deposition cycle including:
   a) contacting a substrate with a vapor of a first compound having an atom in an oxidized state to form a first modified surface, the atom in an oxidized state selected from the group consisting of Groups 2-12 of the Periodic Table, the lanthanides, As, Sb, Bi, Te, Si, Ge, Sn, and Al;
   b) contacting the first modified surface with an acid for a second predetermined pulse time to form a second modified surface; and
   c) contacting the second modified surface with a reducing agent for a third predetermined pulse time to reduce the atom to a zero oxidation state and to form a layer on the substrate, the reducing agent selected from the group consisting of:

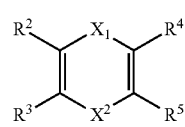

IA

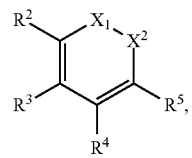

IIB wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$; and
$R^1$, $R^{1'}$, $R^{1''}$, $R^2$, $R^3$, $R^4$, $R^5$, $R^6$, and $R^7$ are each independently H, $C_{1-10}$ alkyl, $C_{6-14}$ aryl, or $C_{4-14}$ heteroaryl.

21. The method of claim 20 wherein the atom is Cu, Cr, Mn, Fe, Co, Ti, or Ni.

22. The method of claim 20 wherein the reducing agent comprises a compound selected from the group consisting of:

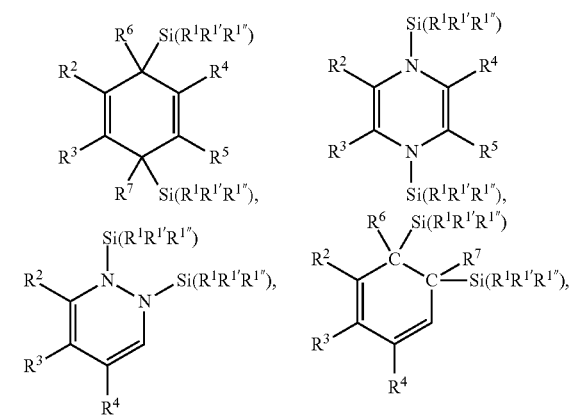

and combinations thereof.

23. The method of claim 20 wherein the reducing agent is:

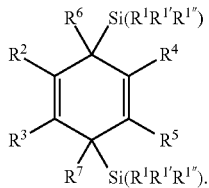

24. The method of claim 20 wherein the atom is in a positive oxidation state of 1, 2, 3, 4, 5, or 6.

25. The method of claim 20 wherein $R^1$, $R^{1'}$, $R^{1''}$ are each independently $C_{1-10}$ alkyl; $R^1$, $R^2$, $R^3$, $R^4$, $R^5$ are each independently H or $C_{1-10}$ alkyl; and $R^6$, and $R^7$ are H.

26. The method of claim 20 wherein $R^1$, $R^{1'}$, $R^{1''}$ are each independently methyl, ethyl, n-propyl, isopropyl, n-butyl, sec-butyl, isobutyl, or t-butyl and $R^2$, $R^3$, $R^4$, and $R^5$ are each independently hydrogen, methyl, ethyl, n-propyl, isopropyl, n-butyl, sec-butyl, isobutyl, or t-butyl.

27. The method of claim 20 wherein the substrate is additionally contacted with the vapor of the first compound having an atom in an oxidized state, the acid, and the vapor of a reducing agent during a plurality of additional deposition cycles.

28. A method of depositing a thin film on a surface of a substrate, the method comprising:
 a) contacting the substrate with a vapor of a metal-containing compound having formula III or IV to form a modified surface on the substrate:

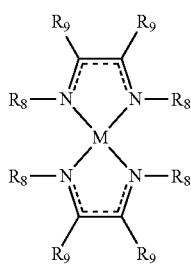

III

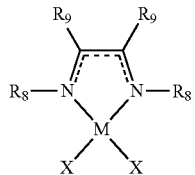

IV wherein:
M is a transition metal selected from Groups 3-10 of the Periodic Table, Ru, Pd, Pt, Rh, Ir, Mg, Al, Sn, or Sb;
$R_8$ is $C_1$-$C_{12}$ alkyl, amino (i.e., —$NH_2$), or $C_6$-$C_{18}$ aryl;
$R_9$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino; and
X is Cl, Br, or I; and
 b) contacting the modified surface with a vapor of an activating compound to form a second modified surface, the activating compound being an acid or a diketone; and
 c) providing a vapor of a reducing agent to convert M to a zero oxidation state, the reducing agent selected from the group consisting of compounds described by formulae IA and IB:

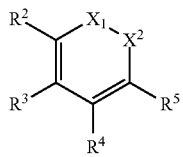

IA

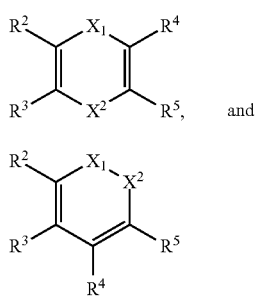

IIB wherein:
$X^1$ is $CR^6(SiR^1R^{1'}R^{1''})$ or $N(SiR^1R^{1'}R^{1''})$;
$X^2$ is $CR^7(SiR^1R^{1'}R^{1''})$ or $N(SiR^1R^{1'}R^{1''})$;
$R^1$, $R^{1'}$, $R^{1''}$, $R^2$, $R^3$, $R^4$, $R^5$, $R^6$, and $R^7$ are each independently H, $C_{1-10}$ alkyl, $C_{6-14}$ aryl, or $C_{4-14}$ heteroaryl.

29. The method of claim 28 wherein steps a) and b) are repeated a plurality of times.

30. The method of claim 29 wherein steps a) and b) are repeated 1 to 5000 times.

* * * * *